US012570698B2

(12) United States Patent
Walensky et al.

(10) Patent No.: US 12,570,698 B2
(45) Date of Patent: Mar. 10, 2026

(54) STABILIZED PEPTIDES FOR COVALENT BINDING TO TARGET PROTEIN

(71) Applicant: Dana-Farber Cancer Institute, Inc., Boston, MA (US)

(72) Inventors: Loren D. Walensky, Newton, MA (US); Gregory H. Bird, Pelham, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 18/306,724

(22) Filed: Apr. 25, 2023

(65) Prior Publication Data

US 2024/0294574 A1 Sep. 5, 2024

Related U.S. Application Data

(63) Continuation of application No. 17/389,761, filed on Jul. 30, 2021, now abandoned, which is a continuation of application No. 15/752,372, filed as application No. PCT/US2016/049083 on Aug. 26, 2016, now abandoned.

(Continued)

(51) Int. Cl.
| | |
|---|---|
| *C07K 14/00* | (2006.01) |
| *C07K 7/08* | (2006.01) |
| *G01N 30/72* | (2006.01) |
| *G01N 33/68* | (2006.01) |
| G01N 30/88 | (2006.01) |

(52) U.S. Cl.
CPC .............. *C07K 14/001* (2013.01); *C07K 7/08* (2013.01); *C07K 14/00* (2013.01); *G01N*
30/72 (2013.01); *G01N 33/6803* (2013.01); *G01N 33/6845* (2013.01); *G01N 2030/8831* (2013.01)

(58) Field of Classification Search
CPC ........ C07K 14/001; C07K 7/08; C07K 14/00; G01N 30/72; G01N 33/6803; G01N 33/6845; G01N 2030/8831
See application file for complete search history.

(56) References Cited

U.S. PATENT DOCUMENTS

| | | | |
|---|---|---|---|
| 5,446,090 A | 8/1995 | Harris | |
| 6,348,558 B1 | 2/2002 | Harris et al. | |

(Continued)

FOREIGN PATENT DOCUMENTS

| | | |
|---|---|---|
| JP | 2008-509378 | 3/2008 |
| JP | 2012-511512 | 5/2012 |

(Continued)

OTHER PUBLICATIONS

Walensky et al., Hydrocarbon-stapled peptides: principles, practice, and progress. J Med Chem. Aug. 14, 2014;57(15):6275-88. doi: 10.1021/jm4011675. Epub Mar. 6, 2014. PMID: 24601557; PMCID: PMC4136684 (Year: 2014).*

(Continued)

*Primary Examiner* — Randall L Beane
(74) *Attorney, Agent, or Firm* — Fish & Richardson P.C.

(57) ABSTRACT

Provided herein is a platform technology for designing stabilized peptides that covalently bind their target protein and thereby inhibit the activity of the target protein. Also provided are exemplary stabilized peptides that can be used for covalent modification of their target proteins.

5 Claims, 35 Drawing Sheets

Specification includes a Sequence Listing.

Related U.S. Application Data

(60) Provisional application No. 62/211,681, filed on Aug. 28, 2015.

(56) References Cited

U.S. PATENT DOCUMENTS

| | | | |
|---|---|---|---|
| 7,723,468 | B2 | 5/2010 | Daffre et al. |
| 8,889,632 | B2 | 11/2014 | Bernal et al. |
| 9,464,125 | B2 | 10/2016 | Link et al. |
| 9,493,510 | B2 | 11/2016 | Skerlj |
| 10,023,613 | B2 | 7/2018 | Guerlavais |
| 11,078,246 | B2 | 8/2021 | Walensky et al. |
| 11,834,520 | B2 | 12/2023 | Walensky et al. |
| 2004/0093164 | A1 | 5/2004 | Carlson et al. |
| 2005/0250680 | A1 | 11/2005 | Walensky et al. |
| 2009/0048164 | A1 | 2/2009 | Colman et al. |
| 2010/0168388 | A1 | 7/2010 | Bernal et al. |
| 2010/0286057 | A1 | 11/2010 | Walensky et al. |
| 2012/0172285 | A1 | 7/2012 | Walensky et al. |
| 2014/0296160 | A1 | 10/2014 | Walensky et al. |
| 2014/0370042 | A1 | 12/2014 | Walensky et al. |
| 2015/0051249 | A1 | 2/2015 | Walensky |
| 2015/0119551 | A1 | 4/2015 | Bernal et al. |
| 2015/0353606 | A1* | 12/2015 | Skerlj ............... A61P 35/00 435/375 |
| 2019/0002506 | A1 | 1/2019 | Walensky et al. |
| 2019/0002514 | A1 | 1/2019 | Walensky et al. |
| 2021/0070802 | A1 | 3/2021 | Walensky et al. |
| 2022/0213146 | A1 | 7/2022 | Walensky et al. |
| 2024/0132544 | A1 | 4/2024 | Walensky et al. |
| 2024/0228539 | A9 | 7/2024 | Walensky et al. |

FOREIGN PATENT DOCUMENTS

| | | | | |
|---|---|---|---|---|
| JP | 2015-504064 | 2/2015 | | |
| WO | WO 1999/14259 | 3/1999 | | |
| WO | WO 1999/34833 | 7/1999 | | |
| WO | WO-2005044839 | A2 * | 5/2005 | ............ A61K 38/00 |
| WO | WO 2005/075645 | 8/2005 | | |
| WO | WO 2008/121767 | 10/2008 | | |
| WO | WO 2009/108261 | 9/2009 | | |
| WO | WO 2010/060112 | 5/2010 | | |
| WO | WO 2010/068684 | 6/2010 | | |
| WO | WO 2010/148335 | 12/2010 | | |
| WO | WO 2014/110420 | 7/2014 | | |
| WO | WO 2014/151369 | 9/2014 | | |
| WO | WO 2017/040323 | 3/2017 | | |
| WO | WO 2017/040329 | 3/2017 | | |
| WO | WO 2019/118719 | 6/2019 | | |

OTHER PUBLICATIONS

Adams et al., "PHENIX: A Comprehensive Python-based System for Macromolecular Structure Solution," Acta Crystallogr D Biol Crystallogr, 2010, 66(pt. 2)213-221.

Altschul et al., "Gapped BLAST and PSI-BLAST: a new generation of protein database search programs," Nucleic Acids Research, 1997, 25(17):3389-3402.

Anderson et al., "CCT241533 is a potent and selective inhibitor of CHK2 that potentiates the cytotoxicity of PARP inhibitors," Cancer Research, 2011, 74:463-472.

Balaram, "Non-standard amino acids in peptide design and protein engineering," Current Opinion in Structural Biology, 1992, 2(6):845-851.

Bang et al., "Total Chemical Synthesis of Crambin," J. Am. Chem. Soc., 2004, 126:1377-1383.

Beroukhim et al., "The landscape of somatic copy-number alteration across human cancers," Nature, Feb. 2010, 463(7283):899-905.

Billard "Design of novel BH3 mimetics for the treatment of chronic lymphocytic leukemia", Leukemia, 2012, 26(9):2032-2038.

Bird et al., "Chemical Synthesis and Hydrocarbon-stapled peptides for protein interaction research and therapeutic targeting," Current Protocol in Chemical Biology, Sep. 2011, 3(3):99-117.

Bird et al., "Synthesis and Biophysical Characterization of Stabilized a-Helices of BCL-2 Domains," Methods Enzymol., 2008, 446:369-386.

Blackwell et al., "Highly Efficient Synthesis of Covalently Cross-Linked Peptide Helices by Ring-Closing Metathesis," Angewandte Chem. Int. Ed., 1994, 37(23):3281-4.

Blackwell et al., "Ring-closing metathesis of olefinic peptides: Design, synthesis, and structural characterization of macrocyclic helical peptides," Journal of Organic Chemistry, 2001, 16:5291-5302.

Boehrer et al., "Suppression of the DNA damage response in acute myeloid leukemia versus myelodysplastic syndrome," Oncogene, 2009, 28(22):2205-2218.

Bork et al., "Go hunting in sequence databases but watch out for traps," Trends in Genetics, 1996, 12:425-427.

Bork, "Powers and Pitfalls in Sequence Analysis: The 70% Hurdle," Genome Research, 2000, 10:398-400.

Brenner, "Errors in genome annotation," Trends in Genetics, 1999, 15:132-133.

Bridges et al., "Niraparib (MK-4827), a Novel poly(ADP-Ribose) Polymerase Inhibitor, Radiosensitizes Human Lung and Breast Cancer Cells," Oncotarget, 2014, 5(13):5076-5086.

Brock et al., "Radiosensitization of human and rodent cell lines by INO-1001, a novel inhibitor of poly(ADP-ribose) polymerase," Cancer Letters, 2004, 205(2):155-160.

Brunel et al., "Synthesis of constrained helical peptides by thioether ligation application to analogs of gp41," Chemical Communications, 2005, 20:2552-4.

Chapman et al., "A highly stable short a-helix constrained by a main-chain hydrogen-bond surrogate," Journal of the American Chemical Society, 2004, 126(39):12252-12253.

Chin et al., "Design and Evolution of a Miniature Bcl-2 Binding Protein," Angew Chem Int Ed Engl., 2001, 40:3806-09.

Chonghaile et al., "Mimicking the BH3 domain to kill cancer cells," Oncogene, 2009, 27: S149-S157.

Clinicaltrials.gov, [online], "Phase I Study of MIK665, a Mcl-1 Inhibitor, in Patients With Refractory or Relapsed Lymphoma or Multiple Myeloma," Dec. 14, 2016, retrieved on Nov. 16, 2020, retrieved from URL<https://www.clinicaltrials.gov/ct2/show/NCT02992483?term=NCT02992483&draw=2&rank=1>, Clinical Trial ID NCT02992483, 8 pages.

Clinicaltrials.gov, [online], "Phase I Study of S64315 Administred Intravenously in Patients With Acute Myeloid Leukaemia or Myelodysplastic Syndrome," Dec. 1, 2016, retrieved on Nov. 16, 2020, retrieved from URL<https://www.clinicaltrials.gov/ct2/show/NCT02979366?term=NCT02979366&draw=2&rank=1>, Clinical Trial ID NCT02979366, 10 pages.

Clinicaltrials.gov, [online], "Safety, Tolerability, Pharmacokinetics and Efficacy of AMG 397 in Subjects With Selected Relapsed or Refractory Hematological Malignancies," Mar. 14, 2018, retrieved on Nov. 16, 2020, retrieved from URL<https://www.clinicaltrials.gov/ct2/show/NCT03465540?term=NCT03465540&draw=2&rank=1>, Clinical Trial ID NCT03465540, 20 pages.

Curtin et al., "Novel poly(ADP-ribose) polymerase-1 Inhibitor, AG14361, Restores Sensitivity to Temozolomide in Mismatch Repair-Deficient Cells," Clin Cancer Res, 2004, 10(3):881-889.

Daniel et al., "Inhibition of poly(ADP-ribose) polymerase-1 enhances temozolomide and topotecan activity against childhood neuroblastoma," Cancer Therapy: Preclinical, 2009, 15(4):1241-1249.

Day et al., "Structure of the BH3 Domains From the p53-inducible BH3-only Proteins Noxa and Puma in Complex With Mcl-1," J Mol. Biol., 2008, 380(5):958-971.

Devi et al., "Antibodies to poly[((2->8)-alpha-N-acetylneuraminic Acid] and poly[(2->9))-alpha-N-acetylneuraminic Acid] Are Elicited by Immunization of Mice With *Escherichia coli* K92 Conjugates: Potential Vaccines for Groups B and C Meningococci and *E. coli* K1" Proc. Natl. Acad. Sci. USA, 1991, 88(16):7175-7179.

Doerks et al., "Protein annotation: detective work for function prediction," Trends in Genetics, 1998, 14:248-250.

Donawho et al., "ABT-888, and orally active poly(ADP-Ribose) polymerase inhibitor that potentiates DNA-damaging agents in preclinical tumor models," Clinical Cancer Research, 2007, 13(9):2728-2737.

(56) References Cited

OTHER PUBLICATIONS

Emsley et al., "Coot: Model-Building Tools for Molecular Graphics," Acta Crystallogr D Biol Crystallogr, 2004, 60:2126-2132.

European Search Report in European Application No. 16842712.8, dated Jan. 24, 2019, 19 pages.

Evans, "Scaling and Assessment of Data Quality," Acta Crystallogr D Biol Crystallogr, 2006, 62(Pt. 1):72-82.

Fattom et al., "Serum Antibody Response in Adult Volunteers Elicited by Injection of Streptococcus pneumoniae Type 12F Polysaccharide Alone or Conjugated to Diphtheria Toxoid," Infect. Immun., 1990, 58(7):2309-2312.

Fields et al., Chapter 3 in Synthetic Peptides: A user's guide ed. Grant, W.H. Freeman & Co. New York, NY., 1992 p. 77-183.

Golding et al., "Improved ATM kinase inhibitor KU-60019 radiosensitizes glioma cells, compromises insulin, AKT and ERK prosurvival signaling, and inhibits migration and invasion," Mol. Cancer Ther, 2009, 8(10):2894-2902.

Guerra et al., "Precision Targeting of BFL-1/A1 and an ATM Co-dependency in Human Cancer," Cell reports, Sep. 25, 2018, 24(13):3393-403.

Haney et al., "Promoting peptide a-helix formation with dynamic covalent oxime side-chain cross-links," Chemical Communications, Jun. 2011, 47:10915-10917.

Haq et al., "BCL2A1 is a lineage-specific antiapoptotic melanoma oncogene that confers resistance to BRAF inhibition," Proc Natl Acad Sci USA, 2013, 110(11):4321-4326.

Hickson et al., "Identification and characterization of a novel and specific inhibitor of the ataxia-telangiectasia mutated kinase ATM," Cancer Res, 2004, 64(24):9152-9159.

Holm et al., "Electrophilic Affibodies Forming Covalent Bonds to Protein Targets," The Journal of Biological Chemistry, Nov. 2009, 284(47):32906-32913.

Horne et al., "Sequence-based Design of alpha/beta-peptide Foldamers That Mimic BH3 Domains," Angew Chen Int Ed Engl., 2008, 47(15):2853-6.

Jackson et al., "An indolocarbazole inhibitor of human checkpoint kinase (Chk1) abrogates cell cycle arrest caused by DNA damage," Cancer Research, 2000, 60:566-572.

Jackson et al., "General Approach to the synthesis of short a-helical peptides," Journal of American Chemical Society, 1991, 113:9391-9392.

Jobson et al., "Identification of a Bis-guanylhydrazone [4,4'-Diacetyldiphenylurea-bis(guanylhydrazone); NSC 109555] as a novel chemotype for inhibition of Chk2 Kinase," Molecular Pharmacology, 2007, 72:876-884.

Kabsch, "Integration, Scaling, Space-Group Assignment and Post-Refinement," Acta Crystallogr D Biol Crystallogr, 2010, 66(Pt 2):133-144.

Kawamoto et al., "Design of Triazole-Stapled BCL9 a-Helical Peptides to Target the b-Catenin/B-Cell CLL/Lymphoma 9 (BCL9) Protein-Protein Interaction," Journal of Medicinal Chemistry, 2012, 55(3):1137-1146.

Kemp et al., "The Structure and Energetics of Helix Formation by Short Templated Peptides in Aqueous Solution. 2. Characterization of Helical Structure of Ac-Hel1-Ala6-OH," Journal of the American Chemical Society, 1996, 118(18):4240-4248.

Kim et al., "Oxidative stress attenuates Fas-mediated apoptosis in Jurkat T cell line through Bfl-1 induction," Oncogene, 2005, 24, 1252-1261.

Kumita et al., "Photo control of helix content in a short peptide," Proceedings of the National Academy of Sciences, 2000, 3803-3808.

Labelle et al., "A stapled BIM peptide overcomes apoptotic resistance in hematologic cancers," J Clin Invest, 2012, 122(6): 2018-2031.

Leshchiner et al., "Direct activation of full-length proapoptotic BAK, Proc Natl Acad Sci USA," 2013, 110(11):E986-95.

Li et al., "Comparative Immunogenicities of Vi Polysaccharide-Protein Conjugates Composed of Cholera Toxin or Its B Subunit as a Carrier Bound to High- Or Lower-Molecular-Weight Vi" Infect. Immun., 1989, 57(12):3823-3827.

Liu et al., "Iniparib nonselectively modifies cysteine containing proteins in tumor cells and is not a bona fide PARP inhibitor," Cancer Therapy: Preclinical, 2012, 18(2):510-523.

Lovell et al., "Membrane Binding by tBid Initiates an Ordered Series of Events Culminating in Membrane Permeabilization by Bax," Cell, 2008, 135, 1074-1084.

Madden et al., "Facile synthesis of stapled, structurally reinforced peptide helices via a photoinduced intramolecular 1,3-dipolar cycloaddition reaction," Chem. Commun. (Camb), Oct. 2009, 7(37):5588-5590.

Madden et al., "Synthesis of Cell-Permeable Stapled Peptide Dual Inhibitors of the p53-Mdm2/Mdmx Interactions via Photoinduced Cycloaddition," Bioorg. Med. Chem. Letter, 2011, 21(5):1472-1475.

McCoy et al., "Phaser Crystallographic Software," J Appl Crystallogr, 2007, 40(Pt 4):658-674.

Menear et al., "4-[3-(4-Cyclopropanecarbonylpiperazine-1-carbonyl)-4-flurobenzyl]-2H-phthalazin-1-one: a novel bioavailable inhibitor of poly(ADP-ribose Polymerase-1," Journal of Medicinal Chemistry, 2008, 51(20):6581-6591.

Ngo et al., "Computational Complexity, Protein Structure Prediction, and the Levinthal Paradox," The Protein Folding Problem and Tertiary Structure Prediction, 1994, 433-506.

Orner et al., "Toward Proteomimetics: Terphenyl Derivatives as Structural and Functional Mimics of Extended Regions of an a-Helix," Journal of the American Chemical Society, 2001, 123(22):5382-5383.

PCT International Preliminary Report on Patentability in International Appln. No. PCT/US2016/049083, dated Mar. 6, 2018, 13 pages.

PCT International Preliminary Report on Patentability in International Appln. No. PCT/US2016/049095, dated Mar. 6, 2018, 12 pages.

PCT International Preliminary Report on Patentability in International Appln. No. PCT/US2018/065438, dated Jun. 16, 2020, 10 pages.

PCT International Search Report and Written Opinion in International Appln. No. PCT/US2016/049083, dated Feb. 16, 2017, 19 pages.

PCT International Search Report and Written Opinion in International Appln. No. PCT/US2016/049095, dated Feb. 21, 2017, 17 pages.

PCT International Search Report and Written Opinion in International Appln. No. PCT/US2018/065438, dated May 22, 2019, 18 pages.

Penning et al., "Optimization of Phenyl-Substituted Benzimidazole Carboxamide poly(ADP-ribose) Polymerase Inhibitors: Identification of (S)-2-(2-fluoro-4-(pyrrolidin-2-yl)phenyl)-1H-benzimidazole-4-carboxamide (A-966492), a Highly Potent and Efficacious Inhibitor," J Med Chem, 2010, 53(8):3142-3153.

Phelan et al., "A general method for constraining short peptides to an a-helical conformation," Journal of the American Chemical Society, 1997, 119(3):455-460.

Pitter et al., "Dissection of the BCL-2 Family Signaling Network With Stabilized Alpha-Helices of BCL-2 Domains," Methods Enzymol., 2008, 446:387-408.

Schafmeister et al., "An All-Hydrocarbon cross-linking system for enhancing the helicity and metabolic stability of peptides," Journal of the American Chemical Society, 2000, 122(24):5891-5892.

Shepherd et al., "Single Turn Peptide Alpha Helices with Exceptional Stability in Water," Journal of the American Chemical Society, 2005, 127(9):2974-2983.

Skolnick et al., "From genes to protein structure and function: novel applications of computational approaches in the genomic era," Trends in Biotech., 2000, 18(1):34-39.

Smaill et al., "Synthesis and structure—activity relationships of N-6 substituted analogues of 9-hydroxy-4-phenylpyrrolo[3,4-c]carbazole-1,3(2H,6H)-diones as inhibitors of Weel and Chk1 checkpoint kinases," European Journal of Medicinal Chemistry, 2008, 43:1276-1296.

(56)            References Cited

OTHER PUBLICATIONS

Smith et al., "The challenges of genome sequence annotation or "The devil is in the details,"" Nature Biotechnology, 1997 15:1222-1223.

Spokoyny et al., "A perfluoroaryl-cysteine SnAr Chemistry approach to unprotected peptide stapling," Journal of American Chemical Society, 2013, 135(16):5946-5949.

Stewart et al., "The MCL-1 BH3 Helix Is an Exclusive MCL-1 Inhibitor and Apoptosis Sensitizer," Nature Chemical Biology, 2010, 6(8):595-601.

Szu et al., "Laboratory and Preliminary Clinical Characterization of Vi Capsular Polysaccharide-Protein Conjugate Vaccines," Infect. Immun., 1994, 62(10):4440-4444.

Szu et al., "Relation Between Structure and Immunologic Properties of the Vi Capsular Polysaccharide," Infect. Immun., 1991, 59:4555-4561.

Szu et al., "Vi Capsular Polysaccharide-Protein Conjugates for Prevention of Typhoid Fever. Preparation, Characterization, and Immunogenicity in Laboratory Animals," J Exp. Med., 1987, 166(5):1510-1524.

Teng et al., "Structure-based Design and Synthesis of (5-arylamino-2H-pyrazol-3-yl)-biphenyl-2',4'-diols as Novel and Potent Human CHK1 Inhibitors," J Med Chem, 2007, 50(22):5253-6.

Tokuriki et al., "Stability effects of mutations and protein evolvability," Current Opinion in Structural Biology, 2009, 19: 596-604.

Walensky et al., "A Stapled BID BH3 Helix Directly Binds and Activates BAX," Molecular Cell, Oct. 2006, 24:199-210.

Walensky et al., "Activation of Apoptosis in Vivo by a Hydrocarbon-Stapled BH3 Helix," Science, 2004, 305(5689):1466-1470.

Wells, "Additivity of Mutational Effects in Proteins," Biochemistry, 1990, 29:8509-8517.

Wikipedia.org, [online], "Acetylation," Feb. 17, 2021, retrieved on Mar. 22, 2021, retrieved from URL<https://en.wikipedia.org/wiki/Acetylation#N-terminal_acetylation>, 16 pages.

Wilen et al., "Strategies in Optical Resolutions," Tetrahedron 33:2725, 1977.

Wilen, "Tables of Resolving Agents and Optical Resolutions," EX. Eliel, Ed., Univ. of Notre Dame Press, Notre Dame, IN, 1972, 268-308.

Williams et al., "Asymmetric synthesis of monosubstituted and a,a-Disubstituted a-Amino acids via diastereoselective glycine enolate alkylations," Journal of the American Chemical Society, 1991, 113(24):9276-9286.

Williams et al., "Efficient asymmetric synthesis of n-tert-butoxycarbonyl a-aminoacids using 4-tert-butoxycarbonyl-5,6-diphenylmorpholin-2-one(R)-(N-tert-butoxycarbonyl)Allylglycine: (4-pentenoic acid, 2-[[(1, 1-dimethylethoxy)carbonyl] amino]-,(2 R)-)" Organic Synthesis, 2003, 80:31-37.

Winter, "xia2: an expert system for macromolecular crystallography data reduction," Appl Crystallogr, 2010, 43(1):186-190.

Yang et al., "[11] Calculation of Protein conformation from circular dichroism," Macromolecular Conformation: Spectroscopy, 1986, 208-269.

Youle et al., "The BCL-2 protein family: opposing activities that mediate cell death," Nature reviews Molecular cell biology, 2008, 9(1):47-59.

Zabludoff et al., "AZD7762, a novel checkpoint kinase inhibitor, drives checkpoint abrogation and potentiates DNA-targeted therapies," Molecular Cancer Therapeutics, 2008, 7(9):2955-2966.

U.S. Appl. No. 15/752,358, 2019/0002514, U.S. Pat. No. 11,078,246, filed Feb. 13, 2018, Walensky.

U.S. Appl. No. 17/353,206, filed Jun. 21, 2021, Walensky.

U.S. Appl. No. 17/674,379, filed Feb. 17, 2022, Walensky.

U.S. Appl. No. 17/934,704, filed Sep. 23, 2022, Walensky.

U.S. Appl. No. 18/315,923, filed May 11, 2023, Walensky.

U.S. Appl. No. 15/752,372, 2019/0002506, filed Feb. 13, 2018, Walensky.

U.S. Appl. No. 17/389,761, 2022/0213146, filed Jul. 30, 2021, Walensky.

U.S. Appl. No. 16/766,201, 2021/0070802, U.S. Pat. No. 11,834,520, filed May 21, 2020, Walensky.

U.S. Appl. No. 18/494,623, 2024/0132544, filed Oct. 25, 2023, Walensky.

Ali et al., "Stapled Peptides Inhibitors: A New Window for Target Drug Discovery," Comput Struct Biotechnol J, Feb. 19, 2019, 17:263-281.

Awasthi et al., "ATM and ATR signaling at a glance," Journal of the Cell Science, Dec. 1, 2015, 128(23):4255-4262.

Ayaz et al., "Conformational Adaption May Explain the Slow Dissociation Kinetics of Roniciclib (BAY 1000394), a Type I Cdk Inhibitor With Kinetic Selectivity for CDK2 and CDK9," ACS Chem Biol, Jun. 17, 2016, 11(6):1710-1719.

Baggio et al., "N-locking stabilization of covalent helical peptides: Application to Bfl-1 antagonists," Chem Biol Drug Des, Apr. 2020, 95(4):412-426.

Barile et al., "hBfl-1 /hNOXA Interaction Studies Provide New Insights on the Role of Bfl-1 in Cancer Cell Resistance and for the Design of Novel Anticancer Agents," ACS Chem Biol, Feb. 17, 2017, 12(2):444-455.

Bird et al., "Biophysical determinants for cellular uptake of hydrocarbon-stapled peptide helices," Nat Chem Biol., Aug. 22, 2016, 12(10):845-552.

Booth et al., "The Chk1 inhibitor SRA737 synergizes with PARPI inhibitors to kill carcinoma cells," Cancer Biology and Therapy, Jul. 19, 2018, 19(9):786-796.

Caenepeel et al., "Abstract 2027: Preclinical evaluation of AMG 176, a novel, potent and selective Mcl-1 inhibitor with robust anti-tumor activity in Mcl-1 dependent cancer models," Abstract, Presented at the Proceedings of the American Association for Cancer Research Annual Meeting, Apr. 1-5, 2017, Washington, DC; Cancer Research, Jul. 1, 2017, 77(13 Supplement), 4 pages.

Gunnoo et al., "Bioconjugation—Using selective chemistry to enhance the properties of proteins and peptides as therapeutics and carriers," Organic & Biomolecular Chemistry, Sep. 14, 2016, 14(34):8002-8013.

Harvey et al., "Crystal Structures of Anti-apoptotic BFL-1 and Its Complex with a Covalent Stapled Peptide Inhibitor," Structure, Jan. 2, 2018, 26(1):153-160.

Hong et al., "Phase I Study of LY2606368, a Checkpoint Kinase 1 Inhibitor, in Patients With Advanced Cancer," J Clin Oncol, May 20, 2016, 34(15):1764-1771.

Huhn et al., "Selective Covalent Targeting of Anti-Apoptotic BFL-1 by Cysteine-Reactive Stapled Peptide Inhibitors," Cell Chem Biol., Sep. 22, 2016, 23(9):1123-1134.

Kotschy et al., "The MCL1 Inhibitor S63845 Is Tolerable and Effective in Diverse Cancer Models," Nature, Oct. 27, 2016, 538(7626):477-482.

Laird et al., "Talazoparib Is a Potent Radiosensitizer in Small Cell Lung Cancer Cell Lines and Xenografts," Clin Cancer Res, Oct. 15, 2018, 24(20):5143-5152.

Lau et al., "Functionalised staple linkages for modulating the cellular activity of stapled peptides," Chemical Science, Mar. 10, 2014, 5(5):1804-1809.

Lau et al., "Peptide stapling techniques based on different macrocyclisation. chemistries," Chemical Society Reviews, Jan. 7, 2015, 44(1):91-102.

Leverson, "A New Staple: Peptide-Targeted Covalent Inhibitors," Cell chemical biology, Sep. 22, 2016, 23(9):1043-1044.

McGonigle et al., "E7449: A Dual Inhibitor of PARP1/2 and tankyrase 1/2 Inhibits Growth of DNA Repair Deficient Tumors and Antagonizes Wnt Signaling," Oncotarget, Oct. 20, 2015, 6(38):41307-41323.

Meyers et al., "Computational correction of copy number effect improves specificity of CRISPR-Cas9 essentiality screens in cancer cells," Nat. Genet, Oct. 30, 2017, 49(12):1779-1784.

Nakajima et al., "Noxa determines localization and stability of MCL-1 and consequently ABT-737 sensitivity in small cell lung cancer", Cell Death & Disease, Feb. 13, 2014, 5(2):e1052, 10 pages.

O'Connor et al., "The PARP Inhibitor AZD2461 Provides Insights Into the Role of PARP3 Inhibition for Both Synthetic Lethality and Tolerability With Chemotherapy in Preclinical Models," Cancer Res, Oct. 15, 2016, 76(20):6084-6094.

(56) References Cited

OTHER PUBLICATIONS

Roberts et al., "Targeting BCL2 With Venetoclax in Relapsed Chronic Lymphocytic Leukemia," N Engl J Med., Jan. 28, 2016, 374(4):311-322.

Scagliotti et al., "Phase II evaluation of LY2603618, a first generation CHK1 inhibitor, in combination with pemetrexed in patients with advanced or metastatic non-small cell lung cancer," Invest New Drugs, Oct. 2016; Epub Jun. 27, 2016, 34(5):625-635.

Tsherniak et al., "Defining a Cancer Dependency Map," Cell, Jul. 27, 2017, 170(3):564-576.

Walensky et al., "Hydrocarbon-stapled peptides: Principles, practice and progress," Journal of Medicinal Chemistry, Aug. 14, 2014, 57(15):6275-6288.

Weber et al., "ATM and ATR as therapeutic targets in cancer," Pharmacology and Therapeutics, May 2015; Available online Dec. 13, 2014, 149:124-138.

Zhu et al., "Identification of a Novel Senolytic Agent, Navitoclax, Targeting the Bcl-2 Family of Anti-Apoptotic Factors," Aging Cell, Mar. 18, 2016, 15(3):428-435.

* cited by examiner

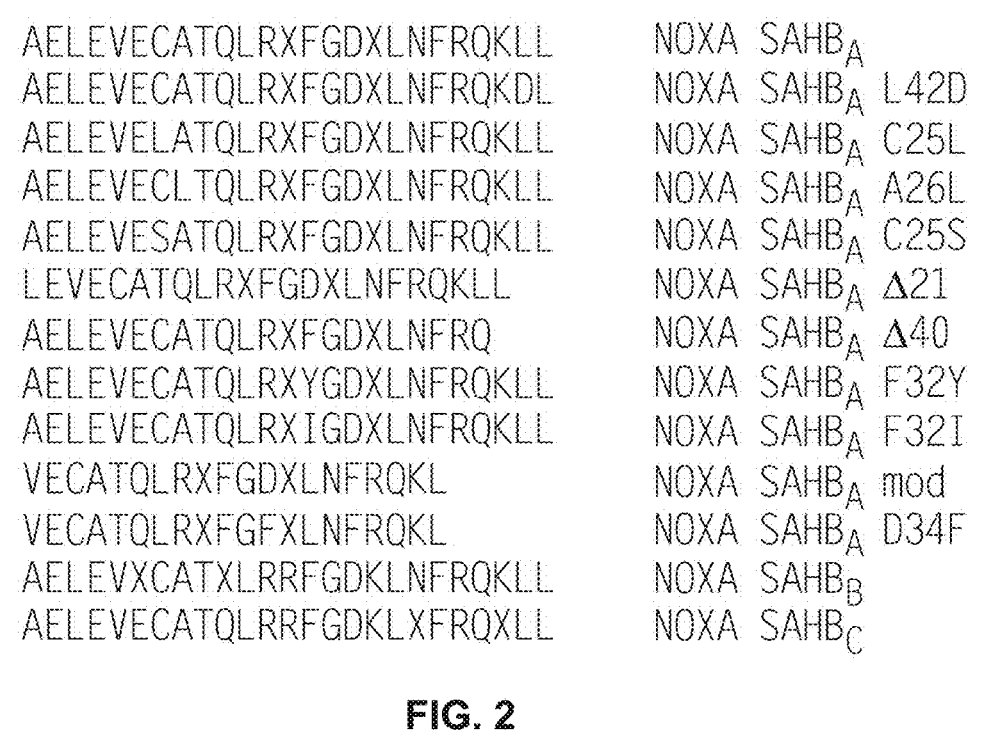

```
AELEVECATQLRXFGDXLNFRQKLL        NOXA SAHB_A
AELEVECATQLRXFGDXLNFRQKDL        NOXA SAHB_A L42D
AELEVELATQLRXFGDXLNFRQKLL        NOXA SAHB_A C25L
AELEVECLTQLRXFGDXLNFRQKLL        NOXA SAHB_A A26L
AELEVESATQLRXFGDXLNFRQKLL        NOXA SAHB_A C25S
LEVECATQLRXFGDXLNFRQKLL          NOXA SAHB_A Δ21
AELEVECATQLRXFGDXLNFRQ           NOXA SAHB_A Δ40
AELEVECATQLRXYGDXLNFRQKLL        NOXA SAHB_A F32Y
AELEVECATQLRXIGDXLNFRQKLL        NOXA SAHB_A F32I
VECATQLRXFGDXLNFRQKL             NOXA SAHB_A mod
VECATQLRXFGFXLNFRQKL             NOXA SAHB_A D34F
AELEVXCATXLRRFGDKLNFRQKLL        NOXA SAHB_B
AELEVECATQLRRFGDKLXFRQXLL        NOXA SAHB_C
```

FIG. 2

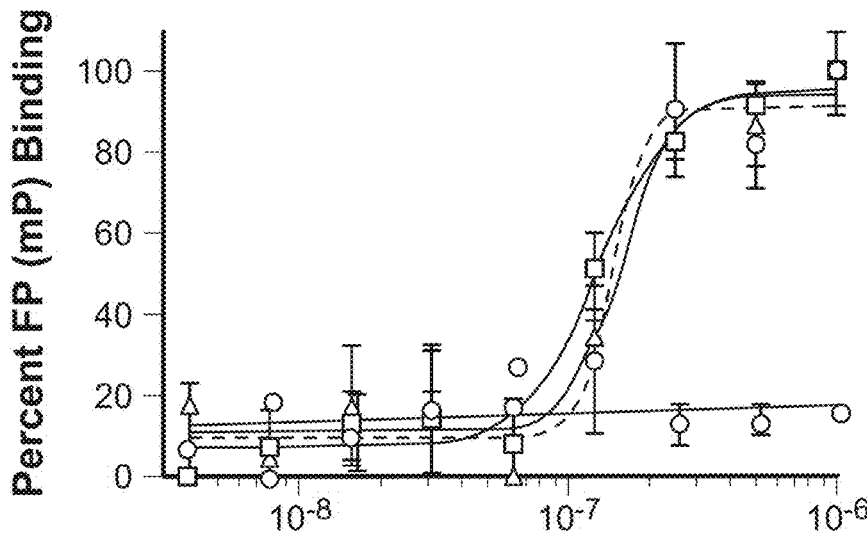

FIG. 3A

NOXA Phe32 panel: (AELEVECATQLRXFGDXLNFRQKLL)

Fmoc-Tle-OH
Fmoc-Val-OH
Fmoc-Nle-OH
Fmoc-His-OH
Fmoc-4-Pal-OH
Fmoc-Phe-OH
Fmoc-Phe(3-I)-OH
Fmoc-Phe(4-I)-OH
Fmoc-Phe(4-CN)-OH
Fmoc-Phe(4-Me)-OH
Fmoc-Phe(4-NO2)-OH
Fmoc-Phe(3,4-Cl2)-OH Fmoc-Phe(2-F)-OH
Fmoc-Phe(3-F)-OH
Fmoc-Phe(4-F)-OH
Fmoc-Phe(3,4-F2)-OH
Fmoc-Phe(F5)-OH
Fmoc-L-homo-Phe-OH
Fmoc-Phe(4-NHBoc)-OH
Fmoc-Phe(4-guanidino-Boc2)-OH
Fmoc-Tyr(Me)-OH
Fmoc-Ala(2-naphthyl)-OH
Fmoc-Bip-OH
Fmoc-Trp-OH

FIG. 3B

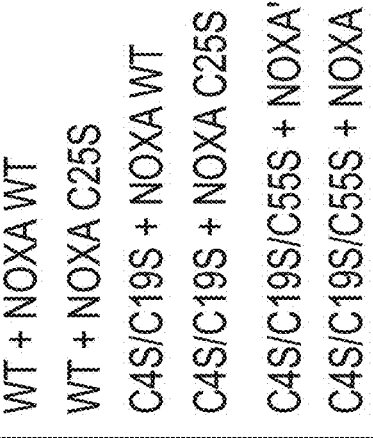
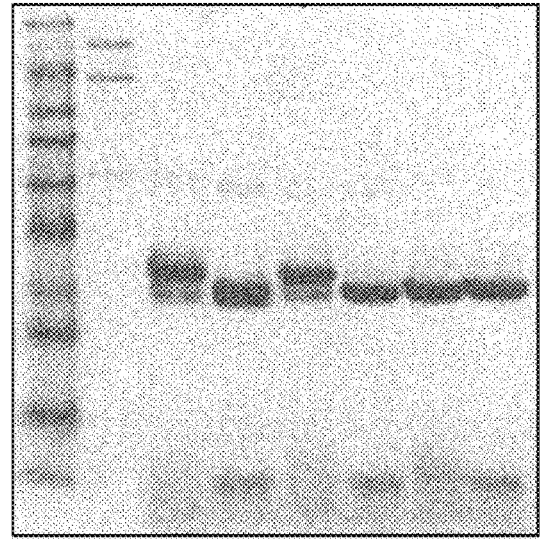
FIG. 4A
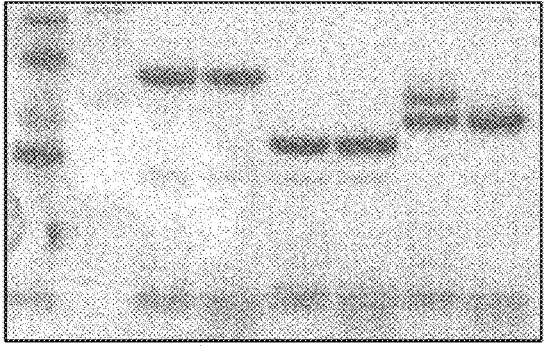
FIG. 4B

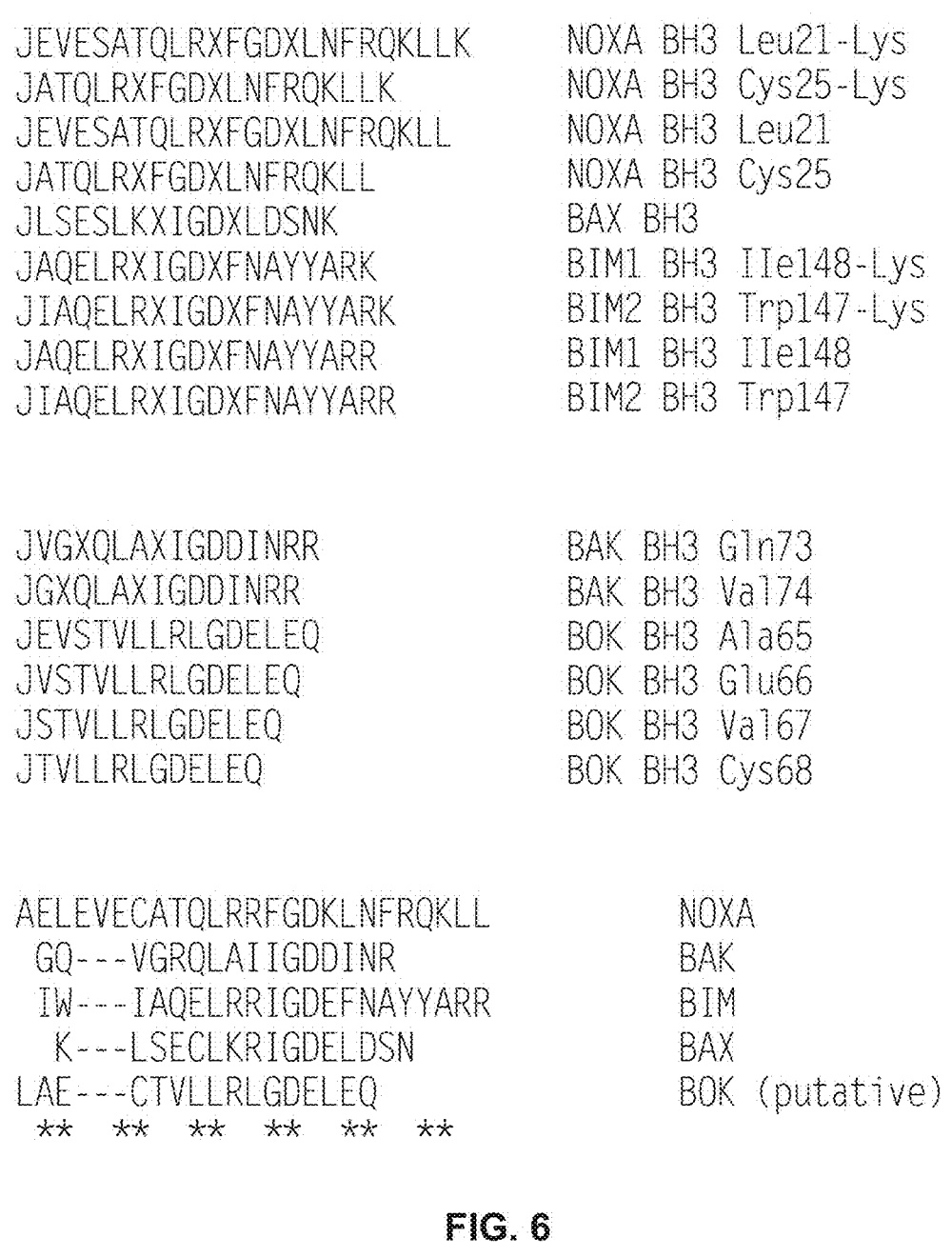

```
JEVESATQLRXFGDXLNFRQKLLK          NOXA BH3 Leu21-Lys
JATQLRXFGDXLNFRQKLLK              NOXA BH3 Cys25-Lys
JEVESATQLRXFGDXLNFRQKLL           NOXA BH3 Leu21
JATQLRXFGDXLNFRQKLL               NOXA BH3 Cys25
JLSESLKXIGDXLDSNK                 BAX BH3
JAQELRXIGDXFNAYYARK               BIM1 BH3 IIe148-Lys
JIAQELRXIGDXFNAYYARK              BIM2 BH3 Trp147-Lys
JAQELRXIGDXFNAYYARR               BIM1 BH3 IIe148
JIAQELRXIGDXFNAYYARR              BIM2 BH3 Trp147

JVGXQLAXIGDDINRR                  BAK BH3 Gln73
JGXQLAXIGDDINRR                   BAK BH3 Val74
JEVSTVLLRLGDELEQ                  BOK BH3 Ala65
JVSTVLLRLGDELEQ                   BOK BH3 Glu66
JSTVLLRLGDELEQ                    BOK BH3 Val67
JTVLLRLGDELEQ                     BOK BH3 Cys68

AELEVECATQLRRFGDKLNFRQKLL         NOXA
 GQ---VGRQLAIIGDDINR              BAK
  IW---IAQELRRIGDEFNAYYARR        BIM
   K---LSECLKRIGDELDSN            BAX
LAE---CTVLLRLGDELEQ               BOK (putative)
             
```

FIG. 6

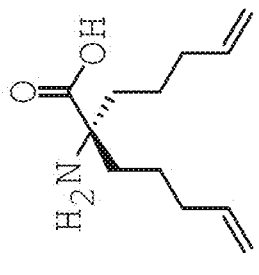
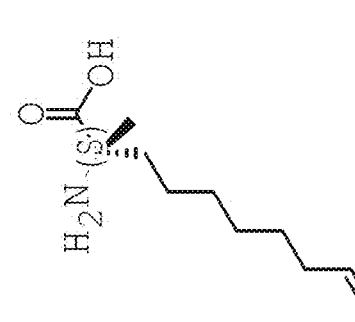
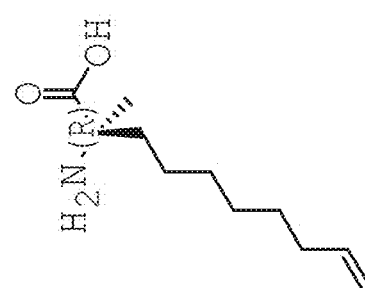
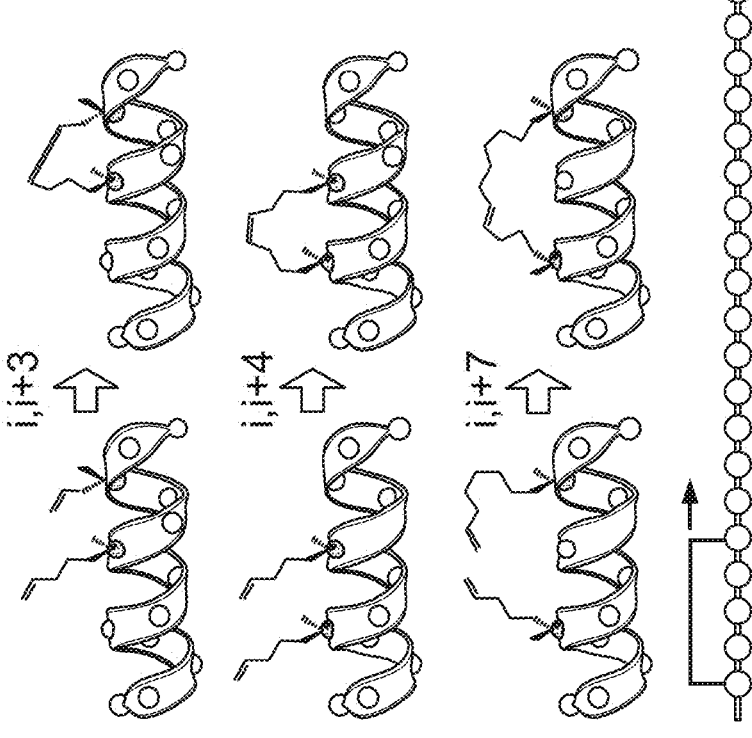
FIG. 7

NOXA BH3

BFL-1ΔC

NOXA SAHB$_A$:          $^{19}$AELEVECATQLRXFGDXLNFRQKLL$^{43}$

NOXA SAHB$_A$ C25S: $^{19}$AELEVESATQLRXFGDXLNFRQKLL$^{43}$

| Protein | SAHB | $K_d$ (nM) |
|---|---|---|
| BFL-1 WT | NOXA WT | 122 |
| BFL-1 C4S/C19S | NOXA WT | 165 |
| BFL-1 C4S/C19S/C55S | NOXA WT | 118 |
| BFL-1 WT | NOXA C25S | 46.6 |
| BFL-1 C4S/C19S | NOXA C25S | 47.2 |
| BFL-1 C4S/C19S/C55S | NOXA C25S | 58.2 |

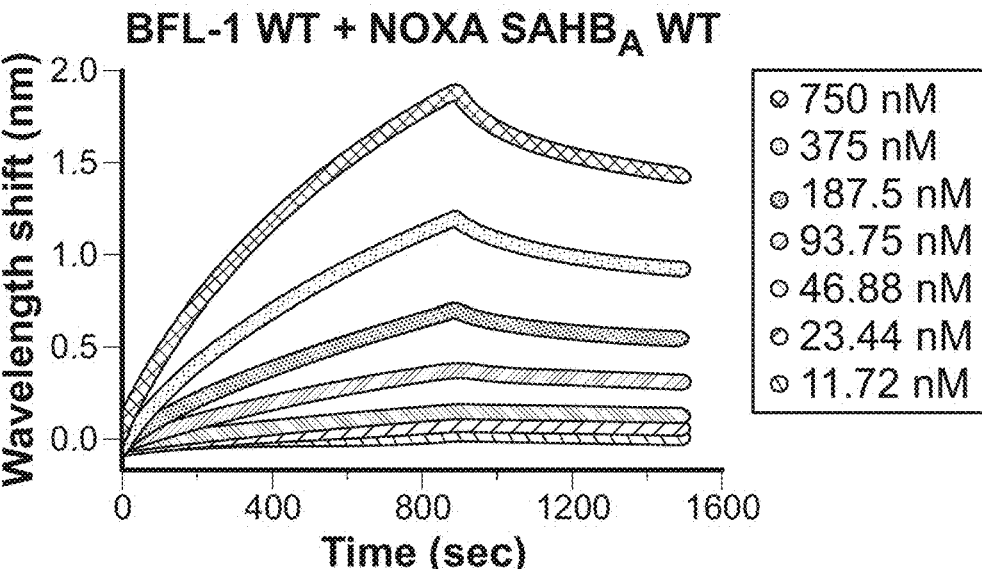
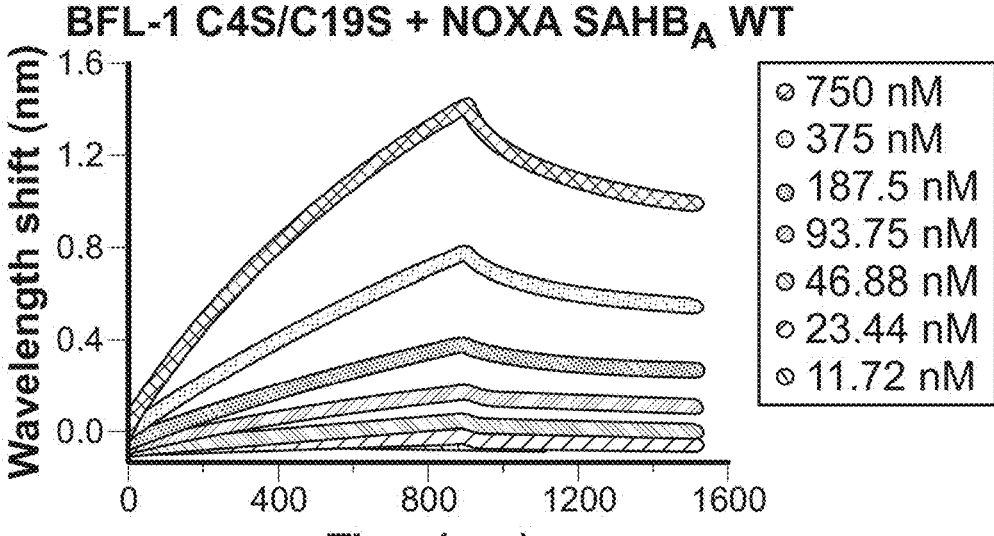
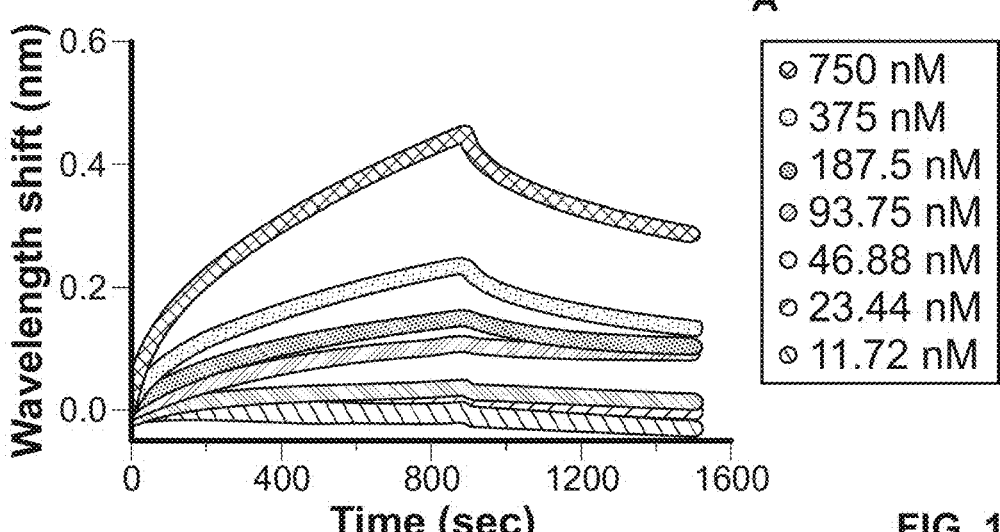
FIG. 11

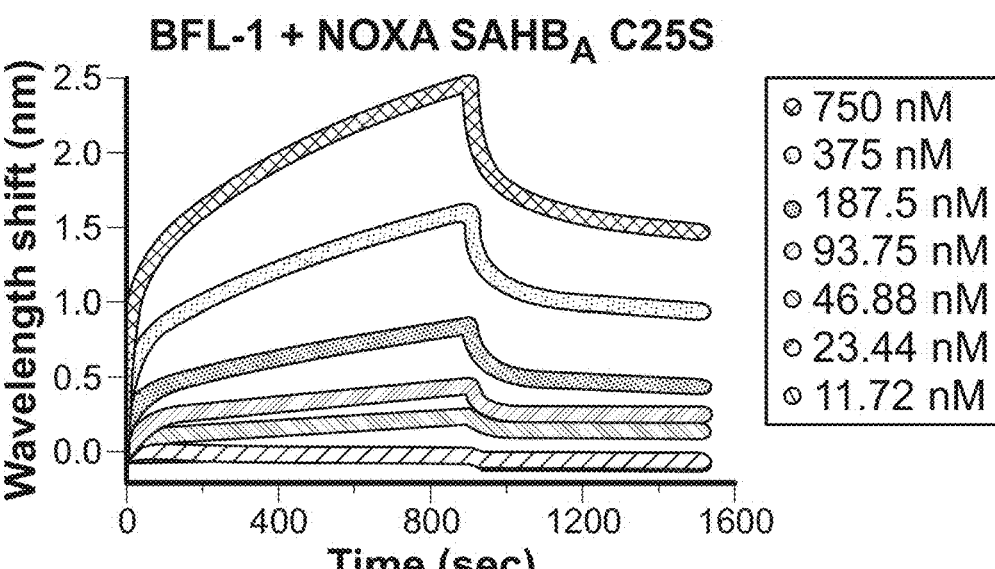
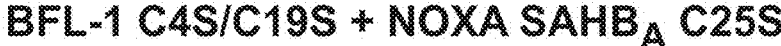
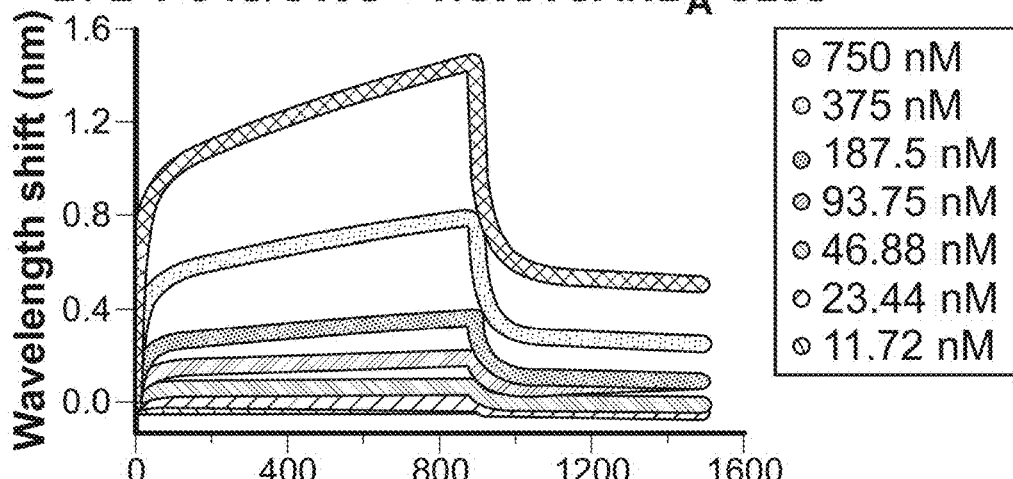
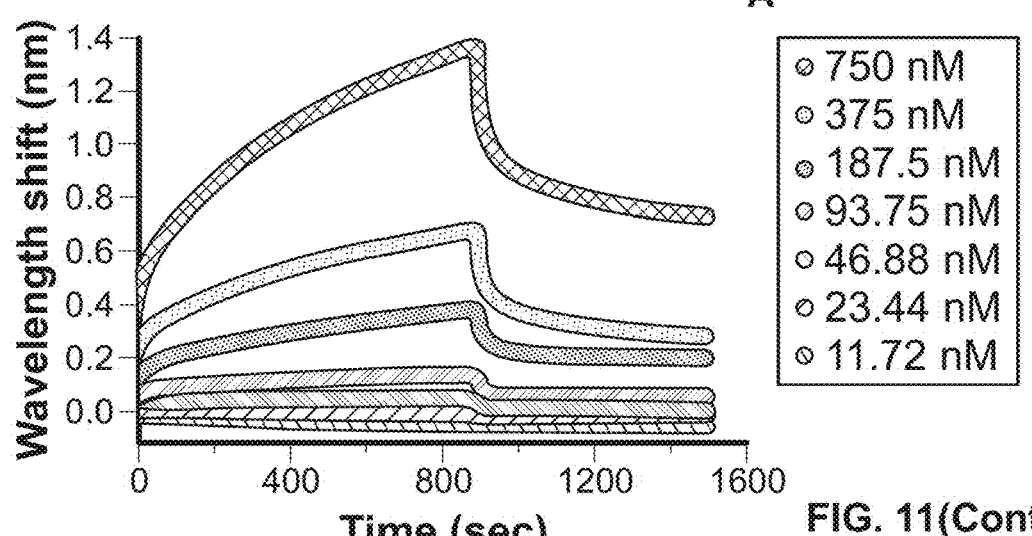
FIG. 11(Cont.)

NOXA SAHB$_A$-WH : $^{21}$JEVESATQLRXFGDXLNFRQKLL$^{43}$
BIM SAHB$_A$-WH : $^{147}$JIAQELRXIGDXFNAYYARR$^{166}$

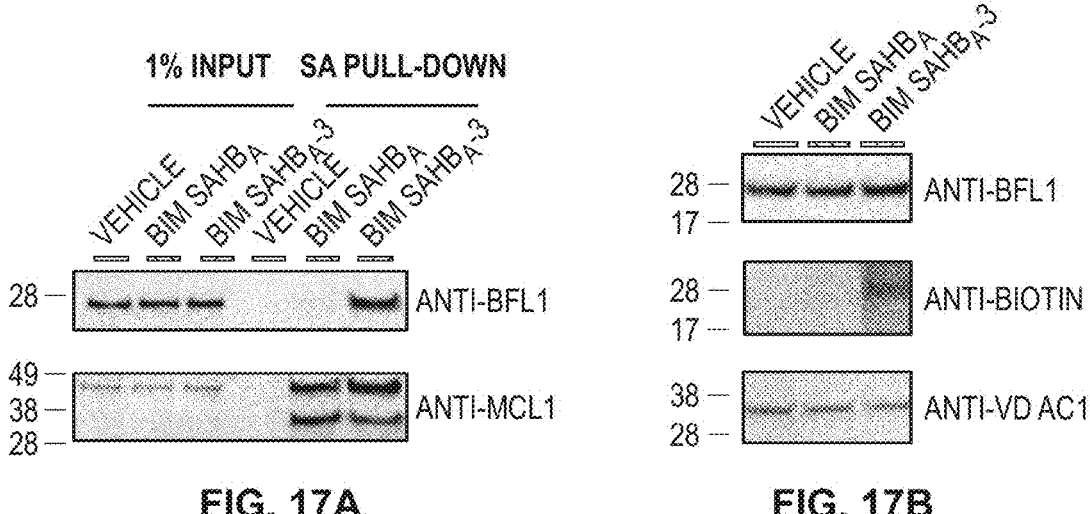
FIG. 17A                    FIG. 17B
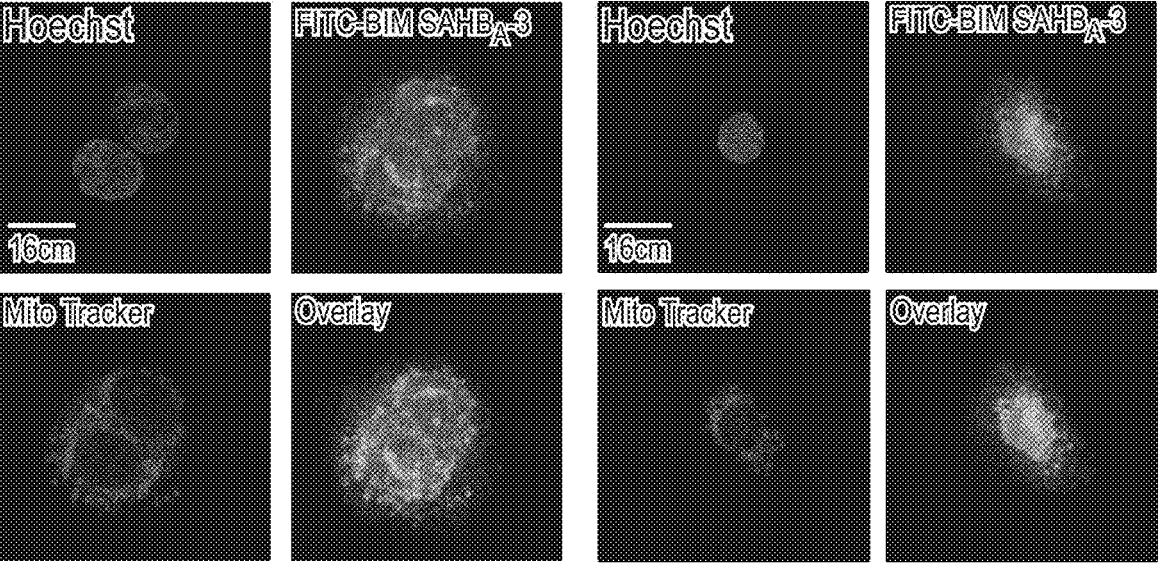
FIG. 17C                    FIG. 17D

| Peptide | N-terminus | Sequence | C-terminus | MW | (M+3)/3 |
|---|---|---|---|---|---|
| NOXA SAHB$_A$ WT (aa 19-43) | FITC-βAla- | AELEVECATQLRXFGDXLNFRQKLL | | 3403.1 | 1135.3 |
| NOXA SAHB$_A$ WT | Btn-PEG-βAla- | AELEVECATQLRXFGDXLNFRQKLL | | 3556.0 | 1186.3 |
| NOXA SAHB$_A$ C25S | FITC-βAla- | AELEVESATQLRXFGDXLNFRQKLL | | 3387.0 | 1130.1 |
| NOXA SAHB$_A$ C25S | Btn-PEG-βAla- | AELEVESATQLRXFGDXLNFRQKLL | | 3539.9 | 1181.1 |
| NOXA SAHB$_A$-1 | 1 | EVESATQLRXFGDXLNFRQKLLK | | 2892.6 | 965.3 |
| NOXA SAHB$_A$-2 | 2 | EVESATQLRXFGDXLNFRQKLLK | | 2906.6 | 970.0 |
| NOXA SAHB$_A$-3 | 3 | EVESATQLRXFGDXLNFRQKLL | | 2778.4 | 927.2 |
| NOXA SAHB$_A$-3 | 3 | EVESATQLRXFGDXLNFRQKLL | Lys(biotin) | 3132.6 | 1045.2 |
| NOXA SAHB$_A$-4 | 4 | EVESATQLRXFGDXLNFRQKLLK | | 2906.6 | 969.9 |
| NOXA SAHB$_A$-5 | 5 | EVESATQLRXFGDXLNFRQKLLK | | 2892.6 | 965.2 |
| NOXA SAHB$_A$-6 | 6 | EVESATQLRXFGDXLNFRQKLLK | | 2892.6 | 965.3 |
| NOXA SAHB$_A$-7 | 7 | EVESATQLRXFGDXLNFRQKLLK | | 2852.5 | 951.8 |
| NOXA SAHB$_A$-8 | 8 | EVESATQLRXFGDXLNFRQKLLK | | 2795.4 | 932.9 |
| NOXA SAHB$_A$ (aa 22-43) | Ac | EVESATQLRXFGDXLNFRQKLL | | 2655.3 | 886.0 |
| NOXA SAHB$_A$ | Ac | EVESATQLRXFGDXLNFRQKLL | Lys(biotin) | 3009.4 | 1004.2 |
| BIM SAHB$_A$-1 | 1 | IAQELRXIGDXFNAYYARK | | 2428.0 | 810.5 |
| BIM SAHB$_A$-2 | 2 | IAQELRXIGDXFNAYYARK | | 2442.0 | 815.0 |
| BIM SAHB$_A$-3 | 3 | IAQELRXIGDXFNAYYARR | | 2469.3 | 824.4 |
| BIM SAHB$_A$-3 | 3 | IAQELRXIGDXFNAYYARR | Lys(biotin) | 2823.5 | 942.3 |
| BIM SAHB$_A$-4 | 4 | IAQELRXIGDXFNAYYARK | | 2442.0 | 815.0 |
| BIM SAHB$_A$-5 | 5 | IAQELRXIGDXFNAYYARK | | 2428.0 | 810.3 |
| BIM SAHB$_A$-6 | 6 | IAQELRXIGDXFNAYYARK | | 2428.0 | 810.3 |
| BIM SAHB$_A$-7 | 7 | IAQELRXIGDXFNAYYARK | | 2388.0 | 797.1 |
| BIM SAHB$_A$-8 | 8 | IAQELRXIGDXFNAYYARK | | 2330.9 | 778.0 |
| BIM SAHB$_A$ (aa 146-166) | Ac | IAQELRXIGDXFNAYYARR | | 2346.9 | 783.3 |
| BIM SAHB$_A$ | Ac | IAQELRXIGDXFNAYYARR | Lys(biotin) | 2701.1 | 901.4 |
| BIM SAHB$_{A1}$ (aa 146-166) | FITC-βAla- | IWIAQELRXIGDXFNAYYARR | | 3064.3 | 1022.4 |
| BIM SAHB$_A$-3 | FITC-Cyste-3- | IAQELRXIGDXFNAYYARR | | 2935.5 | 979.8 |
| BIM SAHB$_{A1}$ (aa 146-166) | Ac | IWIAQELRXIGDXFNAYYARR | | 2646.3 | 883.1 |

1:(S)-1-acryloylpyrrolidine-3-carboxamide; 2:1-acryloylpiperidine-4-carboxamide;
3:(R)-1 acryloylpiperidine-3-carboxamide; 4:(S)-1-acryloylpiperidine-3-carboxamide;
5:(S)-1-acryloylpyrrolidine-2-carboxamide; 6:(R)-1 acryloylpyrrolidine-2-carboxamide;
7:(E)-4-(dimethylamino)but-2-enamide; 8:acrylamide; FITC-Cyste: FITC-cysteamine.

FIG. 18

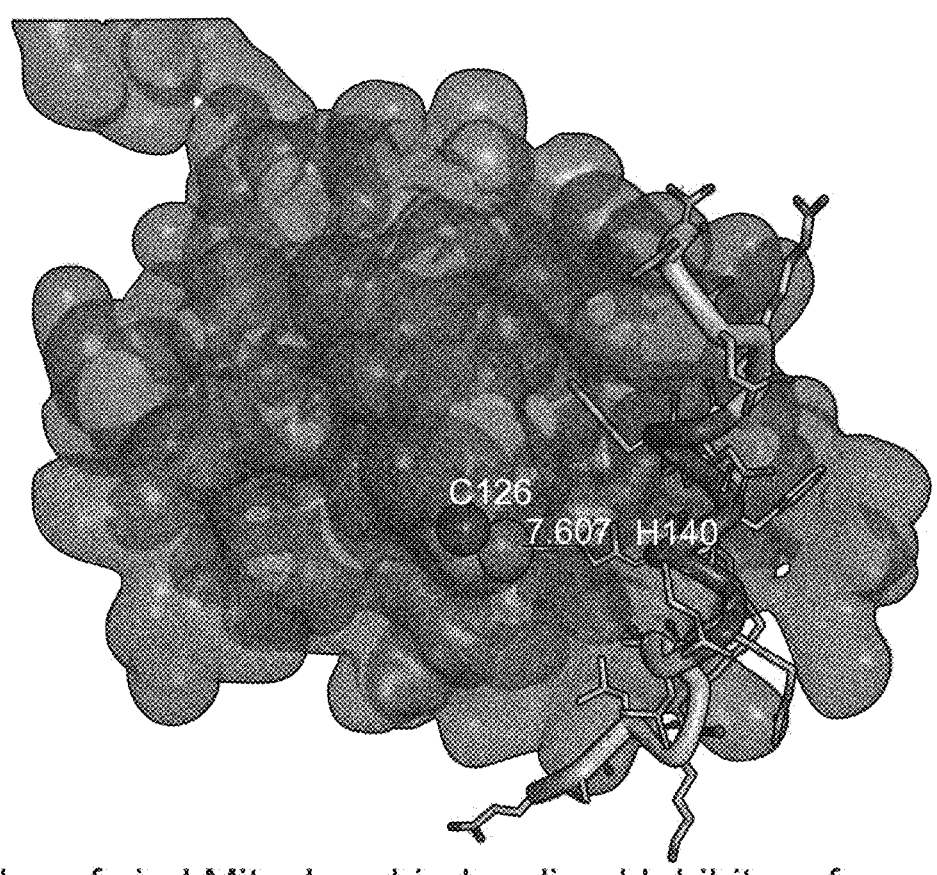

Peptides of viral Mitochondria-localized Inhibitor of Apoptosis (vMIA) of
Cytomegalovirus for covalent modulation of BAX:

CEALKKALRRHRFLWQRRQRA        (SEQ ID NO: 9)
EALKKJLRRHRFLWQRRQRA         (SEQ ID NO: 10)
EALKKALRRJRFLWQRRQRA         (SEQ ID NO: 11)
EALKKALRRHRFLJQRRQRA         (SEQ ID NO: 12)
LKXJLRXHRFLWQR                 (SEQ ID NO: 13)
LKXALRXJRFLWQR                 (SEQ ID NO: 14)
LKXALRXHRFLJQR                 (SEQ ID NO: 15)
LKKJLRRHXFLWXR                 (SEQ ID NO: 16)
LKKALRRJXFLWXR                 (SEQ ID NO: 17)
LKKALRRHXFLJXR                 (SEQ ID NO: 18)
L8KJLRRHXFLWQR                 (SEQ ID NO: 19)
L8KALRRJXFLWQR                 (SEQ ID NO: 20)
L8KALRRHXFLJQR                 (SEQ ID NO: 21)

FIG. 19

Stapled eiF4G peptides for covalent modulation of eiF4E:

KKRYSRLQLLLLX     (SEQ ID NO: 22)
KKRYSJLQLLLLX     (SEQ ID NO: 23)

Stapled Mediator of RNA polymerase II transcription subunit 11 peptides for covalent modulation of Mediator of RNA polymerase II transcription subunit 22:

GSHMINVNKKALGQDTEKMEEQLDLLSAILDPSKSKDGAGS    (SEQ ID NO: 24)

| Sequence | SEQ ID |
|---|---|
| Q8TEKMEEXLDLJSAILD | (SEQ ID NO: 24) |
| Q8TEKMEEXLDLLSAIJD | (SEQ ID NO: 25) |
| XDTEKMEEQLDLJSAILD | (SEQ ID NO: 26) |
| XDTEXMEEQLDLLSAIJD | (SEQ ID NO: 27) |
| QDTE8MEEQLDXJSAILD | (SEQ ID NO: 28) |
| QDTE8MEEQLDXLSAIJD | (SEQ ID NO: 29) |
| QDTEXMEEXLDLJSAILD | (SEQ ID NO: 30) |
| QDTEXMEEXLDLLSAIJD | (SEQ ID NO: 31) |
| QDTEKM8EQLDLJXAILD | (SEQ ID NO: 32) |
| QDTEKM8EQLDLLXAIJD | (SEQ ID NO: 33) |

FIG. 21

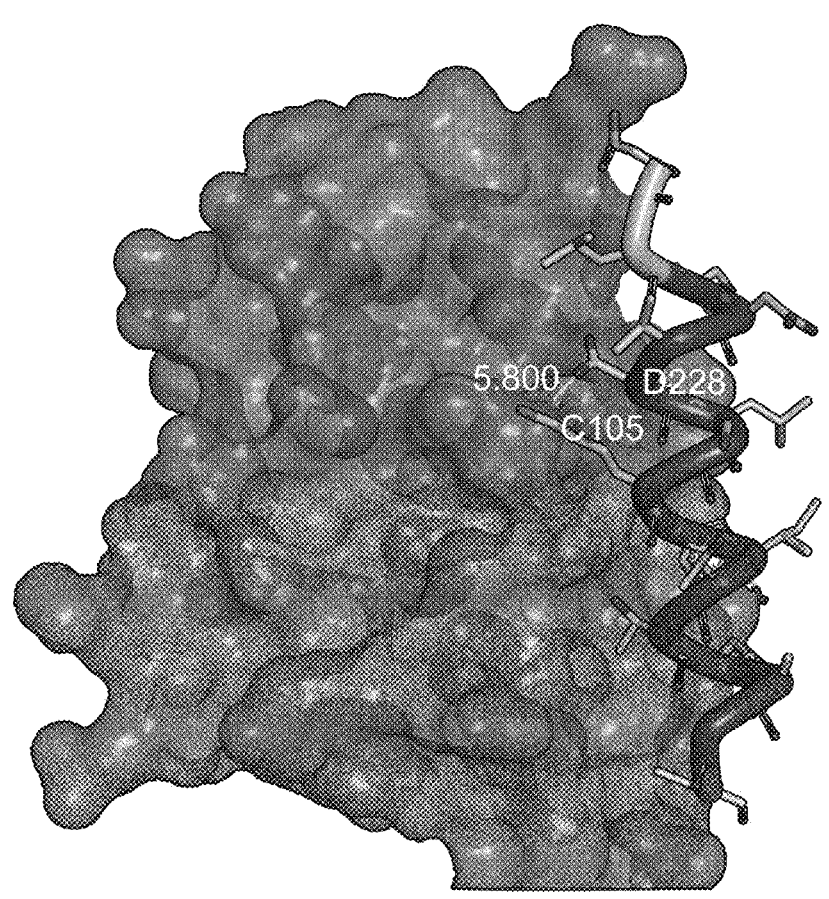

Stapled FAS ligand peptides for covalent modulation of FADD:

NLSDVDLSKYITTIAGVMTLSQVKGFVRKNG        (SEQ ID NO:34)

NJSXVDLXKYITTIAGVMTLSQVKGFV        (SEQ ID NO:35)

NLSXVJLXKYITTIAGVMTLSQVKGFV        (SEQ ID NO:36)

NLSXVDLXJYITTIAGVMTLSQVKGFV        (SEQ ID NO:37)

NJSDVDLXKYIXTIAGVMTLSQVKGFV        (SEQ ID NO:38)

NLSDVJLXKYIXTIAGVMTLSQVKGFV        (SEQ ID NO:39)

NLSDVDLXJYIXTIAGVMTLSQVKGFV        (SEQ ID NO:40)

8JSDVDLXKYITTIAGVMTLSQVKGFV        (SEQ ID NO:41)

8LSDVJLXKYITTIAGVMTLSQVKGFV        (SEQ ID NO:42)

8LSDVDLXJYITTIAGVMTLSQVKGFV        (SEQ ID NO:43)

NJSDV8LSKYITXIAGVMTLSQVKGFV        (SEQ ID NO:44)

NLSDV8LSJYITXIAGVMTLSQVKGFV        (SEQ ID NO:45 )

FIG. 22

Stapled Netrin receptor DCC peptides for covalent modulation of Myosin-X:

LSEQMASLEGLMKQLNAITGSAF          (SEQ ID NO:46)

QMA8LEGLMKXLNAITJ               (SEQ ID NO:47)

QMASLXGLMXQLNAITJ               (SEQ ID NO:48)

QMASLEXLMKXLNAITJ               (SEQ ID NO:49)

Stapled elF4A peptides for covalent modulation of PDCD4:

| | |
|---|---|
| IFINTRRKVDWLTEKMHARDFTVSAMHGD | (SEQ ID NO:50) |
| JRRKV8WLTEKMXAR | (SEQ ID NO:51) |
| JRRKVDWLTEKMHAR | (SEQ ID NO:52) |
| J8RKVDWLXEKMHAR | (SEQ ID NO:53) |
| JRRKVDWL8EKMHARX | (SEQ ID NO:54) |
| JRRKVDWLTEXMHAX | (SEQ ID NO:55) |
| JRR8VDWLTEXMHAR | (SEQ ID NO:56) |

Stapled RASSF1 peptides for covalent modulation of DAXX:

GSQEDSDSELEQYFTARW          (SEQ ID NO:57)

JDSELEQYFTARW               (SEQ ID NO:58)

JDXELEXYFTARW               (SEQ ID NO:59)

JD8ELEQYFXARW               (SEQ ID NO:60)

JDSELEQYFTARW               (SEQ ID NO:61)

Stapled p53 peptides for covalent modulation of p300:

MEEPQSDPSVEPPLSQETFSDLWKLLPENNVLSPLPSQA     (SEQ ID NO:62)

LSQETFSDLWKLLJ                (SEQ ID NO:63)

LSXETFXDLWKLLJ                (SEQ ID NO:64)

LS8ETFSDLXKLLJ                (SEQ ID NO:65)

LSQETFXDLWXLLJ                (SEQ ID NO:66)

LSQETFSXLWKXLJ                (SEQ ID NO:67)

Stapled peptides for covalent modulation and dimer
disruption of tryptophanyl-tRNA synthetase:

GMSSGFYKNVVKIQKHVTFNQVKGIF      (SEQ ID NO:68)

FYKNVVKIQJHVTFN      (SEQ ID NO:69)

FYKNVVK8QJHVTFX      (SEQ ID NO:70)

FYK8VVKIQJXVTFN      (SEQ ID NO:71)

F8KNVVKIXJHVTFN      (SEQ ID NO:72)

FYKNVVKIXJHVXFN      (SEQ ID NO:73)

FYKNVVKIQJXVTFX      (SEQ ID NO:74)

FYKNVVXIQJXVTFN      (SEQ ID NO:75)

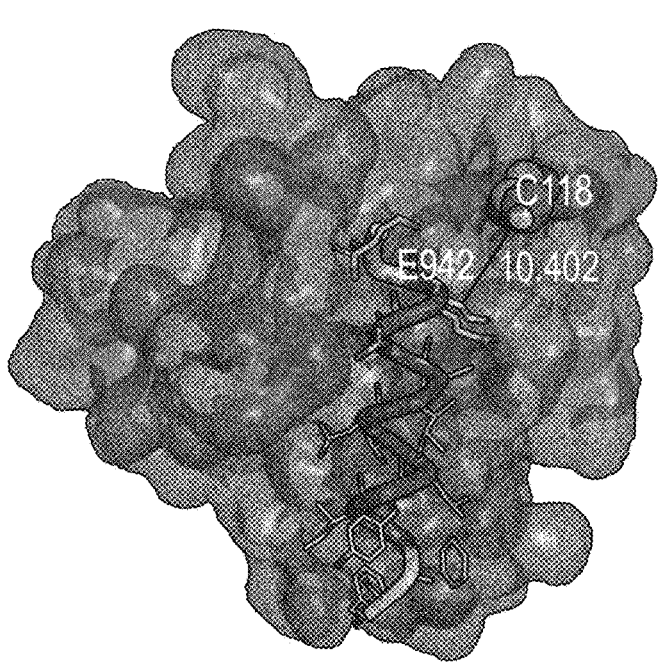

Stapled SOS peptides for covalent modulation of RAS: 1bkd_RAS-SOS C118

| | |
|---|---|
| XFGIXLTNILKTEJGN | (SEQ ID NO:76) |
| FXGIYXTNILKTEJGN | (SEQ ID NO:77) |
| FFXIYLXNILKTEJGN | (SEQ ID NO:78) |
| FFGXYLTXILKTEJGN | (SEQ ID NO:79) |
| FFGIXLTNXLKTEJGN | (SEQ ID NO:80) |
| FFGIYXTNIXKTEJGN | (SEQ ID NO:81) |
| FFGIYLXNILXTEJGN | (SEQ ID NO:82) |
| FFGIYLTXILKXEJGN | (SEQ ID NO:83) |
| FFGIYLTNXLKTXJGN | (SEQ ID NO:84) |
| FFGIYLTNILXTEJXN | (SEQ ID NO:85) |
| FFGIYLTNILKXEJGX | (SEQ ID NO:86) |
| FFGIYLTNILKTXJGNX | (SEQ ID NO:87) |
| 8FGIYLTXILKTEJGN | (SEQ ID NO:88) |
| F8GIYLTNXLKTEJGN | (SEQ ID NO:89) |
| FF8IYLTNIXKTEJGN | (SEQ ID NO:90) |
| FFG8YLTNILXTEJGN | (SEQ ID NO:91) |
| FFGI8LTNILKXEJGN | (SEQ ID NO:92) |
| FFGIY8TNILKTXJGN | (SEQ ID NO:93) |
| FFGIYLT8ILKTEJXN | (SEQ ID NO:94) |
| FFGIYLTN8LKTEJGX | (SEQ ID NO:95) |
| FFGIYLTNI8KTEJGNX | (SEQ ID NO:96) |
| FFGIYLTNILKTEJGN | (SEQ ID NO:97) |

FIG. 28

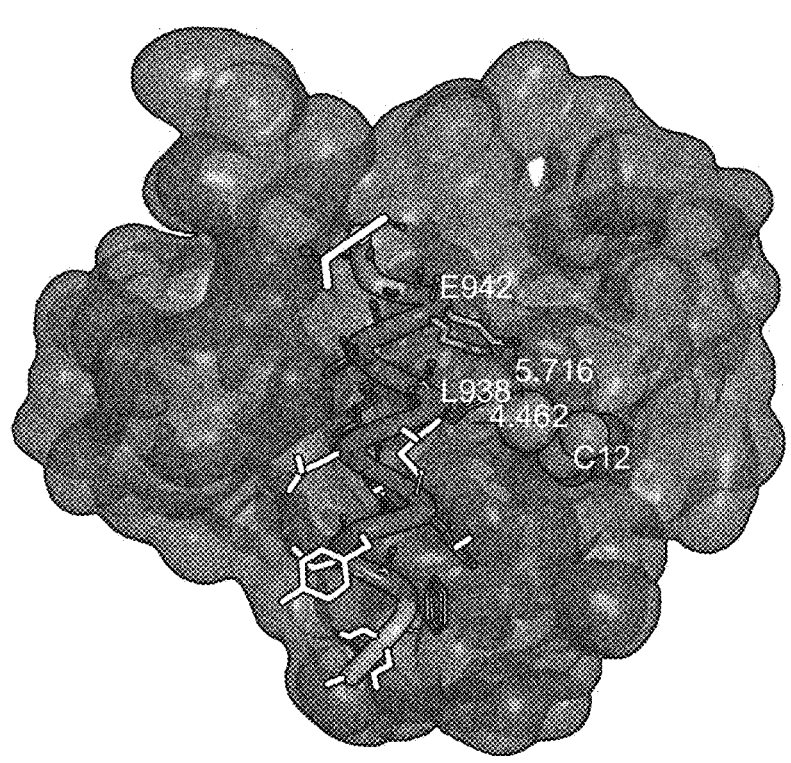

Stapled SOS peptides for covalent modulation of RAS:
1bkd_RAS-SOS G12C

| | |
|---|---|
| XFGIXLTNIJKTEEGN | (SEQ ID NO:98) |
| FXGIYXTNIJKTEEGN | (SEQ ID NO:99) |
| FFXIYLXNIJKTEEGN | (SEQ ID NO:100) |
| FFGXYLTXIJKTEEGN | (SEQ ID NO:101) |
| FFGIXLTNXJKTEEGN | (SEQ ID NO:102) |
| FFGIYLXNIJXTEEGN | (SEQ ID NO:103) |
| FFGIYLTXIJKXEEGN | (SEQ ID NO:104) |
| FFGIYLTNXJKTXEGN | (SEQ ID NO:105) |
| FFGIYLTNIJXTEEXN | (SEQ ID NO:106) |
| FFGIYLTNIJKXEEGX | (SEQ ID NO:107) |
| FFGIYLTNIJKTXEGNX | (SEQ ID NO:108) |
| 8FGIYLTXIJKTEEGN | (SEQ ID NO:109) |
| F8GIYLTNXJKTEEGN | (SEQ ID NO:110) |
| FFG8YLTNIJXTEEGN | (SEQ ID NO:111) |
| FFGI8LTNIJKXEEGN | (SEQ ID NO:112) |
| FFGIY8TNIJKTXEGN | (SEQ ID NO:113) |
| FFGIYL8NIJKTEXGN | (SEQ ID NO:114) |
| FFGIYLT8IJKTEEXN | (SEQ ID NO:115) |
| FFGIYLTN8JKTEEGX | (SEQ ID NO:116) |
| FFGIYLTNIJKTEEGN | (SEQ ID NO:117) |

FIG. 29

STABILIZED PEPTIDES FOR COVALENT BINDING TO TARGET PROTEIN

CROSS-REFERENCE TO RELATED APPLICATIONS

This application is a continuation of U.S. application Ser. No. 17/389,761, filed Jul. 30, 2021, now abandoned, which is a continuation of U.S. application Ser. No. 15/752,372, filed Feb. 13, 2018, now abandoned, which is a U.S. National Stage application and claims priority of International Application No. PCT/US2016/049083, filed Aug. 26, 2016, which claims priority to U.S. Provisional Application No. 62/211,681, filed Aug. 28, 2015, the contents of each of which are incorporated by reference herein in their entirety.

STATEMENT REGARDING FEDERALLY SPONSORED RESEARCH

This invention was made with government support under grant number 1R35CA197583 awarded by the National Institutes of Health. The government has certain rights in the invention.

SEQUENCE LISTING

This application contains a Sequence Listing that has been submitted electronically as an XML file named 00530-0325003_SL_ST26. XML. The XML file, created on May 23, 2024, is 320,221 bytes in size. The material in the XML text file is hereby incorporated by reference in its entirety.

TECHNICAL FIELD

This disclosure relates to structurally stabilized peptides that can covalently bind to a cysteine residue in a target protein and modulate (e.g., inhibit, activate) the target protein's activity and a platform technology for making same.

BACKGROUND

Hydrocarbon stapled alpha helical peptides are widely used to modify the activity of target protein with which they interact. Several such peptides are undergoing clinical trials. However, as with all drugs, stapled peptides would benefit from modifications that improved their binding affinity, binding selectivity, and/or therapeutic window.

SUMMARY

Variant hydrocarbon stapled peptides bearing an electrophilic group that can covalently bind to a cysteine residue in target protein are described. By combining the proven ability of stapled peptides to disrupt intracellular protein-protein interactions, or directly activate or modulate a target protein, with the pharmacologic enhancements inherent to covalent drugs, novel chimeric peptides have been created.

Challenges in small molecule drug development are similar for developing prototype stapled peptides. First, achieving sufficiently high potency and selectivity can be challenging for both small molecules and stapled peptides because there is a limit to the binding affinity that can be attained for ligand of any size or shape or surface area. Modification of a small molecule to permit formation of a covalent bond with the target protein allows for a small molecule to achieve extremely high binding affinity and target occupancies that are not possible with any other molecular entity. Additionally, it is recognized that formation of a covalent bond allow for molecules of less size and complexity to be employed, even allowing for the removal of or repurposing of other parts of the molecule towards optimization of other pharmacologic properties, such as stability, bioavailability or cellular internalization. Additionally, covalent inhibitors possess enhanced selectivity for the precise identity and placement of the protein nucleophile. With precisely tuned and placed electrophile, target protein selectivity is exquisite at therapeutic doses. Evidence also exists that resistant mutations arising from treatment with a non-covalent drug are resensitized towards a covalent inhibitor targeting a similar binding pocket. Most compelling though are the favorable pharmacodynamic and cellular localization effects that arise from covalent target inhibition or modulation. Sustained and high level doses are no longer needed to achieve tissue or cellular penetration, as once a covalent drug locates and binds it target, that protein is permanently inhibited, with the aberrant behavior returning only upon additional production of that protein.

Irreversible inhibitors that covalently bind to their target polypeptides have been described. Covalent irreversible inhibitors of drug targets have a number of important advantages over their reversible counterparts as therapeutics. Prolonged suppression of the drug targets may be necessary for maximum pharmacodynamic effect and an irreversible inhibitor can provide this advantage by permanently eliminating existing drug target activity, which will return only when new target polypeptide is synthesized. When an irreversible inhibitor is administered, the therapeutic plasma concentration of the irreversible inhibitor would need to be attained only long enough to briefly expose the target polypeptides to the inhibitor, which would irreversibly suppress activity of the target. Plasma levels could then rapidly decline while the target polypeptide would remain inactivated. This has the potential advantage of lowering the minimal plasma concentration at which therapeutic activity occurs, minimizing multiple dosing requirements and eliminating the requirement for long plasma half-lives without compromising efficacy. All of these considerations could reduce toxicity due to any nonspecific off target interactions that may occur at high or prolonged plasma levels. Irreversible inhibitors would also likely have advantages in overcoming drug resistance.

The variant peptides described herein form a covalent bond with a cysteine residue in the binding site of the target polypeptide when the variant peptide is bound to the binding site. A covalent bond length of less than about 2 angstroms for the bond formed between the sulfur atom of the Cys residue in the binding site and the reactive chemical functionality of the warhead is preferable.

In one aspect, the disclosure provides a method for identifying an amino acid in a polypeptide for substitution to facilitate covalent binding to a protein that the polypeptide binds to. The alpha carbon of the amino acid for substitution is about 0.1 $A^O$ to about 15 $A^O$ (e.g., 0.1, 0.5, 1, 2, 3, 4, 5, 6, 7, 8, 9, 10, 11, 12, 13, 14, or 15 $A^O$, or between 1 and 10, between 1 and 9, between 1 and 8, between 3 and 10, between 3 and 9, between 3 and 8, between 4 and 10, between 4 and 9, between 4 and 8 $A^O$), from the sulfhydryl group of a cysteine residue in the interacting region of the protein. The amino acid at the stated distance range is substituted with a non-natural amino acid, or other chemical matter linked to the stapled peptide, comprising an electrophilic group (e.g., (S)-1-acryloylpyrrolidine-3-carboxamide; 1-acryloylpiperidine-4-carboxamide, (R)-1-acryloylpiperidine-3-carboxamide; (S)-1-acryloylpiperidine-3-carboxamide; (S)-1-acryloylpyrrolidine-2-carboxamide; (R)-1-acry-loylpyrrolidine-2-carboxamide; (E)-4-(dimethylamino)but-2-enamide; and acrylamide). In some instances, the method involves substituting multiple locations so as to achieve the ideal angle of approach or orientation of the electrophile which combined with the precise placement of the electro-phile will facilitate the formation of the covalent bond. In some instances, the polypeptide is 100, 75, 60, 50, 40, 30, 29, 28, 27, 26, 25, 24, 23, 22, 21, 20, 19, 18, 17, 16, 15, 14, 13, 12, 11, 10, 9, 8, 7, 6, or 5 amino acids in length. In certain instances, the polypeptide is between 8 and 40 amino acids in length. In some embodiments, the polypeptide comprises at least two non-natural amino acids with olefinic side chains (e.g., S-pentenyl alanine). In certain embodiments, at least two non-natural amino acids with olefinic side chains can be different from one another. In some embodiments, the poly-peptide comprises a stabilized alpha helix (e.g., stabilized by stapling, stitching, or a combination thereof). In a particular embodiment, the protein is a member of the anti-apoptotic BCL2 family of proteins (e.g., Bcl-2, Bcl-XL, Bcl-w; MCL-1, BFL-1, and BCL-B) and the stabilized polypeptide com-prises the BH3 domain of NOXA, BIM, BID, BAK, BOK, BAX, or PUMA.

In another aspect, the disclosure provides a method of using bioinformatics or a structural database searching tool or program which is capable of searching the protein struc-ture database for identifying structures that have an amino residue of an alpha helix of one chain or protein adjacent (e.g., 1-10 Angstroms) to a cysteine on a separate chain or protein. These methods can be incorporated into the methods for modifying the alpha helix to incorporate an electrophile-containing moiety at the position that is adjacent to the cysteine on the other chain or protein so as to covalently target that chain or protein.

In another aspect, the disclosure provides a method for identifying a position/location of an amino acid in a poly-peptide that can be modified to facilitate covalent binding to a protein that the polypeptide binds to. The alpha carbon of the amino acid for modification is about 0.1 $A^0$ to about 15 $A^0$ (e.g., 0.1, 0.5, 1, 2, 3, 4, 5, 6, 7, 8, 9, 10, 11, 12, 13, 14, or 15 $A^0$, or between 1 and 10, between 1 and 9, between 1 and 8, between 3 and 10, between 3 and 9, between 3 and 8, between 4 and 10, between 4 and 9, between 4 and 8 $A^0$), from the sulfhydryl group of a cysteine residue in the interacting region of the protein. The amino acid at the stated distance range is modified by appending a chemical moiety comprising an electrophilic group. In certain cases, the position of the amino acid is at the N-terminus of the polypeptide. In other instances, the position of the amino acid is at the C-terminus of the polypeptide. In certain embodiments, the electrophilic group comprising entity is e.g., (S)-1-acryloylpyrrolidine-3-carboxamide; 1-acry-loylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino) but-2-enamide; or acrylamide. In some instances, the polypeptide is 100, 75, 60, 50, 40, 30, 29, 28, 27, 26, 25, 24, 23, 22, 21, 20, 19, 18, 17, 16, 15, 14, 13, 12, 11, 10, 9, 8, 7, 6, or 5 amino acids in length. In certain instances, the polypeptide is between 5 and 40 amino acids in length. In certain instances, the polypeptide is between 8 and 30 amino acids in length. In some embodiments, the polypeptide comprises at least two non-natural amino acids with olefinic side chains (e.g., S-pentenyl alanine). In certain embodi-ments, at least two non-natural amino acids with olefinic side chains can be different from one another. In some embodiments, the polypeptide comprises a stabilized alpha helix (e.g., stabilized by stapling, stitching, or a combination thereof). In a particular embodiment, the protein is a mem-ber of the anti-apoptotic BCL2 family of proteins (e.g., Bcl-2, Bcl-xL, Bcl-w; MCL-1, BFL-1, and BCL-B) and the stabilized polypeptide comprises the BH3 domain of NOXA, BIM, BID, BAK, BOK, BAX, or PUMA.

In another aspect, the disclosure provides a method for covalently modifying a target protein with a polypeptide (e.g., a stabilized alpha-helix containing polypeptide). The polypeptide is modified to include at least two non-natural amino acids with olefinic side chains and a non-natural amino acid, or other chemical matter linked to the stapled peptide, comprising an electrophilic group. In certain embodiments, the polypeptide comprises three substituted amino acids (e.g., substituted with non-natural amino acids). In another embodiment, the polypeptide comprises two substituted amino acids (e.g., substituted with non-natural amino acids) and electrophile containing entity linked to the peptide. In certain embodiments, one of the amino acids of the polypeptide that is substituted with a moiety that com-prises an electrophilic group (or the electrophile containing entity linked to the peptide) is about 0.1 $A^0$ to about 15 $A^0$ (e.g., 0.1, 0.5, 1, 2, 3, 4, 5, 6, 7, 8, 9, 10, 11, 12, 13, 14, or 15 $A^0$, or between 1 and 10, between 1 and 9, between 1 and 8, between 3 and 10, between 3 and 9, between 3 and 8, between 4 and 10, between 4 and 9, between 4 and 8 $A^0$), from a cysteine residue in the interacting region of the protein. The amino acid at the stated distance range is substituted with a non-natural amino acid or other chemical entity linked to the stapled peptide comprising an electro-philic group (e.g., (S)-1-acryloylpyrrolidine-3-carboxamide; 1-acryloylpiperidine-4-carboxamide, (R)-1 acryloylpiperi-dine-3-carboxamide; (S)-1-acryloylpiperidine-3-carboxam-ide; (S)-1-acryloylpyrrolidine-2-carboxamide; (R)-1-acry-loylpyrrolidine-2-carboxamide; (E)-4-(dimethylamino) but-2-enamide; and acrylamide). In certain cases, the electrophile that is at the stated distance range is not linked to an amino acid. For example, the electrophilic moiety and peptide would be linked via a nitrogen containing hetero-cycle, either saturated (aziridine, diaziridine, azetidine, pyr-rolidine, imidazolidine, pyrazolidine, oxazolidine, isoxazo-lidine, thiazolidine, isothiazolidine, piperidine, piperazine, morpholine, thiomorpholine, azepane) or unsaturated (azirine, diazirine, azete, pyrrole, imidazole, pyrazole, oxa-zole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphtha-lene, anthracene, phenanthrene, indole, isoindole, indoliz-ine, quinolone, isoquinoline, quinoxaline, phthalazine, qui-nazoline, purine, carbazole, indazole, benzimidazole, azaindole. The electrophilic warhead in some embodiments is an acrylamide, or more generally defined as an $\alpha,\beta$-unsaturated carbonyl, such as $\alpha$-cyanoacrylamide, propiol-amide, trans 4-dimethylamino-2-butenamide, or trans 4-pi-peridinyl-2-butenamide, or any other substituted acrylamide. In some instances, the polypeptide is 100, 75, 60, 50, 40, 30, 29, 28, 27, 26, 25, 24, 23, 22, 21, 20, 19, 18, 17, 16, 15, 14, 13, 12, 11, 10, 9, 8, 7, 6, 5, or 4 amino acids in length. In certain instances, the polypeptide is between 4 and 40 amino acids in length. In some embodiments, the polypeptide comprises substitution of at least two amino acids with two non-natural amino acids with olefinic side chains (e.g., S-pentenyl alanine). In certain embodiments, at least two non-natural amino acids with olefinic side chains can be different from one another. In some embodiments, the polypeptide comprises a stabilized alpha helix (e.g., stabilized by stapling, stitching, or a combination thereof). In a particular embodiment, the protein is a member of the anti-apoptotic BCL2 family of proteins (e.g., Bcl-2, Bcl-xL, Bcl-w, MCL-1, BFL-1, and BCL-B) and the stabilized polypeptide comprises the BH3 domain of NOXA, BIM, BID, BAK, BOK, BAX, or PUMA.

In certain aspects, the disclosure features a polypeptide comprising an amino acid sequence of at least 4 amino acids in length, but less than 100 amino acids in length that can covalently modify a protein the polypeptide it interacts with. This covalent modification can modulate the activity of the protein (e.g., activate or inhibit the protein). The protein the polypeptide interacts with comprises a cysteine in a region that interacts with the polypeptide. The polypeptide comprises an alpha helix that comprises an interacting region with the protein, and the alpha helix of the polypeptide comprises at least two non-natural amino acids with olefinic side chains and a non-natural amino acid, or other chemical matter linked to the stapled peptide, comprising an electrophilic group. The non-natural amino acid, or appended chemical moiety, comprising the electrophilic group can covalently bond with the cysteine in the protein. In some embodiments, the polypeptide is 100, 75, 60, 50, 40, 30, 29, 28, 27, 26, 25, 24, 23, 22, 21, 20, 19, 18, 17, 16, 15, 14, 13, 12, 11, 10, 9, 8, 7, 6, 5, or 4 amino acids in length. In certain cases, the polypeptide is between 4 and 40 amino acids in length. In some embodiments, the polypeptide comprises a stabilized alpha helix (e.g., through stapling, stitching or a combination of the two). In some embodiments, the protein is a member of the anti-apoptotic BCL2 family of proteins (e.g., Bcl-2, Bcl-xL, Bcl-w; MCL-1, BFL-1, and BCL-B) and the stabilized polypeptide comprises the BH3 domain of NOXA, BIM, BID, BAK, BOK, BAX, or PUMA. The non-natural amino acid comprising an electrophilic group can be, e.g., (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino)but-2-enamide; or acrylamide. In some embodiments, the at least two non-natural amino acids with olefinic side chains are S-pentenyl alanine. In certain embodiments, the at least two non-natural amino acids with olefinic side chains are different from one another.

In another aspect, the disclosure features exemplary stabilized peptides that can be used for covalent targeting (or modulation, such as inhibition or activation) of their respective target proteins. In certain instances, the polypeptides of this disclosure comprise or consist of a stabilized peptide that is at least 40%, 45%, 50%, 55%, 60%, 65%, 70%, 75%, 80%, 85%, 90%, 95%, 97% or 100% identical to the interacting alpha-helical face of an amino acid sequence provided in any one of SEQ ID NOs.: 9-117. The "interacting face" of the polypeptides described herein includes those amino acid residues of the alpha helix that interact (e.g., interact specifically or bind specifically) with the target protein that the polypeptide binds. In certain instances, the polypeptides of this disclosure comprise or consist of a stabilized peptide that is provided in any one of SEQ ID NOs.: 9-117. In some embodiments, the polypeptide is 100, 75, 60, 50, 40, 30, 29, 28, 27, 26, 25, 24, 23, 22, 21, 20, 19, 18, 17, 16, 15, 14, 13, 12, 11, 10, 9, 8, 7, 6, 5 or 4 amino acids in length. In some cases, the polypeptide is 4 to 40 amino acids in length. In certain cases, the polypeptide is between 4 and 40 amino acids in length. In some embodiments, the polypeptide comprises a stabilized alpha helix (e.g., through stapling, stitching or a combination of the two). The disclosure features pharmaceutical composition comprising a stabilized peptide selected from SEQ ID NOs.: 9-117. In certain embodiments, the polypeptide comprises a non-natural amino acid comprising an electrophilic group that can be, e.g., (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino) but-2-enamide; or acrylamide. In certain cases, the electrophile is not linked to an amino acid. For example, the electrophilic moiety and peptide would be linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalazine, quinazoline, purine, carbazole, indazole, benzimidazole, azaindole. The electrophilic warhead in some embodiments is an acrylamide, or more generally defined as an $\alpha,\beta$-unsaturated carbonyl, such as $\alpha$-cyanoacrylamide, propiolamide, trans 4-dimethylamino-2-butenamide, or trans 4-piperidinyl-2-butenamide, or any other substituted acrylamide.

In another aspect, the disclosure relates to a stabilized polypeptide of 5 to 40 amino acids in length that specifically binds a target protein. The stabilized polypeptide comprises at least two non-natural amino acids with olefinic side chains. The stabilized polypeptide's backbone is linked to an electrophilic acrylamide or substituted acrylamide. The linker is a nitrogen containing heterocycle, nitrogen containing heterocyclic amino acid, or amino-functionalized benzene ring, carbocycle, polycycle or heterocycle. In some embodiments, the at least two non-natural amino acids with olefinic side chains are both S-pentenyl alanine. In other embodiments, the at least two non-natural amino acids with olefinic side chains are different non-natural amino acids. In a specific embodiment, the target protein is a member of the anti-apoptotic BCL2 family of proteins (e.g., Bcl-2, Bcl-xL, Bcl-w; MCL-1, BFL-1, and BCL-B).

In a further aspect, the disclosure features an electrophilic acrylamide or substituted acrylamide linked to a stabilized polypeptide backbone via a linker. The linker can be, e.g., a nitrogen containing heterocycle, a nitrogen containing heterocyclic amino acid, an amino-functionalized benzene ring, an amino-functionalized carbocycle, an amino-functionalized polycycle, or an amino-functionalized heterocycle.

In some aspects, the present disclosure provides internally cross-linked polypeptides comprising the amino acid sequence of all or a portion of an alpha helical domain of a protein (e.g. a BH3 domain of an apoptotic protein), wherein:

the side chains of two amino acids separated by two, three or six amino acids are replaced by an internal staple; the side chains of three amino acids are replaced by internal stitch; the side chains of four amino acids are replaced by two internal staples, the side chains of five amino acids are replaced by the combination of a stitch and a staple, or the sides chains of six amino acids are replaced by two stiches or two staples; and the side chain of one amino acid is replaced by an electrophilic group that can covalently react with the side chain of a cysteine.

In some embodiments, internally cross-linked peptides are selected from the group consisting of SEQ ID NOs: 1-117. In some embodiments, the internal staples and/or the internal stitch comprises at least two internal staples (replacing the side chains of 4 amino acids, i.e., each staple is between two amino acids separated by, for example, 3 amino acids). In some embodiments, the internal staples and/or the internal stitch comprises a combination of at least one internal staple and an internal stitch. In some embodiments, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked polypeptides of the disclosure are selected from the group consisting of SEQ ID NOs: 1-117; the group consisting of SEQ ID NOs: 1-117 and having an amino terminal or carboxy terminal modification; and the group consisting of SEQ ID NOs: 1-117 and having 1, 2, 3, 4, or 5 amino acid substitutions (e.g., 1, 2, 3, 4, or 5 amino acids are conservatively substituted).

In some aspects, the disclosure provides pharmaceutical compositions that include one or more internally cross-linked polypeptides of the disclosure. In some embodiments, such pharmaceutical compositions can also include one or more medicaments for the treatment of cancer.

In some aspects, the disclosure provides methods for treating cancer in a subject. These methods can include selecting a subject suffering from cancer and administering to the subject an effective amount of the stabilized peptides of claims described herein.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctenyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridalyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiuryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), Leu (L), Lys (K), Met (M), Phe (F), Pro (P), Ser(S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclo-propanecarboxylic acid, 1-amino-2-phenyl-cyclopropan-ecarboxylic acid, 1-amino-cyclobutanecarboxylic acid, 4-amino-cyclopentenecarboxylic acid, 3-amino-cyclo-hexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-ami-noheptanedioic acid, 4-(aminomethyl)benzoic acid, 4-ami-nobenzoic acid, ortho-, meta- and para-substituted phenyl-alanines (e.g., substituted with —C(=O)C6H5; —CF3; —CN; -halo; —NO2; CH3), disubstituted phenylalanines, substituted tyrosines (e.g., further substituted with -Q=O) C6H5; —CF3; —CN; -halo; —NO2; CH3), and statine. Additionally, amino acids can be derivatized to include amino acid residues that are hydroxylated, phosphorylated, sulfonated, acylated, and glycosylated, to name a few.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 2: Depicts a number of internally cross-linked NOXA SAHB peptides. X indicates the amino acids whose side chains have been replaced with an internal cross-link. The amino acids shown in this figure have SEQ ID NOs.: 124-136, numbered top to bottom.

FIG. 3A: Depicts the results of studies assessing the binding of various NOXA SAHB peptides to MCL-1 and Bfl-1.

FIG. 3B: Depicts NOXA SAHB peptides with substitution at F32. The amino acid sequence shown in the figure has the amino acid sequence set forth in SEQ ID NO:124.

FIG. 4A: Depicts the results of studies assessing the binding of various NOXA SAHB peptides with and without C25S substitution to Bfl-1.

FIG. 4B: Depicts the results of studies assessing the binding of various NOXA SAHB peptides with and without C25S substitution to Bfl-1, MCL-1 and BCL-$X_L$.

FIG. 6: Depicts various NOXA, BAX, BIM1, BIM2, BAK and BOK SAHB peptides. J indicates the position of the "warhead" for covalent binding to the target protein. The amino acid sequences of the different peptides are, from top to bottom, set forth in SEQ ID NOs.: 137-151, 1, and 152-155. The boldened residues in SEQ ID NOs.: 1, 38, and 39 identify the amino acids that can be replaced with a "warhead."

FIG. 7: Depicts the stapling technology and various staples that can be formed.

FIG. 11: BFL-1 Binding Activity of NOXA SAHBs. The association and dissociation binding interactions between BFL-1ΔC constructs and biotin-PEG-NOXA SAHB$_A$ peptides bearing the indicated native cysteines and cysteine-to-serine mutations were measured by biolayer interferometry. Experiments were performed in technical and biological duplicate, with exemplary association and dissociation profiles shown.

FIG. 17A: Enhanced targeting of native BFL-1 by biotinylated BIM SAHB$_A$-3, as compared to BIM SAHB$_A$, in A375P lysates, as monitored by SA pull-down and BFL-1 western analysis (top). In contrast, both compounds are equally effective at engaging MCL-1, which bears no cysteine in its BH3-binding groove and thus provides no competitive advantage for BIM SAHB$_A$-3 (bottom).

FIG. 17B: BIM SAHB$_A$-3, but not BIM SAHBA, biotinylates mitochondrial protein that migrates at the same molecular weight as immunoreactive BFL-1.

FIG. 17C: Live confocal microscopy of A375P cells treated with FITC-BIM SAHB$_A$-3 reveals its localization at the mitochondria, the intracellular site of native BFL-1. Bar, 10 μm.

FIG. 17D: A FITC-BIM SAHB$_A$-3-treated A375P cell is observed to undergo apoptosis induction, as manifested by cell shrinkage, nuclear condensation, and membrane blebbing. The colocalization FITC-BIM SAHB$_A$-3 and MitoTracker is also evident, as described above. Bar, 10 μm.

FIG. 18: Stapled Peptide Compositions.

FIG. 19: Depicts the structure of BAX bound to an inhibitor peptide found in cytomegalovirus. Distances between reactive sulfur of Cys-126 in BAX and alpha carbons of selective residues in the peptides are shown. Most relevant are distance between His-140 of 9.3 Ang and Ala-136 of 9.4 Ang as Trp-144 distance of 11.6 is both longer and appears to be occluded by direct access by a fold in BAX. The figure also shows the amino acid sequences of several exemplary stapled peptides (SEQ ID NOs: 13-21) of viral Mitochondria-localized Inhibitor of Apoptosis (vMIA) of cytomegalovirus that can be used for covalent targeting of BAX to modulate (e.g., inhibit) BAX. J=non-natural electrophile containing amino acid (note however that the electrophile can be linked to the peptide through an entity other than an amino acid); 8=R-octenyl alanine; X=S-pentenyl alanine.

FIG. 21: Depicts the structure of the Mediator head module. The structure is annotated with protein target cysteine residue number and the proximal helix residue number, and distance in Angstroms. The figure also lists amino acid sequences of exemplary stapled peptides of Mediator of RNA polymerase II transcription subunit 11 (med11) for covalent targeting for modulation (e.g., inhibition) of Mediator of RNA polymerase II transcription subunit 22 (med22). J=non-natural electrophile containing amino acid (note however that the electrophile can be linked to the peptide through an entity other than an amino acid); 8=R-octenyl alanine; X=S-pentenyl alanine.

FIG. 22: Depicts the structure of a FAS ligand peptide bound to Fas-associated death domain protein (FADD). The structure is annotated with protein target cysteine residue number and the proximal helix residue number, and distance in Angstroms. The figure also provides amino acid sequences of exemplary stapled peptides of FAS ligand for covalent targeting for modulation (e.g., inhibition) of FADD. J=non-natural electrophile containing amino acid (note however that the electrophile can be linked to the peptide through an entity other than an amino acid); 8=R-octenyl alanine; X=S-pentenyl alanine.

J=non-natural electrophile containing amino acid (note however that the electrophile can be linked to the peptide through an entity other than an amino acid); 8=R-octenyl alanine; X=S-pentenyl alanine.

Figure 24:
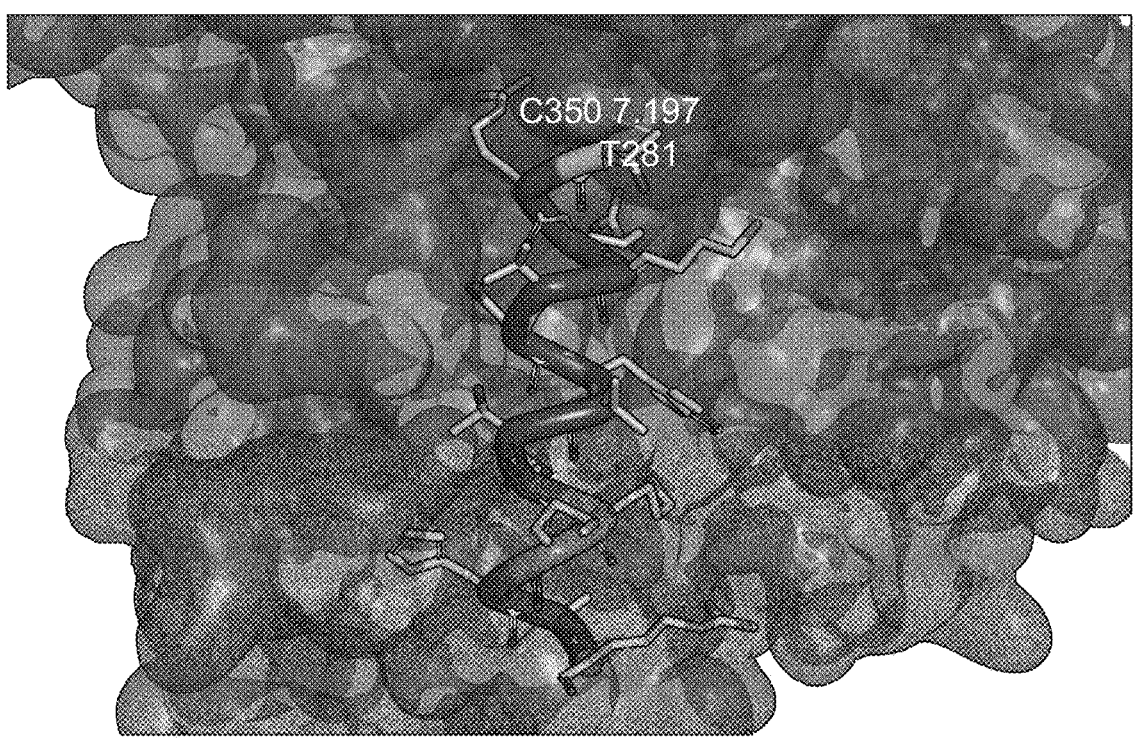

FIG. 24: Depicts the structure of an eiF4A peptide bound to the tumor suppressor, programmed cell death protein 4 (PDCD4). The structure is annotated with protein target cysteine residue number and the proximal helix residue number, and distance in Angstroms. The figure also provides amino acid sequences of exemplary stapled eIF4A peptides for covalent targeting for modulation (e.g., inhibition) of PDCD4. J=non-natural electrophile containing amino acid (note however that the electrophile can be linked to the peptide through an entity other than an amino acid); 8=R-octenyl alanine; X=S-pentenyl alanine.

Figure 25:
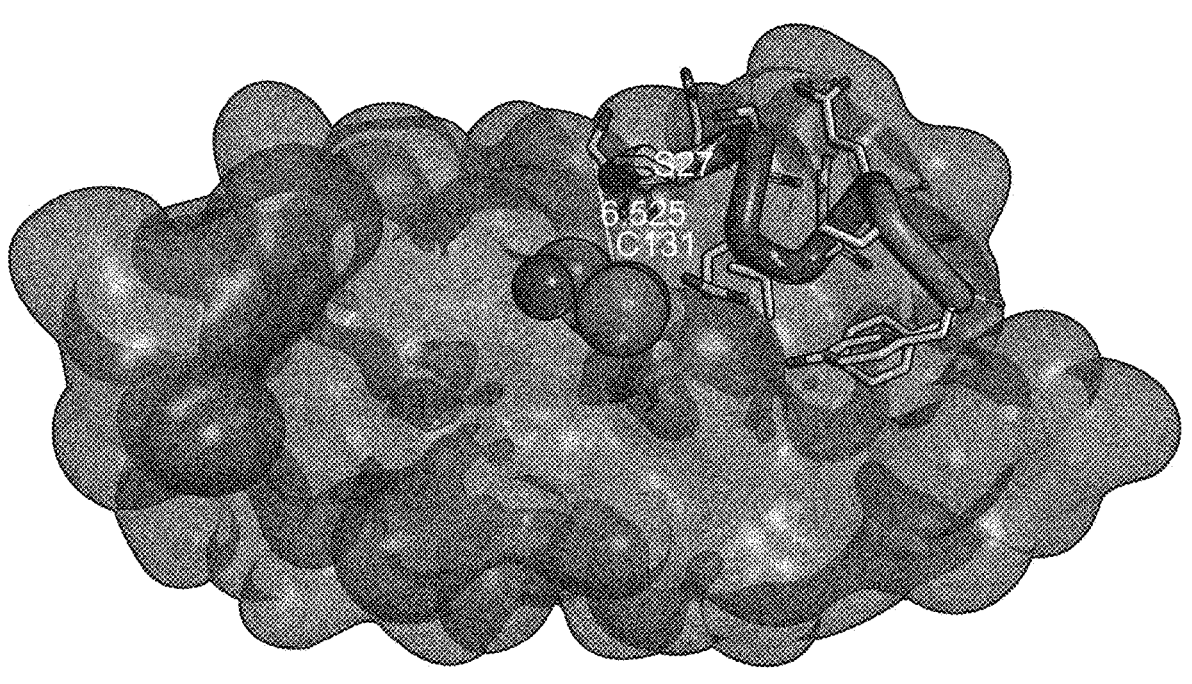

FIG. 25: Depicts the structure of a RASSF1 peptide bound to DAXX. The structure is annotated with protein target cysteine residue number and the proximal helix residue number, and distance in Angstroms. The figure also provides amino acid sequences of exemplary stapled RASSF1 peptides for covalent targeting for modulation (e.g., inhibition) of DAXX. J=non-natural electrophile containing amino acid (note however that the electrophile can be linked to the peptide through an entity other than an amino acid); 8=R-octenyl alanine; X=S-pentenyl alanine.

Figure 26:
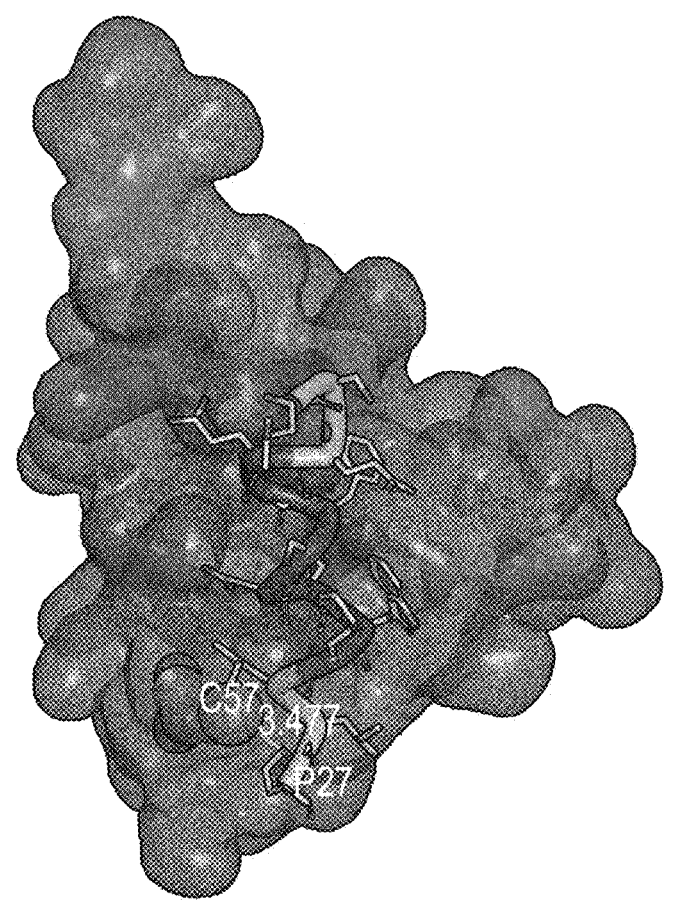

FIG. 26: Depicts the structure of a p53 peptide bound to p300. The structure is annotated with protein target cysteine residue number and the proximal helix residue number, and distance in Angstroms. The figure also provides amino acid sequences of exemplary stapled p53 peptides for covalent targeting for modulation (e.g., inhibition) of p300. J=non-natural electrophile containing amino acid (note however that the electrophile can be linked to the peptide through an entity other than an amino acid); 8=R-octenyl alanine; X=S-pentenyl alanine.

Figure 27:
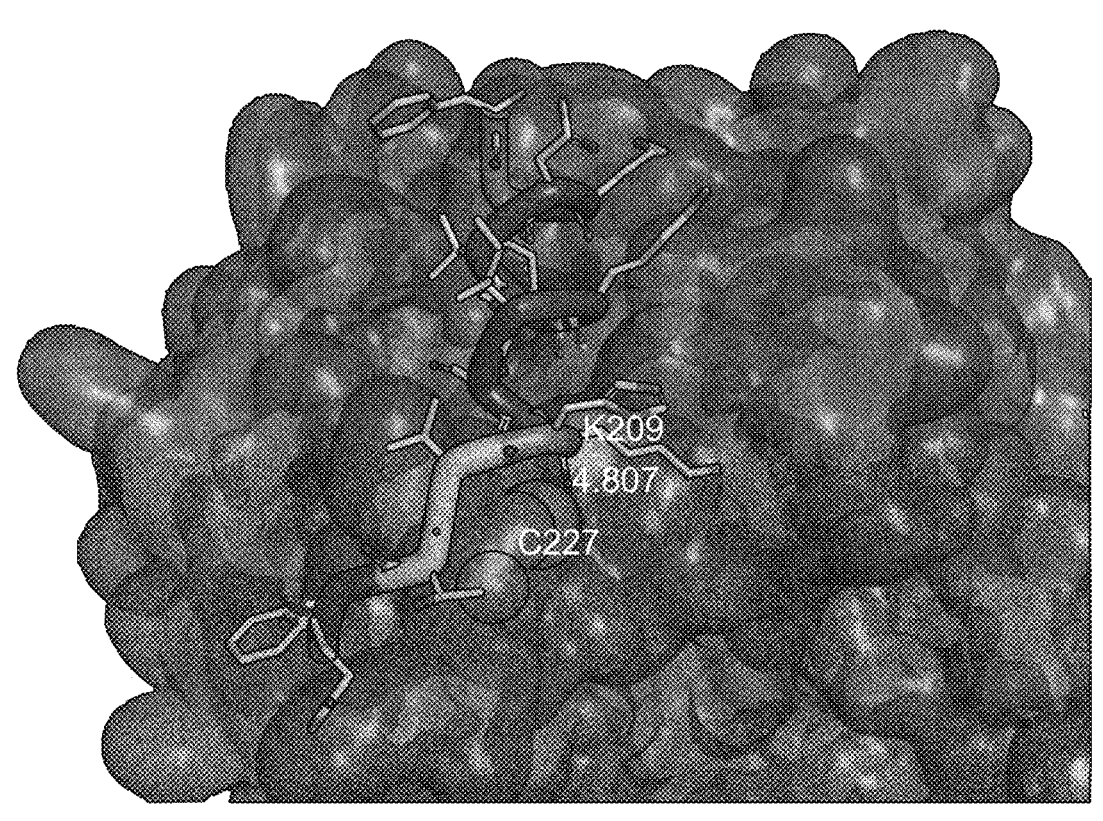

FIG. 27: Depicts the structure of a peptide bound to tryptophanyl-tRNA synthetase. The structure is annotated with protein target cysteine residue number and the proximal helix residue number, and distance in Angstroms. The figure also provides amino acid sequences of exemplary stapled peptides for covalent targeting for modulation (e.g., inhibiting) and dimer disruption of tryptophanyl-tRNA synthetase. J=non-natural electrophile containing amino acid (note however that the electrophile can be linked to the peptide through an entity other than an amino acid); 8=R-octenyl alanine; X=S-pentenyl alanine.

FIG. 28: Depicts the structure of a SOS peptide bound to RAS. The structure is annotated with protein target cysteine residue number and the proximal helix residue number, and distance in Angstroms. The figure also provides amino acid sequences of exemplary SOS stapled peptides for covalent targeting for modulation (e.g., inhibition) of RAS. J=non-natural electrophile containing amino acid (note however that the electrophile can be linked to the peptide through an entity other than an amino acid); 8=R-octenyl alanine; X=S-pentenyl alanine.

FIG. 29: Depicts the structure of a SOS peptide bound to RAS. The structure is annotated with protein target cysteine residue number and the proximal helix residue number, and distance in Angstroms. The figure also provides amino acid sequences of exemplary SOS stapled peptides for covalent targeting for modulation (e.g., inhibition) of RAS. J=non-natural electrophile containing amino acid (note however that the electrophile can be linked to the peptide through an entity other than an amino acid); 8=R-octenyl alanine; X=S-pentenyl alanine.

DETAILED DESCRIPTION

This disclosure relates, in part, to a platform technology for designing stabilized peptides that covalently bind their target protein and thereby modulate the activity of the target protein. Also provided are exemplary stabilized peptides that can be used for covalent modification of their target proteins.

Stabilized Peptides

The present disclosure provides structurally stabilized peptides having an alpha helical structure stabilized by at least two modified amino acids joined by an internal (intra-molecular) cross-link (or staple) and having a reactive group (warhead) that can form a covalent bonding with a Cys residue within a target protein to which the structurally stabilized peptide binds. Stabilized peptides as described herein include stapled peptides and stitched peptides as well as peptides containing multiple stitches, multiple staples or a mix or staples and stitches.

As described in the Examples, variant NOXA peptides with the ability to covalently bind Bfl-1 were designed. In these peptides C25 of NOXA was mutated to Serine so as avoid interfering reversible disulfide formation. L21 was mutated to the chosen electrophile selected from groups 1-10, below. L21 was selected because modelling suggested that it is located at a favorable distance from a cysteine in Bfl-1 (C55) when NOXA is bound to Bfl-1. Thus, modelling suggests a distance of 4.1 Ang between nucleophilic sulfur of the Bfl-1 and the alpha carbon of L21 in NOXA. It was predicted that electrophiles that match this distance would be most reactive. Indeed that is what is seen.

Non-limiting examples of exemplary electrophiles that can be used in the methods and compositions described herein include those shown below. They can be incorporated into an amino acid- and thus be part of a non-natural amino acid, or the chemical structures alone can be used to "cap" the peptide at the N- or C-terminus of the stabilized peptides described herein.

1

3S-1-pyrrolidine-3-carboxylic acid

2

D-homoproline

-continued

3

L-homoproline

4 isonipecotic acid

5

D-nipecotic acid

6

L-nipecotic acid

7

D-proline

-continued

8

L-proline

9 trans-4-dimethylaminocrotonic acid

10 acrylic acid

These can each be modified to terminate in an acrylamide moiety. In certain instances, the non-natural amino acid comprising an electrophilic group is(S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino) but-2-enamide; or acrylamide. In certain cases, the electrophile is not linked to an amino acid. For example, the electrophilic moiety and peptide could be linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalazine, quinazoline, purine, carbazole, indazole, benzimidazole, azaindole. The electrophilic warhead in some embodiments is an acrylamide, or more generally defined as an α,β-unsaturated carbonyl, such as α-cyanoacrylamide, propiolamide, trans 4-dimethylamino-2-butenamide, or trans 4-piperidinyl-2-butenamide, or any other substituted acrylamide. In some embodiments, the linker fulfills several critical roles. The linker servers to position the electrophile with Angstrom or sub-Angstrom precision in a location, orientation, and geometry that enables a covalent reaction to occur between the SH of the target cysteine and the alpha-beta unsaturated amide (or similar electrophilic moiety). Linkers that are rings are able to adopt a configuration that may be compatible with reaction. An aminobenzene or similar amino-derivatized aromatic ring or series of rings is also capable of precise placement. Finally, because the reactivity of the electrophile needs to be precisely tuned so as to enable the desired reaction yet not be promiscuously reactive, substituents on the linker can exert effects on the reactivity and therefore require careful selection.

Table 1 provides the spanning distance for variety of "warheads".

TABLE 1

| Summary of electrophile and distance separation | |
| --- | --- |
| Electrophile | Distance |
| acrylic acid | 1.3 |
| nipecotic | 4.3 |
| homoproline | 4.8 |
| proline | 4.9 |
| betaproline | 5.6 |
| isonipecotic | 6.5 |

An amino acid with a diamine containing side chain can be modified with an acrylic group to provide additional options for warhead spacing (Table 2).

TABLE 2

| Summary of linker and distance separation | | |
| --- | --- | --- |
| Diamine | | Distance |
| lysine | Lys | 8.7 |
| ornithine | Orn | 7.4 |
| diaminobutanoic acid | Dab | 6.2 |
| diaminopropanoic acid | Dap | 4.9 |

In some instances, the peptides can include (e.g., comprise, consist essentially of, or consist of) at least 4 (e.g., 4, 5, 6, 7, 8, 9, 10, 11, 12, 13, 14, 15, 16, 17, 18, 19, 20 or more) contiguous amino acids of a sequence selected from the amino acid sequences shown below and the peptides bind Bfl-1. In other instances, the peptides bind to Bfl-1 and are at least 40%, 45%, 50%, 55%, 60%, 65%, 70%, 75%, 80%, 85%, 90%, 95%, or 97% identical to the interacting face of the alpha-helical face of an amino acid sequence shown below:

```
                                (SEQ ID NO: 1; NOXA)
        AELEVESATQLRRFGDKLNFRQKLL (SEQ ID NO: 2; BIM)
        DMPREIWIAQELRRIGDEFNAYYARR (SEQ ID NO: 3; BAX)
        QDASTKKLSESLKRIGDELDSNMELQR (SEQ ID NO: 4; BAK)
        SSTMGQVGRQLAIIGDDINRRYDSEFQTMLQHLQ (SEQ ID NO: 5; BOK)
        PGGRLAEVSTVLLRLGDELEQIRPS (SEQ ID NO: 6; BID)
        SESQEDIIRNIARHLAQVGDSMDRSIPPG (SEQ ID NO: 7; PUMA)
        EEEQWAREIGAQLRRMADDLNAQYERRRQEEQQ (SEQ ID NO: 8; BFl-1)
        KKFEPKSGWMTFLEVTGKICEMLSLLKQYC
``` wherein the peptide has a reinforced or stabilized alpha helical secondary structure (e.g., wherein the peptide includes at least one internal crosslink) and the side chain of one amino acid is substituted by a electrophilic group that can react with the side chain of a cysteine residue. In some cases the electrophilic group is an acrylic acid. In some cases the substituted side chain includes a diamine group.

In some instances, stabilized peptides can have at least 80% (e.g., 80%, 85%, 90%, 95%, 98%, 99%, 99.5%, or 100%) identity one of SEQ ID NOs: 1-117 or can include one of SEQ ID NOs: 1-117 with one or more (e.g., 1, 2, 3, 4, 5 or 6, preferably 1-2, 1-3, 1-4 or 1-5) conservative amino acid substitutions. In some cases, the amino acid having a diamine containing side chain that is substituted with an acrylic acid is selected from: 3S-1-pyrrolidine-3-carboxylic acid; D-homoproline; L-homoproline; isonipecotic acid; D-nipecotic acid; L-nipecotic acid; D-proline; L-proline. In some cases the peptide variant has an amino terminal group selected from: 3S-1-pyrrolidine-3-carboxylic acid; D-homoproline; L-homoproline; isonipecotic acid; D-nipecotic acid; L-nipecotic acid; D-proline; and L-proline. In some cases, the stabilized peptide has the sequence of one SEQ ID NOs: 1-117 with one or two staples (e.g., one staple between two amino acids separated by 3 (or 6) amino acids or two staples each between two amino acids that are separated by 3 (or 6) amino acids). In addition, 1, 2, 3, 4 or 5 of the amino acids (whose side chains are not replaced with a staple) in this stabilized peptide can be replaced by a conservative substitution and the side chain of one amino acid is replaced by a electrophilic group that can react with the side chain of a cysteine residue.

In some instances, the disclosure provides exemplary stabilized peptides that can be used for covalent targeting for modulation (e.g., inhibition) of their respective target proteins. In certain instances, the polypeptides of this disclosure comprise or consist of a stabilized peptide that is at least 40%, 45%, 50%, 55%, 60%, 65%, 70%, 75%, 80%, 85%, 90%, 95%, or 97% identical to the interacting alpha-helical face of the peptide in any one of SEQ ID NOs.: 9-117, wherein the stabilized peptide binds to its relevant target protein (e.g., BAX, eiF4E, med22, FADD, Myosin-X, PDCD4, DAXX, p300, tryptophanyl-tRNA synthetase, RAS, or Bfl-1). In certain instances, the polypeptides of this disclosure comprise or consist of a stabilized peptide provided in any one of SEQ ID NOs.: 9-117, wherein the stabilized peptide binds to its relevant target protein (e.g., BAX, eiF4E, med22, FADD, Myosin-X, PDCD4, DAXX, p300, tryptophanyl-tRNA synthetase, RAS, or Bfl-1). In some embodiments, the polypeptide is 100, 75, 60, 50, 40, 30, 29, 28, 27, 26, 25, 24, 23, 22, 21, 20, 19, 18, 17, 16, 15, 14, 13, 12, 11, 10, 9, 8, 7, 6, 5, or 4 amino acids in length. In certain embodiments, the polypeptide is 4 to 40 amino acids in length. In some embodiments, the polypeptide comprises a stabilized alpha helix (e.g., through stapling, stitching or a combination of the two). In some embodiments, the internal staple replaces the side chains of 2 amino acids, i.e., each staple is between two amino acids separated by, for example, 3, 4, or 6 amino acids. In some embodiments, the internal stitch replaces the side chains of 3 amino acids, i.e., the stitch is a pair of crosslinks between three amino acids separated by, for example, 3 and 6 amino acids. In some embodiments, the internal staples and/or the internal stitch comprises at least two internal staples (replacing the side chains of 4 amino acids, i.e., each staple is between two amino acids separated by, for example, 3 amino acids). In some embodiments, the internal staples and/or the internal stitch comprises a combination of at least one internal staple and an internal stitch. The disclosure features pharmaceutical composition comprising a stabilized peptide selected from SEQ ID NOs.: 9-117. In certain embodiments, the non-natural amino acid comprising an electrophilic group can be, e.g., (S)-1-acryloylpyrrolidine-3-carboxamide; 1-acryloylpiperidine-4-carboxamide, (R)-1 acryloylpiperidine-3-carboxamide; (S)-1-acryloylpiperidine-3-carboxamide; (S)-1-acryloylpyrrolidine-2-carboxamide; (R)-1-acryloylpyrrolidine-2-carboxamide; (E)-4-(dimethylamino) but-2-enamide; or acrylamide. In other embodiments, the electrophile is not linked to the stabilized peptide via an amino acid. For example, the electrophilic moiety and peptide can be linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalazine, quinazoline, purine, carbazole, indazole, benzimidazole, azaindole. The electrophilic warhead in some embodiments is an acrylamide, or more generally defined as an $\alpha,\beta$-unsaturated carbonyl, such as $\alpha$-cyanoacrylamide, propiolamide, trans 4-dimethylamino-2-butenamide, or trans 4-piperidinyl-2-butenamide, or any other substituted acrylamide. Thus, the electrophile on the stabilized peptide can not only be installed in the context of a non-natural amino acid, but also as a chemical cap to the N- or C-terminus of the cross-linked (e.g., stapled, stitched) polypeptide.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

In the case of a cross-link between i and i+3 the cross-link can be a C7 alkylene or alkenylene. In the case of a cross-between i and i+4 the cross-link can be a C8 alkylene or alkenylene. In the case of a cross-link between i and i+7 the cross-link can be a C11, C12 or C13 alkylene or alkenylene. When the cross-link is an alkenylene there can one or more double bonds.

In the case of a cross-link between i and i+3 the cross-link can be a C6, C7, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001: Angew et al., Chem. Int. Ed. 37:3281, 1994). As used herein, the term "peptide stapling." includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008/121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g., 1, 4 triazole or 1, 5 triazole) crosslinks can be used (Kawamoto et al. 2012 *Journal of Medicinal Chemistry* 55:1137: WO 2010/060112).

Stapling of a peptide using all-hydrocarbon cross-link has been shown to help maintain its native conformation and/or secondary structure, particularly under physiologically relevant conditions (Schafmiester et al. 2000 *J. Am. Chem. Soc.* 122:5891-5892; Walensky et al. 2004 *Science* 305:1466-1470).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane, and/or may lead to an improvement in the peptide's biological activity relative to the corresponding uncrosslinked (e.g., "unstitched" or "unstapled") peptide.

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the figures.

Suitable tethers are described herein and in US 2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking. Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein, " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_8$ and $Xaa_9$, etc.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang et al., *J. Am. Chem. Soc.* 126:1377). Alternately, large peptides are routinely synthesized using a convergent approach whereby fully protected fragments are specifically and sequentially reacted to form the full length desired product, after final deprotection, such as in the industrial synthesis of Fuzeon.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, NY, 1962); Wilen, S. H. Tables of Resolving Agents and Optical Resolutions p. 268 (EX. Eliel, Ed., Univ. of Notre Dame Press, Notre Dame, IN 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

Either the epoxide moiety or one of the free hydroxyl (or an amino hydroxyl) moieties can be further functionalized. For example, the epoxide can be treated with a nucleophile, which provides additional functionality that can be used, for example, to attach a therapeutic agent. Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethylene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO$—$(CH_2CH_2O)_n$—$CH_2CH_2$—$Y$ where n is 2 to 10,000 and X is H or a terminal modification, e.g., a C1-4 alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —$NH(CH_2)_nC$(O)—, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α, α-Disubstituted non-natural amino acids containing olefinic side chains of varying length can be synthesized by known methods (Williams et al. J. Am. Chem. Soc., 113: 9276, 1991; Schafmeister et al., J. Am. Chem Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized) either: a) one S5 amino acid and one R8 is used; or b) one S8 amino acid and one R5 amino acid is used. R8 is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity: Compounds are dissolved in an aqueous solution (e.g. 5 mM potassium phosphate solution at pH 7, or distilled $H_2O$, to concentrations of 25-50 μM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm): Cross-linked or the unmodified template peptides are dissolved in distilled $H_2O$ or other buffer or solvent (e.g. at a final concentration of 50 μM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays: The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 μL of sera to 2 ml centrifuge tubes followed by the addition of 10 μL of 50% formic acid and 500 μL acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays: A key benefit of peptide stapling is the translation of in vitro protease resistance into markedly improved pharmacokinetics in vivo.

In vitro Binding Assays: To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). Methods for Designing Stabilized Peptides for Covalent Modulation of a Target Protein The platform technology described herein has its greatest applicability wherein a target protein binds a polypeptide (e.g., an alpha-helical polypeptide) through a binding surface that comprises a cysteine residue. Of course, the methods described herein can be adapted such that the target protein's binding surface with the polypeptide is modified by amino acid substitution to comprise a cysteine residue. Such a modified target protein may also be employed in the methods described herein.

The method involves providing a protein comprising a cysteine residue, wherein the cysteine residue is in a region of the protein that binds the polypeptide and determining the distance between the cysteine residue (e.g., the sulfhydryl group of the cysteine) to different amino acids (e.g., the alpha carbons of amino acids) of the interacting polypeptide (e.g., an alpha-helical polypeptide). To facilitate this determination one can rely on crystal structures of the target protein and/or polypeptide or rely on modeling the structures based on the known structures of related proteins (e.g., www.rcsb.org/pdb/home/home.do). If the distance range between the cysteine residue (e.g., the sulfhydryl group of the cysteine) and the alpha carbon of an amino acid of the interacting polypeptide (e.g., an alpha-helical polypeptide) is between about 0.1 $A^O$ and 12 $A^O$ (e.g., 0.1, 0.2, 0.5, 0.8, 1, 2, 3, 4, 5, 6, 7, 8, 9, 10, 11, or 12 $A^O$, or 1 to 10, 1 to 9, 1 to 8, 1 to 7, 1 to 6 $A^O$), that amino acid residue or position is identified and selected as an amino acid to substitute with a non-natural amino acid, or other chemical matter or entity linked to the stapled peptide, comprising an electrophilic group; or a position to append an electrophilic group. In some instances, amino acid substitutions are at internal position(s) of the polypeptide. In some instances, the appending of a chemical moiety comprising an electrophilic group is to the N- or C-terminus of the polypeptide. Non-limiting examples of non-naturally occurring amino acid comprising an electrophilic group include(S)-1-acryloylpyr-rolidine-3-carboxamide; 1-acryloylpiperidine-4-carboxam-ide, (R)-1 acryloylpiperidine-3-carboxamide; (S)-1-acry-loylpiperidine-3-carboxamide; (S)-1-acryloylpyrrolidine-2-carboxamide; (R)-1-acryloylpyrrolidine-2-carboxamide; (E)-4-(dimethylamino) but-2-enamide; and acrylamide. In other embodiments, the electrophile is not linked to the stabilized peptide via an amino acid. For example, the electrophilic moiety and peptide can be linked via a nitrogen containing heterocycle, either saturated (aziridine, diaziri-dine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiaz-ole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, qui-noxaline, phthalazine, quinazoline, purine, carbazole, inda-zole, benzimidazole, azaindole. The electrophilic warhead in some embodiments is an acrylamide, or more generally defined as an α,β-unsaturated carbonyl, such as α-cyano-acrylamide, propiolamide, trans 4-dimethylamino-2-butena-mide, or trans 4-piperidinyl-2-butenamide, or any other substituted acrylamide. So, the electrophile can not only be installed in the context of a non-natural amino acid, but also as a chemical cap to the N- or C-terminus of the cross-linked (e.g., stapled, stitched) polypeptide. The introduction of the electrophile facilitates covalent bond formation between the cysteine residue of the target protein and the modified polypeptide. In certain embodiments, the polypeptide is 100, 75, 60, 50, 40, 30, 29, 28, 27, 26, 25, 24, 23, 22, 21, 20, 19, 18, 17, 16, 15, 14, 13, 12, 11, or 10 amino acids in length. In certain instances, multiple locations of a polypeptide are substituted with an electrophilic group so as to achieve the ideal angle of approach or orientation of the electrophile which combined with the precise placement of the electro-phile will facilitate the formation of the covalent bond. In specific embodiments, the polypeptide comprises an alpha helical region which interacts with the interacting surface of the target protein that includes the cysteine residue. In certain embodiments, the polypeptide comprises at least two non-natural amino acids with olefinic side chains. These non-natural amino acids may be the same or different. In one embodiment, the non-natural amino acid is S-pentenyl ala-nine. In certain embodiments, the polypeptide comprises a stabilized alpha helix.

Any combination of protein and interacting polypeptide can be used in these methods. In some embodiments, the polypeptide comprises an alpha helical region which inter-acts with the interacting surface of the target protein, wherein the interacting surface of the target protein includes a cysteine residue. Non-limiting examples of such proteins and stabilized peptides are provided in Examples 9-18 of this disclosure. These examples suggest that this platform technology can be used very widely for covalent targeting of a target protein(s) of interest. In certain embodiments, the target protein is an anti-apoptotic BCL2 family of proteins (e.g., Bcl-2, Bcl-xL, Bcl-w, MCL-1, BFL-1, and BCL-B) and the interacting polypeptide is one of NOXA, BIM, BID, BAX, BAK, BOK, and PUMA.

Pharmaceutical Compositions

One or more of the stabilized peptides disclosed herein (e.g., one or more of SEQ ID NOs: 1-151) can be formulated for use as or in pharmaceutical compositions. Such compo-sitions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subder-mally, intraperitoneally, intramuscularly, and/or subcutane-ously); and/or for oral administration, transmucosal admin-istration, and/or topical administration (including topical (e.g., nasal) sprays and/or solutions).

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiologi-cal outcome (e.g., treatment of infection).

Pharmaceutical compositions of this invention can include one or more peptides and any pharmaceutically acceptable carrier and/or vehicle. In some instances, phar-maceuticals can further include one or more additional therapeutic agents in amounts effective for achieving a modulation of disease or disease symptoms.

The term "pharmaceutically acceptable carrier or adju-vant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical composi-tions of this invention include, but are not limited to, ion exchangers, alumina, aluminum stearate, lecithin, self-emul-sifying drug delivery systems (SEDDS) such as d-α-tocoph-erol polyethyleneglycol 1000 succinate, surfactants used in pharmaceutical dosage forms such as Tweens or other simi-lar polymeric delivery matrices, serum proteins, such as human serum albumin, buffer substances such as phos-phates, glycine, sorbic acid, potassium sorbate, partial glyc-eride mixtures of saturated vegetable fatty acids, water, salts or electrolytes, such as protamine sulfate, disodium hydro-gen phosphate, potassium hydrogen phosphate, sodium chloride, zinc salts, colloidal silica, magnesium trisilicate, polyvinyl pyrrolidone, cellulose-based substances, polyeth-ylene glycol, sodium carboxy methylcellulose, polyacry-lates, waxes, polyethylene-polyoxypropylene-block poly-mers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides described herein (e.g., any one or more of SEQ ID NOs.: 1-155) for the prophylaxis and/or treatment of diseases (e.g., cancer, autoimmunity, infection, etc.). The terms "treat" or "treating," as used herein, refers to partially or completely alleviating, inhibiting, ameliorating, and/or relieving the disease or condition from which the subject is suffering.

In general, methods include selecting a subject and administering to the subject an effective amount of one or more of the peptides herein, e.g., in or as a pharmaceutical composition, and optionally repeating administration as required for the prophylaxis or treatment of a disease, such as cancer, e.g., melanoma or lymphoma, and can be administered orally, intravenously, intramuscularly, subcutaneously, topically, or by inhalation or other deposition to reach an internal body part (e.g. intravaginally).

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

EXAMPLES

Example 1: Preparation of Stapled NOXA Peptides

Structurally-stabilized alpha-helical NOXA-related peptides were prepared by substituting non-natural amino acids with olefinic side chains at [i, i+4] positions in peptides having the sequence of the NOXA BH3 domain followed by ruthenium catalyzed olefin metathesis to yield NOXA SAHB peptides. Variants having deletions or substitutions in the NOXA sequence were prepared in a similar manner. A number of such peptides are depicted in FIG. 2. Fluorescent derivatives of the peptides were utilized in fluorescence polarization binding assays for to assess binding affinities to MCL-1 and Bfl-1.

These studies revealed that when F32 of the NOXA sequence was mutated to an amino acid with a bulkier side chain, the binding exhibited selectivity for Bfl-1 over MCL-1 (FIG. 3A). This might be due to the fact that there is smaller cleft in the MCL-1 binding pocket where modelling suggest F32 is directed, so bulkier residues are not tolerated as well as in the Bfl-1 pocket. A second panel of NOXA variants with substitutions at F32 was synthesized. These variants have variety of bulky side chains at the F32 position. These variants are depicted in FIG. 3B.

Example 2: Investigation of Disulfide Bond Formation

Next, the impact of the C25 in NOXA was investigated. Bfl-1 and NOXA have cysteine residues within 3.5 Å of the Bfl-1 BH3 binding pocket according to modelling. In contrast, modelling suggests that MCL-1 does not have a cysteine in close proximity to its NOXA binding pocket. To examine the impact of C25 in NOXA on target interaction, we examined the binding of WT NOXA SAHB and NOXA C25S SAHB to Bfl-1 and to a variety of Bfl-1 cysteine mutants. In vitro conjugation assays were performed in order to verify the formation of the disulfide bond. Global reduction of the protein and the NOXA peptides, followed by the introduction of an oxidant such as GSSG led to production of a disulfide bond, shown as a 3 kDa shift on non-reducing SDS-PAGE (FIG. 4A). When the opportunity for disulfide bond formation was eliminated by introducing a C25S substitution into NOXA SAHB, the binding difference was eliminated, the NOXA C25 SAHB bound with similar affinity to both Bfl-1- and MCL-1, demonstrating that the NOXA SAHB alone did not confer specificity to Bfl-1, but rather the formation of the disulfide bond that can make NOXA selective for Bfl-1. (FIG. 4A). Similar experiments using BCL-XL and MCL-1 demonstrate that only Bfl-1 forms a covalent bond with NOXA, even though BCL-XL and MCL-1 also contain cysteines within their sequences (FIG. 3B).

Figure 1:
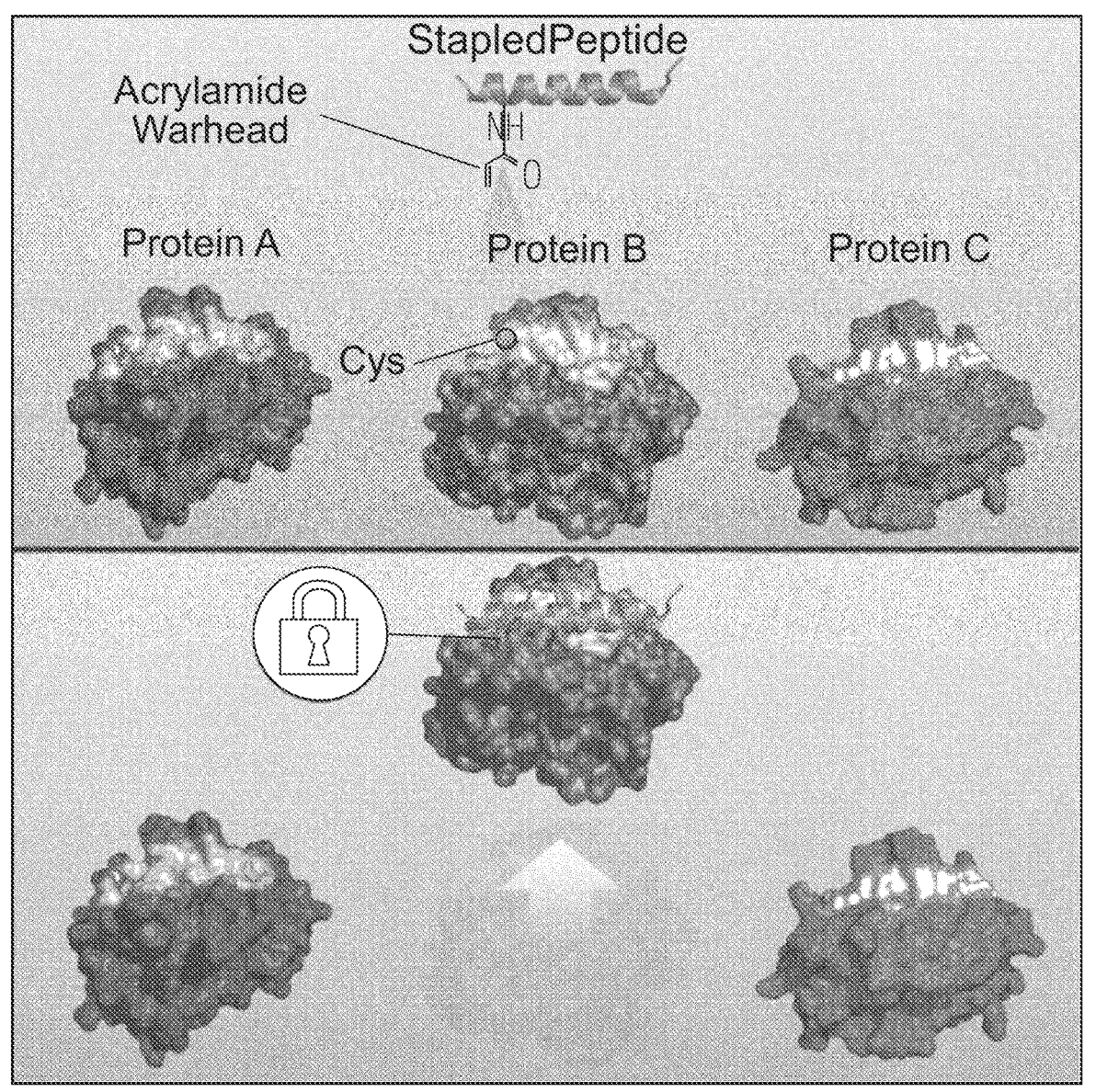
FIG. 1: Depicts the general conceptual strategy of specific targeting of acrylamide containing stapled peptides.
Figure 5A:
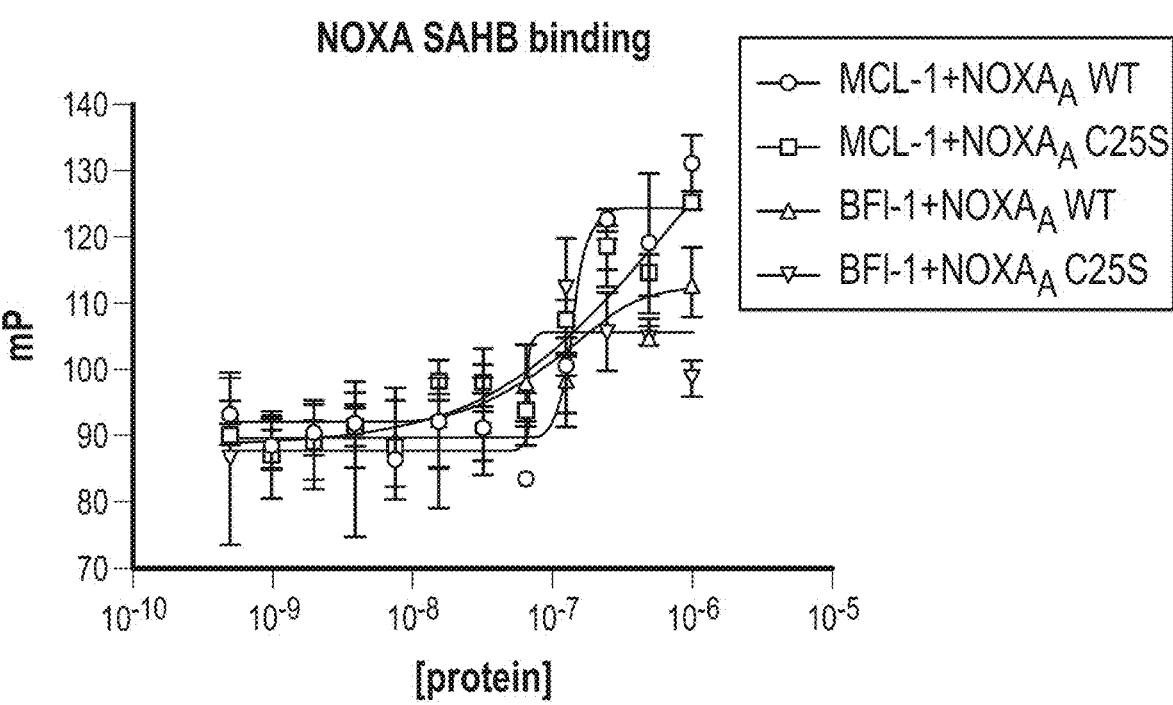
FIG. 5A: Depicts the results of binding studies showing that Cys25 of NOXA exclusively interacts with Bfl-1 Cys55, as demonstrated by testing of Bfl-1 C55S constructs.
Figure 5B:
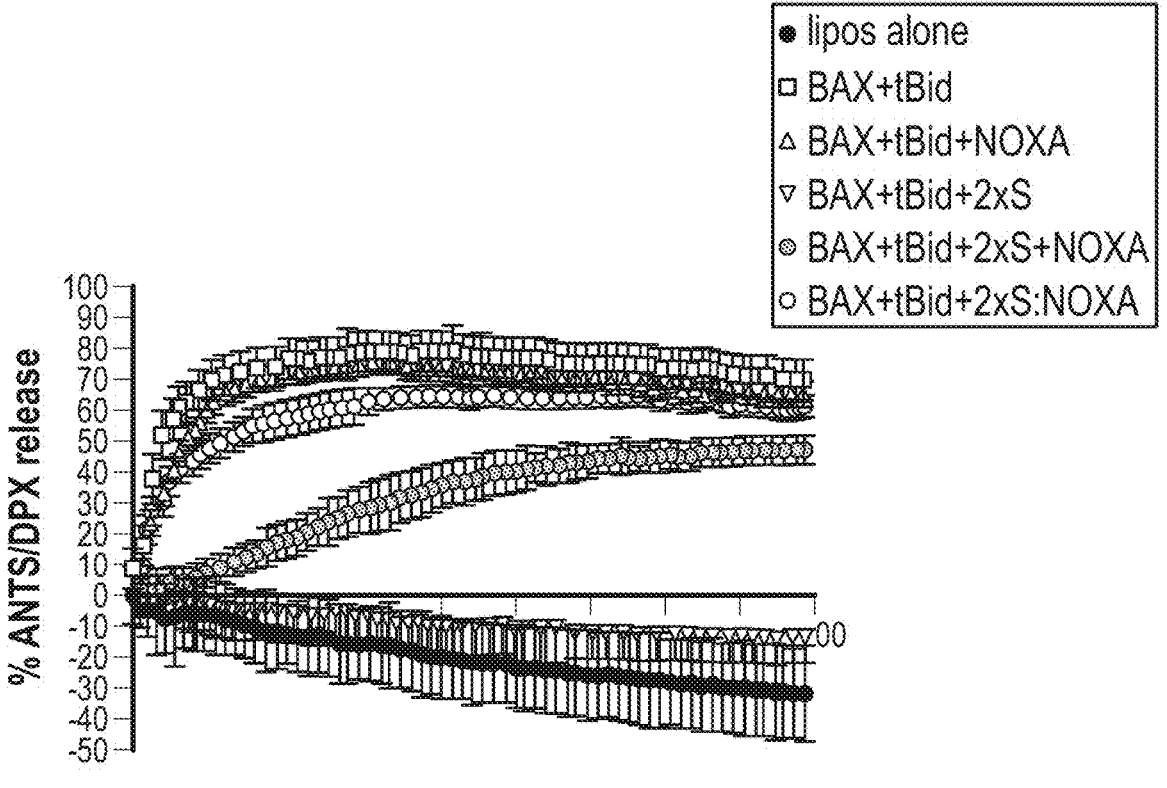
FIG. 5B: Depicts the results of studies showing that formation of a Bfl-1:NOXA disulfide bond prior to lipo-somal release assay abrogates the anti-apoptotic effects of Bfl-1 on BAX activation and liposomal dye release.

Example 3: Investigation of the Functional Impact of Disulfide Bond Formation The functional impact of the Bfl-1:NOXA disulfide bond formation was evaluated using competitive binding assays and liposomal release assays. Pre-forming the Bfl-1:NOXA disulfide bond prior to exposure binding to another FITC BH3 domain significantly decreased the availability of the Bfl-1 binding pocket even after reaching solution binding equilibrium. Use of the NOXA C25S SAHB or Bfl-1 C55S constructs abrogated these inhibitory effects. Bfl-1 alone in the liposomal release assay inhibits activation of BAX and subsequent pore formation in the liposomes. When NOXA was added concurrently with Bfl-1, the anti-apoptotic effects of Bfl-1 on BAX were somewhat inhibited. Importantly, allowing formation of the Bfl-1:NOXA disulfide bond prior to performing the liposomal release assay almost completely erases the effects of Bfl-1 and brings the activity back to that of the positive control. (FIG. 5A and FIG. 5B).

Example 4: Modification of Peptide to Include Electrophilic Warheads

To create additional NOXA SAHB variants with the potential to form a covalent bonds with C55 of Bfl-1 we generated a number of variants in which a warhead replaced either C25 or L21, both of which are expected to be within 4 Å of C55 of Bfl-1 when NOXA SAHB binds to Bfl-1. The various NOXA SAHB warhead variants are depicted in FIG. 6. In addition, warhead variants of other BH3 peptides, BIM1, BIM2, BAK, and BOK were designed. In these depictions, J indicates the position of the warhead.

FIG. 7A depicts variant amino acids that can be used to create hydrocarbon staples of various lengths. FIG. 7B depicts how the variant amino acids can be used to create staples (internal cross-links) on various lengths.

Various warhead SAHBs were tested in conjugation assays with Bfl-1. For this series of peptides the warhead at position J was selected from those depicted below.

3S-1-pyrrolidine-3-carboxylic acid

D-homoproline

L-homoproline

35

-continued isonipecotic acid

D-nipecotic acid

L-nipecotic acid

D-proline

L-proline

36

-continued trans-4-dimethylaminocrotonic acid acrylic acid

Figures 8A, 8B, 8C:
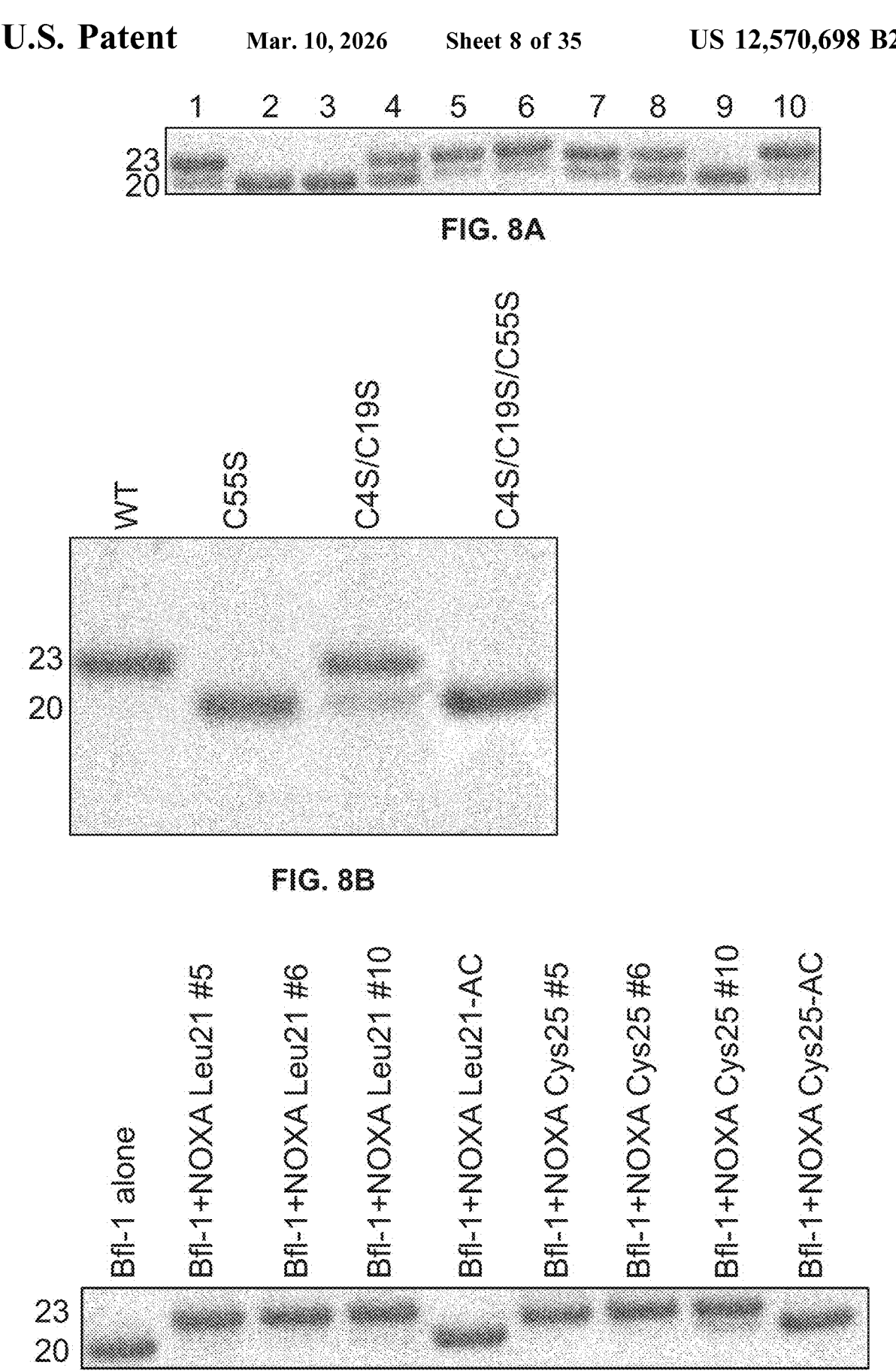
FIG. 8A: Depicts the results of a study showing that several NOXA SAHB warhead peptides bind to Bfl-1 under reducing conditions. The electrophilic substitution are: 1=3S-1-pyrrolidine-3-carboxylic acid, 2=D-homoproline, 3=L-homoproline, 4-isonipecotic acid, 5=D-nipecotic acid, 6-L-nipecotic acid, 7=D-proline, 8=L-proline, 9=trans-4-dimethylaminocrotonic acid, 10=acrylic acid.
FIG. 8B: Depicts the results of studies using Bfl-1 Cys to Ser mutants verifying that Bfl-1 Cys55, found within the binding pocket, is the only cysteine residue necessary for binding to the NOXA SAHB warhead peptides.
FIG. 8C: Depicts the results of studies showing Bfl-1 forming covalent conjugates with various NOXA warhead stapled peptides, wherein the warhead N-terminates the sequence and replaces first NOXA Leu21 and then Cys25. Linker 5, 6 and 10 are all similar except for "Ac", in which the peptide is capped with acetyl.

When compared to the disulfide bond, the covalent binding efficiency for several warheads was much higher, >90% for warheads compared to about 75% for disulfide bonds. D-homoproline, L-homoproline and trans-4-dimethylaminocrotonic acid were less efficient (FIG. 8A).

To assess whether the reactive warheads reacted substantially with off-target cysteines, we examined the binding in the presence of *E. coli* lysate or cell culture media with added BSA. No detectable off target binding was found. The NOXA warhead SAHBs interact solely with Cys55 on Bfl-1 (FIG. 8B).

BIM and BAX warhead SAHBs were also tested for Bfl-1 binding efficiency with the same results, showing that the proline-based warhead moieties can create an efficient and covalent bond with Bfl-1, both under reducing and non-reducing conditions. This is an improvement on the disulfide bond originally discovered between Bfl-1 and NOXA, which exists in sufficient quantity only under oxidizing conditions.

Figures 9A, 9B, 9C:
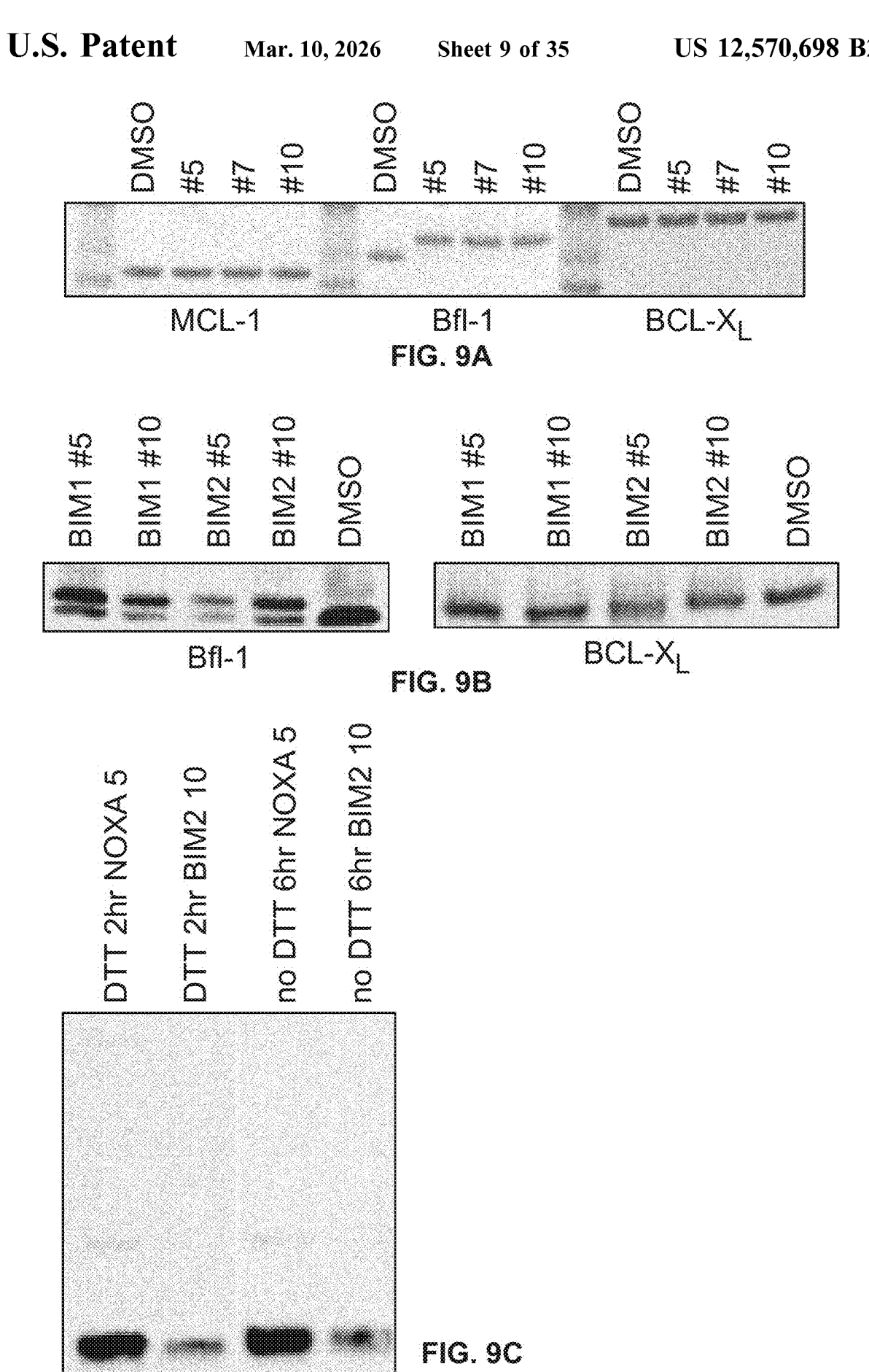
FIG. 9A: Depicts the results of a study showing that when selected NOXA warhead SAHBs were contacted to MCL-1, Bfl-1 and BCL-$X_L$, only Bfl-1 had a molecular weight shift in the presence of the SAHBs.
FIG. 9B: *E. coli* lysate overexpressing Bfl-1 and BCL-$X_L$ were spiked with BIM warhead SAHBs or DMSO and a Western blot run to test for molecular weight shifts. Only Bfl-1 displayed a molecular weight shift with the addition of BIM warhead SAHBs.
FIG. 9C: Cell culture media spiked with BSA, Bfl-1 and Btn-NOXA or BIM warhead SAHBs were Western blotted for biotin and displayed no nonspecific binding to other proteins found in the media, with bands only seen at 20 kDa for Bfl-1.

Warhead SAHBs were also tested for their binding to other antiapoptotic BCL-2 family members, which do contain cysteine residues, but not within the binding pocket. NOXA and BIM warhead SAHBs did not interact with cysteines on BCL-$X_L$ or MCL-1 FIG. 9A), even though the original BIM stapled peptides are promiscuous binders and NOXA stapled peptides interact with both Bfl-1 and MCL-1. These results were also seen in *E. coli* lysate immunoblots (FIG. 9B) and cell media containing BSA (35 cysteine residues), which was spiked with Bfl-1 (FIG. 9C). Overall, the NOXA and BIM warhead SAHBs are Bfl-1 specific binders with much higher efficiency than the prototype cysteine.

Methods Used in Examples 1-4

Solid phase peptide synthesis: Fmoc-based solid-phase peptide synthesis was used to synthesize the peptides and their stapled derivatives. To achieve the various staple lengths, α-methyl, α-alkenyl amino acids were used flanking two, three or six residues. The R5 residue were incorporated at position i and S5 at position i+3, while two S5 residues were used at the i and i+4 locations, and an R8 at position i and S5 at i+7[29]. For the stapling reaction, Grubbs 1st generation ruthenium catalyst dissolved in dichloroethane was added to the peptides while still on resin. To ensure maximal conversion, three to five rounds of stapling were performed. Once stapled, the peptides were cleaved off the resin using trifluoroacetic acid, then precipitated using a hexane:ether (1:1) mixture, and afterwards they were air dried and purified using LC-MS. We performed amino acid analysis both to precisely determine the amount of peptide purified and to ensure the correct sequence was made.

Fluorescence polarization assay: The solution-state equilibrium binding assay was used to determine binding affinities of the stapled peptides to the anti-apoptotic proteins. Proteins were serially diluted from 1 μM, then combined with FITC-labeled SAHB and polarization measured at 5 min on a microplate reader. We then calculated dissociation constants ($K_D$) by nonlinear regression analysis of dose-response curves.

Bfl-1:NOXA conjugation assay: The conjugation assay was developed to test for disulfide bond formation in a non-reducing environment. 3:1 FITC-stapled peptide:protein molar ratio was combined in the presence of DTT, then diluted and incubated with 1.2 molar excess GSSG. Samples were then run on non-reducing SDS-PAGE, scanned for fluorescence, then stained with Coomassie.

Liposomal release assay: Large unilamellar vesicles (LUVs) with lipid composition resembling the mitochondrial outer membrane were generated, encapsulating the fluorescent dye ANTS (8-aminonaphthalene-1,3,6-trisulfonic acid, disodium salt) and the quencher DPX (p-xylene-bis-pyridinium bromide). For measurement of Bfl-1-induced inhibition of BAX, Bfl-1, BAX, tBid activator and liposomes were combined. To test effects of covalently bound Bfl-1:NOXA on BAX activation, Bfl-1 and NOXA SAHB were preincubated as described, then used at the designated concentrations. ANTS release and dequenching due to DPX dissociation (F) was measured over a period of 120 min with an M1000 Infinite plate reader (Tecan) with excitation and emission wavelengths of 355 nm and 520 nm, respectively. Plates were read following liposome lysis with 1% Triton X-100 to determine maximal release (F100). Percent ANTS/DPX release was calculated as [(F−F0)/(F100−F0)]×100.

Bfl-1: Warhead SAHB Conjugation Assay

10 μM Bfl-1 was reduced with DTT, then incubated with 3:1 molar ratio of warhead SAHB. Samples were then combined with loading dye, run on a 12% Bis-Tris SDS-PAGE, and stained with Coomassie. The same setup was used for all antiapoptotic proteins tested.

*E. coli* Lysate WB

*E. coli* lysate overexpressing 9×His-tagged Bfl-1 or GST-BCL-X$_L$ was reduced with 10 mM DTT for 30 min at RT, then combined with 50 μM biotinylated BIM warhead SAHB for 2 hr at RT. The samples were then run on a 4-12% Bis-Tris SDS-PAGE, transferred, and blotted with α-BCL2A1 (Abcam 125259) and α-BCL-X$_{S/L}$ (S-18) (Santa Cruz Biotechnology).

Example 5: Covalent Reaction Between Cysteines at the Binding Interface of NOXA BH3 and BFL-1

Anti-apoptotic BCL-2 family proteins block cell death by trapping the critical α-helical BH3 domains of pro-apoptotic members in a surface groove. Cancer cells hijack this survival mechanism by overexpressing a spectrum of anti-apoptotic members, mounting formidable apoptotic blockades that resist chemotherapeutic treatment. Drugging the BH3-binding pockets of anti-apoptotic proteins has become a highest priority goal.

Figures 10A, 10B:
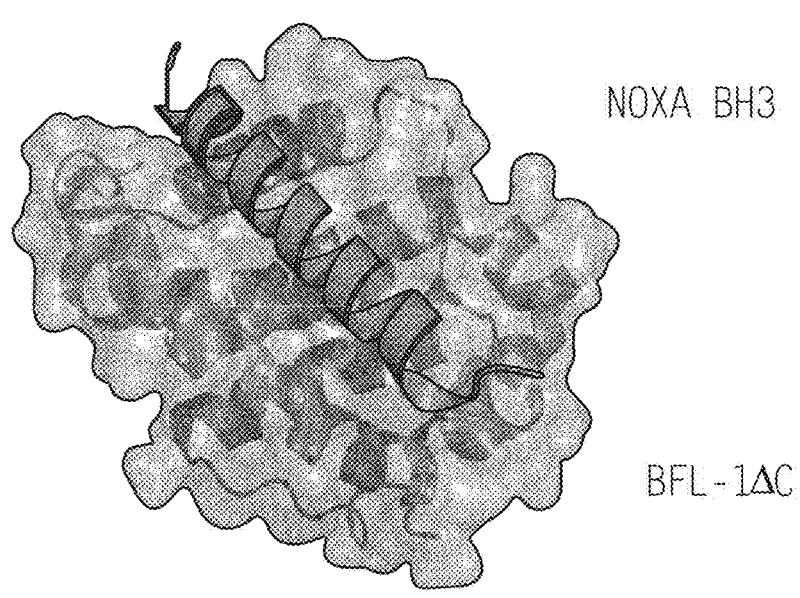
FIG. 10A: Structure of the NOXA BH3/BFL-1ΔC complex (PDB ID 3MQP) highlighting the juxtaposition between NOXA C25 and BFL-1 C55. The amino acid sequence for the NOXA SAHB$_A$ peptide has SEQ ID NO:124; the amino acid sequence for the NOXA SAHB$_A$ C25S peptide has SEQ ID NO: 128.
FIG. 10B: Dissociation constants for the binding interactions between BFL-1ΔC constructs and NOXA SAHB$_A$ peptides bearing the indicated native cysteines and cysteine-to-serine mutations. Binding experiments were performed in technical and biological duplicate.

The BH3-only protein NOXA exhibits natural, dual selectivity for interaction with anti-apoptotic MCL-1 and BFL-1, and therefore, its BH3 sequence was selected as a starting point for developing a BFL-1 inhibitor. In examining the crystal structure of human BFL-1ΔC in complex with NOXA BH3 (PDB ID 3MQP), we observed the proximity of NOXA C25 to BFL-1ΔC C55 at a distance of 3.9 Å, compatible with disulfide bond formation (FIG. 10A). As no other anti-apoptotic BCL-2 family member contains a cysteine in its BH3-binding pocket, we reasoned that C55-targeting by a stapled BH3 peptide could yield a BFL-1 inhibitor with selective covalent reactivity. To test our hypothesis, we first generated stapled NOXA BH3 peptides and recombinant BFL-1ΔC constructs bearing their native cysteines (NOXA: C25, BFL-1: C4, C19, C55) and a series of serine mutants (NOXA: C25S, BFL-1: C4S/C19S, C4S/C19S/C55S) for binding studies. For the stabilized alpha-helices of BCL-2 domains (SAHBs) modeled after NOXA BH3 (aa 19-43), we positioned the i, i+4 all-hydrocarbon staple at our classic "A" position (Walensky et al., *Science*, 305: 1466-1470 (2004)) (substitution of R31 and K35) and derivatized the N-termini with PEG-biotin for biolayer interferometry analyses. We found that the peptide/protein pairs all demonstrated dissociation constants within a 46-165 nM range (FIGS. 10B, FIG. 11). Thus, serine mutagenesis, in and of itself, appeared to have no detrimental effect on binding affinity and, if anything, somewhat enhanced BFL-1 interaction by up to 3.5-fold.

Figure 10C:
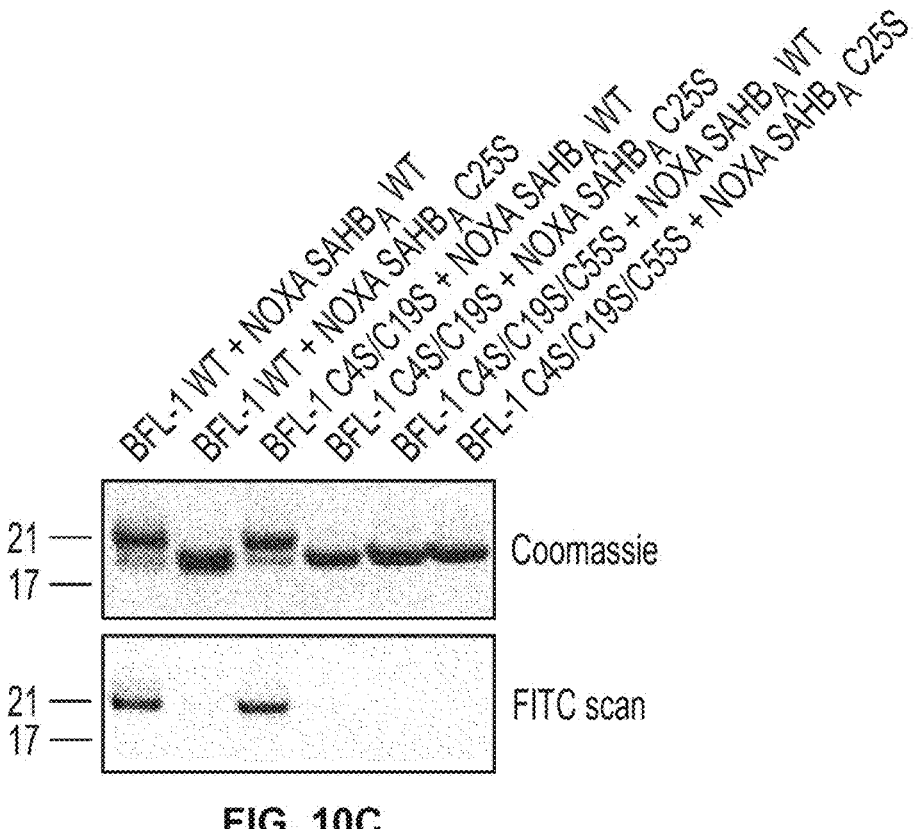
FIG. 10C: Exposure of BFL-1ΔC and FITC-NOXA SAHB$_A$ constructs to oxidizing conditions yielded a molecular weight shift only for peptide/protein pair that retain native NOXA C25 and BFL-1 C55, as detected by Coomassie staining (top). Disulfide bond formation between BFL-1ΔC bearing C55 and wild-type NOXA SAHB$_A$ was confirmed by FITC scan (bottom).
Figure 10D:
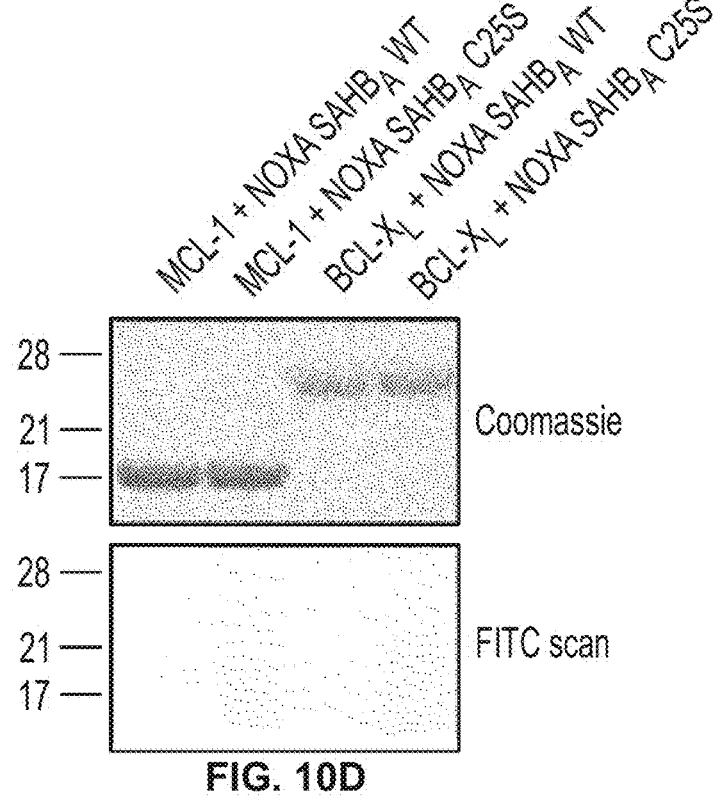
FIG. 10D: Incubation of NOXA SAHB$_A$ peptides with alternate anti-apoptotic BCL-2 family proteins, such as MCL-1ΔNΔC or BCL-X$_L$ΔC, under oxidizing conditions caused no molecular weight shift, as evaluated by Coomassie staining.

We then sought to determine if disulfide bond formation between NOXA C25 and BFL-1ΔC C55 was biochemically feasible. Indeed, upon DTT (10 mM) reduction followed by GSSG oxidation (12 mM), we observed a shift in the molecular weight of wild-type BFL-1ΔC when incubated with NOXA SAHB$_A$ but not its C25S mutant, as assessed by gel electrophoresis under denaturing and nonreducing conditions and Coomassie staining (FIG. 10C, top). Our use of FITC-NOXA SAHB$_A$ peptides provided confirmation that the BFL-1 protein was labeled by the wild-type but not C25S mutant peptide, as detected by FITC scan (FIG. 10C, bottom). We likewise determined that NOXA C25 formed a disulfide bond with BFL-1ΔC C55, as demonstrated both by the molecular weight shift (Coomassie stain) and FITC-labeling of the BFL-1ΔC C4S/C19S construct (in which only C55 is present), but no adduct with the BFL-1ΔC C4S/C19S/C55S construct that lacks C55 (FIG. 10C). As a measure of cysteine specificity, we repeated the experiment using MCL-1ΔNΔC and BCL-X$_L$ΔC, both of which contain cysteines (MCL-1 C286, BCL-X$_L$ C151), and observed no molecular weight shift or FITC labeling upon incubation with NOXA SAHB$_A$ under oxidizing conditions (FIG. 10D).

These data show that the juxtaposed cysteines at the NOXA BH3/BFL-1 interface form a disulfide bond in a selective fashion.

Figures 12A, 12B:
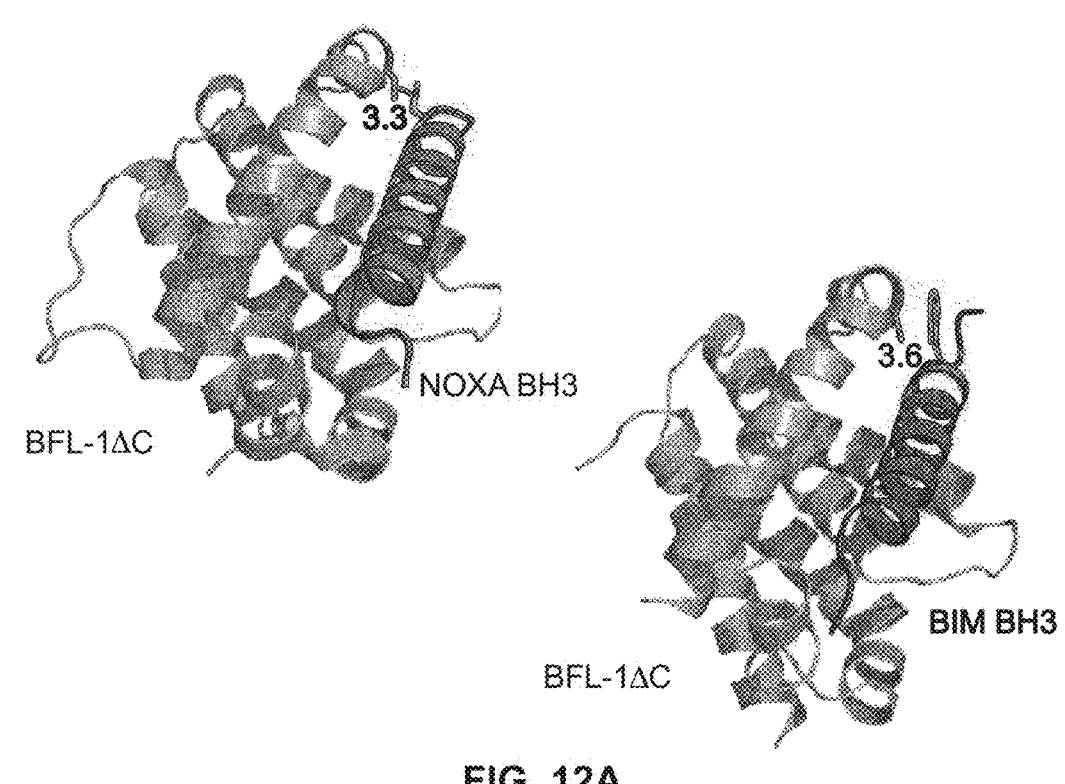
FIG. 12A: The structures of the NOXA BH3/BFL-1ΔC (left, PDB ID 3MQP) and BIM BH3/BFL-1ΔC (right, PDB ID 2VM6) complexes demonstrate the proximity of discrete BH3 residues to C55 for replacement with electrophilic warheads. The amino acid sequence for the NOXA SAHB$_A$-WH (warhead) peptide has SEQ ID NO: 139; the amino acid sequence for the BIM SAHB$_A$-WH peptide has SEQ ID NO:145.
FIG. 12B: Chemical structures of the reactive acrylamide moieties installed at the N-termini of NOXA and BIM SAHB peptides.

Example 6: Selective BFL-1 Reactivity of Stapled BH3 Peptides Bearing Electrophilic Warheads The capacity of NOXA SAHB$_A$ and BFL-1ΔC to engage through disulfide bond formation suggested a novel opportunity to develop stapled peptides for covalent targeting of cysteines localized to key regulatory surfaces, such as the BH3-binding pocket of BFL-1. Because relying on intracellular disulfide bond formation as a basis for protein target inhibition is not a tractable pharmacologic strategy, we instead examined possible sites for insertion of non-natural amino acids bearing reactive acrylamide moieties, and identified NOXA L21 as having even closer proximity to BFL-1 C55 than NOXA C25 (3.3 vs. 3.9 Å, respectively) based on the crystal structure of the NOXA BH3/BFL-1 complex (PDB ID 3MQP) (FIG. 12A, top). In the case of the more promiscuous BIM BH3 sequence, W147 manifests optimal adjacency to BFL-1 C55 (3.6 Å) based on the crystal structure of the BIM BH3/BFL-1 complex (PDB ID 2VM6) (FIG. 12A, bottom). Thus, we capped NOXA SAHB$_A$ and BIM SAHB$_A$ at positions L21 and W147, respectively, with a series of non-natural amino acids bearing distinct acrylamide species (FIG. 12B).

Figures 12C, 12D, 12E:
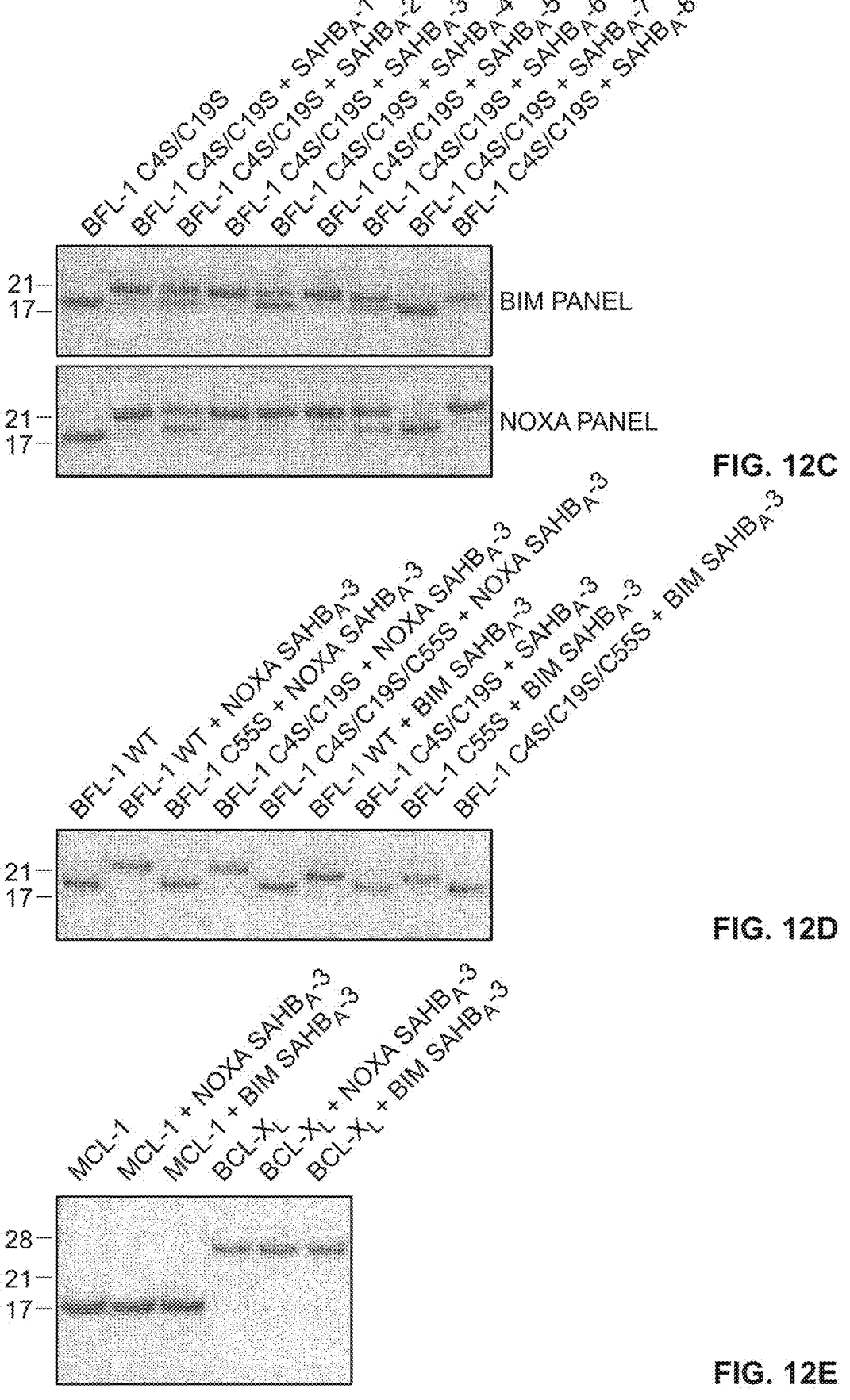
FIG. 12C: Reactivity of BIM and NOXA SAHBs bearing warheads 1-8 with BFL-1ΔC C4S/C19S, which only retains the native C55.
FIG. 12D: BIM and NOXA SAHB$_A$-3 peptides selectively reacted with BFL-1ΔC protein bearing C55.
FIG. 12E: BIM and NOXA SAHBA-3 peptides did not react with MCL-1ΔNΔC or BCL-XLΔC, despite the presence of cysteines in these anti-apoptotic targets.

In comparing the reactivity of the electrophilic "warhead"-bearing NOXA (aa 21-43) and BIM SAHB$_A$ (aa 147-166) panels, we observed efficient conversion of BFL-1 to the heavier, conjugated adduct for SAHBs bearing warheads 1, 3, 5, and 8, as assessed by reducing and denaturing gel electrophoresis and Coomassie staining (FIG. 12C). We advanced NOXA and BIM SAHBs bearing one of the most effective warheads, D-nipecotic acid (3 of FIG. 12B), to specificity testing.

First, we tested the selectivity of NOXA SAHB$_A$-3 and BIM SAHB$_A$-3 for BFL-1 C55. Upon incubation of SAHB$_A$-3 compounds with BFL-1 constructs bearing all native cysteines (BFL-1 WT), C55-only (BFL-1 C4S/C19S), C4 and C19-only (BFL-1 C55S), or no cysteines (BFL-1 C4S/C19S/C55S), we observed exclusive reactivity with the WT and BFL-1 C4S/C19S constructs, underscoring the cysteine-selectivity of NOXA SAHB$_A$-3 and BIM SAHB$_A$-3 for C55 of the BH3-binding pocket (FIG. 12D).

As a further measure of compound specificity, we repeated the experiment using MCL-1ΔNΔC and BCL-X$_L$ΔC and observed no nonspecific reactivity, despite the presence of cysteines in these anti-apoptotic BCL-2 family proteins (FIG. 12E).

Thus, we found that installing a cysteine-reactive warhead in stapled NOXA and BIM BH3 peptides results in efficient and selective covalent-targeting of the BFL-1 BH3-binding groove.

Figures 13A, 13B, 13C:
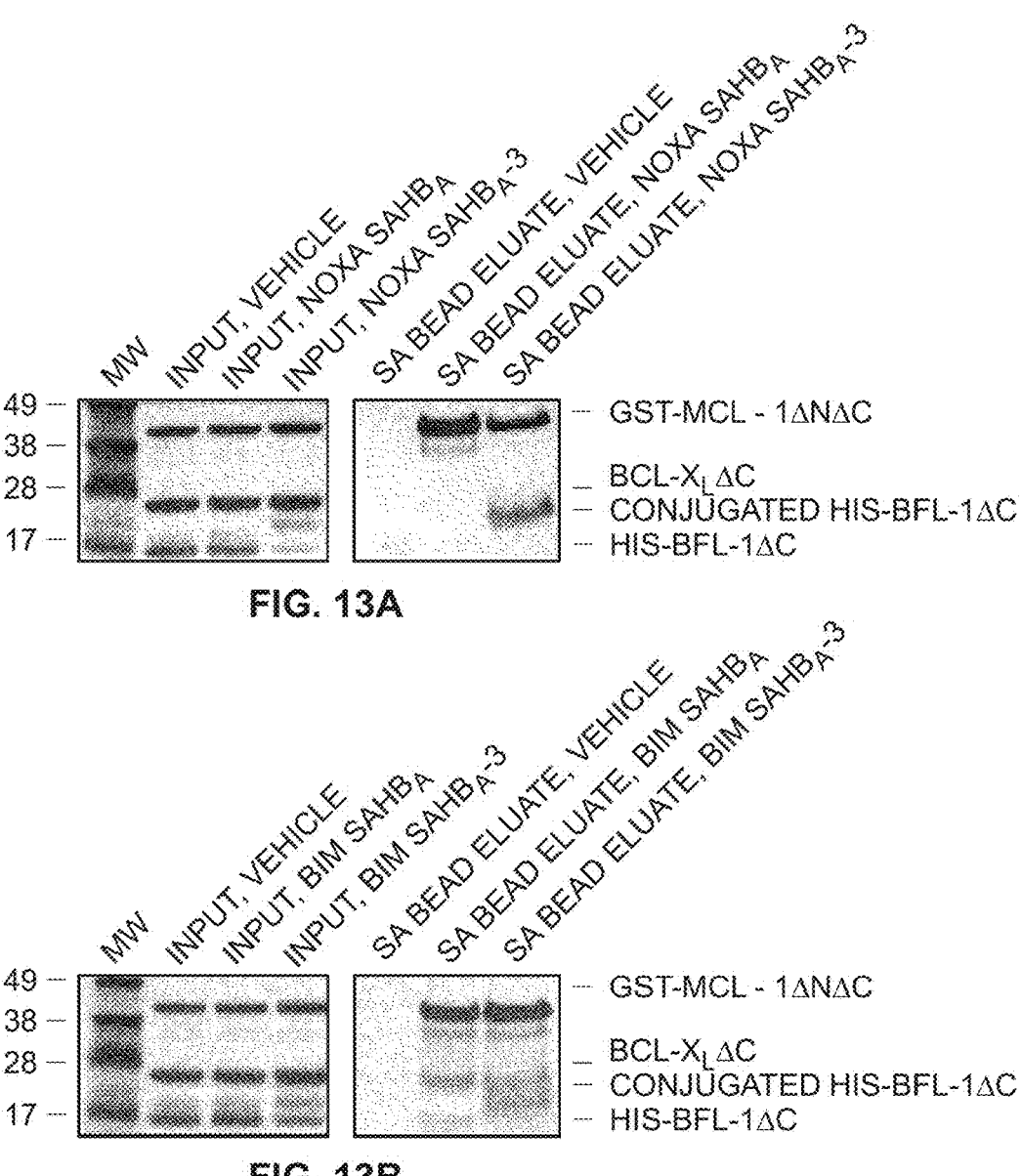
FIG. 13A: Incorporation of an acrylamide moiety into NOXA and BIM SAHBs provided a competitive advantage for BFL-1 targeting, as demonstrated by SA pull-down of a 1:1:1:1 mixture (1 μM each) of biotinylated NOXA SAHBs with recombinant His-BFL-1ΔC, BCL-X$_L$ΔC (tagless), and GST-MCL-1ΔNΔC.
FIG. 13B: Incorporation of an acrylamide moiety into NOXA and BIM SAHBs provided a competitive advantage for BFL-1 targeting, as demonstrated by SA pull-down of a 1:1:1:1 mixture (1 μM each) of biotinylated BIM SAHBs with recombinant His-BFL-1ΔC, BCL-XLΔC (tagless), and GST-MCL-1ΔNΔC.
FIG. 13C: Coomassie stain of recombinant BFL-1ΔC and its NOXA SAHBA-3 and BIM SAHBA-3 conjugates employed in liposomal release assays.

We next explored how conversion of NOXA and BIM SAHBs to BFL-1 C55-reactive agents influenced the balance between noncovalent and covalent SAHB interactions in the context of an anti-apoptotic protein mixture. First, we generated recombinant MCL-1ΔNΔC, BCL-X$_L$ΔC and BFL-1ΔC proteins with differential N-terminal tags (GST, tagless, and His, respectively) so that each could be readily identified upon gel electrophoresis and silver stain (FIG. 13A-B). Upon incubation of the anti-apoptotic mixture with biotinylated NOXA SAHB$_A$ or NOXA SAHB$_A$-3 (1:1:1:1 for each component), we only see a shift in the molecular weight of BFL-1ΔC, corresponding to the selective covalent reaction (FIG. 13A, left). Streptavidin (SA) pull-down revealed prominent non-covalent capture of MCL-1ΔNΔC by NOXA SAHB$_A$, but a notable shift in the interaction propensity of NOXA SAHB$_A$-3, with relatively less MCL-1ΔNΔC and notably more BFL-1ΔC engagement as a result of covalent BFL-1ΔC conjugation (FIG. 13A, right). Consistent with the broader anti-apoptotic binding spectrum of BIM BH3, the corresponding BIM SAHBs engaged BCL-X$_L$ΔC in addition to MCL-1ΔNΔC and BFL-1ΔC, but an increased BFL-1ΔC targeting propensity was again observed for BIM SAHB$_A$-3 relative to BIM SAHB$_A$ as a consequence of covalent conjugation (FIG. 13B).

Thus, the capacity for selective covalent reaction with BFL-1ΔC can shift the competitive balance of SAHB interactions toward BFL-1.

Example 7: Targeted Blockade of BFL-1 in Liposomes, Lysates, and Cells

Figures 13D, 13E:
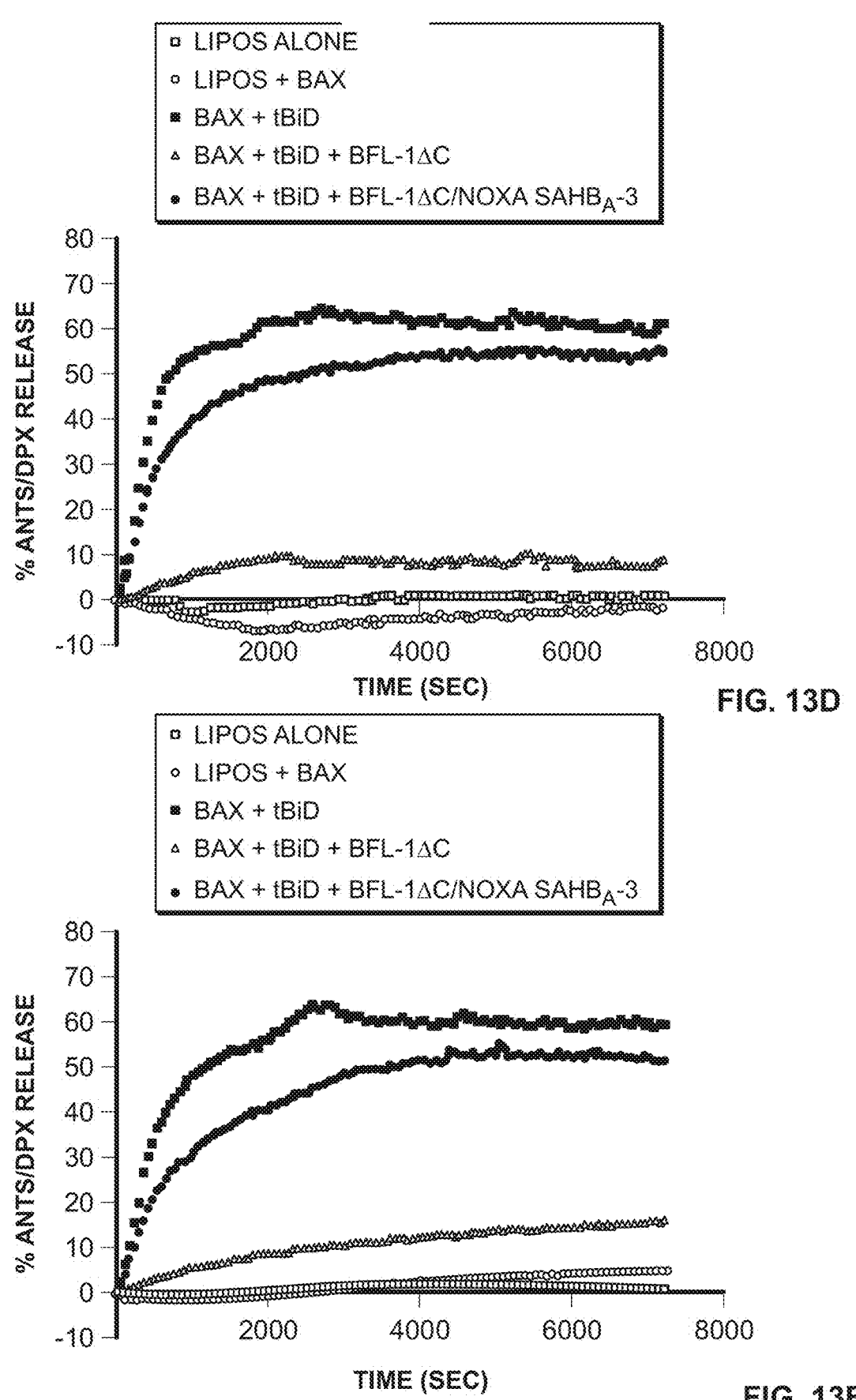
FIG. 13D: BH3-only protein tBID directly activated BAX-mediated liposomal poration, as monitored by ANTS/DPX release. Whereas BFL-1ΔC completely blocked tBID-triggered BAX poration, covalent engagement of BFL-1ΔC by NOXA SAHB$_A$-3 effectively inhibited the functional activity of BFL-1ΔC. Liposomal experiments were performed in triplicate with exemplary release profiles shown.
FIG. 13E: BH3-only protein tBID directly activated BAX-mediated liposomal poration, as monitored by ANTS/DPX release. Whereas BFL-1ΔC completely blocked tBID-triggered BAX poration, covalent engagement of BFL-1ΔC by BIM SAHB$_A$-3 effectively inhibited the functional activity of BFL-1ΔC. Liposomal experiments were performed in triplicate with exemplary release profiles shown.

To determine the functional consequences of covalent targeting of the BFL-1 BH3-binding pocket, we performed liposomal release assays designed to monitor the influence of BFL-1 on direct BAX activation. We generated ANTS/DPX-encapsulated large unilamellar vesicles (LUV) and monitored liposomal release of fluorophore upon BAX-mediated membrane poration. Whereas BAX alone had no effect on the liposomes, the addition of direct activator BH3-only protein tBID, triggered time-responsive, BAX-mediated release, a process that was suppressed by BFL-1ΔC (FIG. 13C-E). However, upon addition of either NOXA SAHB$_A$-3 or BIM SAHB$_A$-3 conjugated BFL-1ΔC (FIG. 13C), the inhibitory function of BFL-1 was lost (FIGS. 13D-E). These data highlight that covalently "plugging" the BH3-binding pocket of BFL-1 with NOXA SAHB$_A$-3 or BIM SAHB$_A$-3 irreversibly neutralizes its anti-apoptotic function.

Figures 14A, 14B:
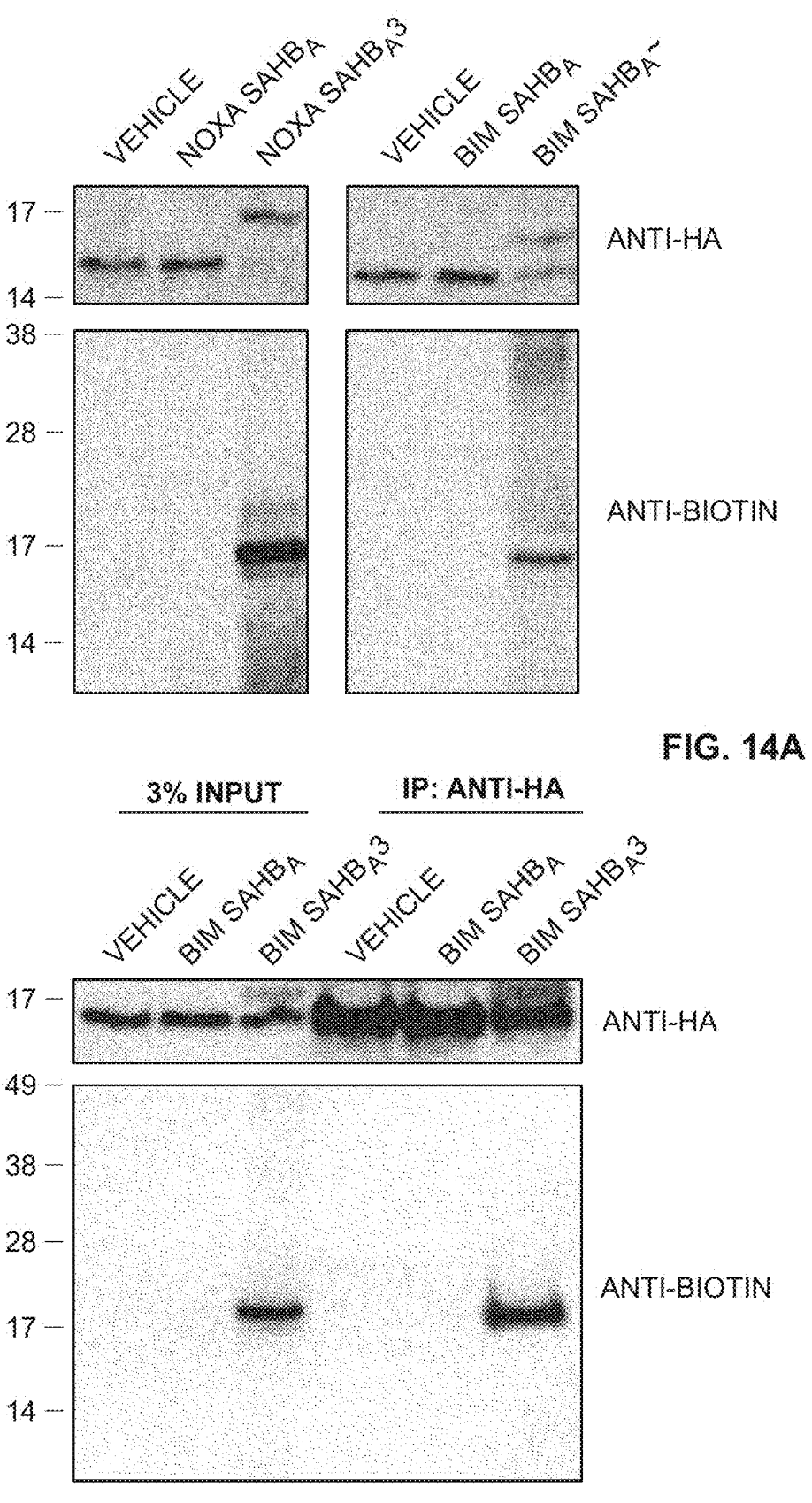
FIG. 14A: Biotinylated NOXA and BIM SAHB$_A$-3 peptides crosslinked to HA-BFL-1ΔC C4S/C19S in lysates from transfected 293T lysates, as evidenced by the shift in molecular weight of BFL-1ΔC observed upon anti-HA western analysis. Anti-biotin blotting confirmed the selective incorporation of biotin into the HA-BFL-1ΔC band, with little to no cross-reactivity with other proteins in the cellular lysate.
FIG. 14B: Treatment of transfected 293T cells with biotinylated BIM SAHB$_A$-3 followed by cellular lysis, HA immunoprecipitation, and biotin western analysis demonstrated the capacity of a warhead-bearing BIM SAHB to gain intracellular access and covalently target expressed HA-BFL-1ΔC C4S/C19S containing the native C55.

We next sought to test whether our covalent stapled peptide inhibitors could selectively react with BFL-1 in more complex protein mixtures. To specifically track C55 derivatization, we transiently expressed HA-BFL-1ΔC C4S/C19S in 293T cells and, after 24 hours, harvested cell lysates for crosslinking analyses with C-terminal Lys-biotin derivatized SAHB constructs that either did or did not contain the electrophilic warhead. Anti-HA western analyses revealed prominent molecular weight shifts only for warhead-bearing SAHBs, consistent with covalent incorporation of both NOXA SAHB$_A$-3 and BIM SAHB$_A$-3 into the BFL-1 protein at C55 (FIG. 14A, top). To confirm that the observed molecular weight shifts reflected NOXA SAHB$_A$-3 and BIM SAHB$_A$-3 incorporation, we performed biotin western analyses. We found that the shifted HA-BFL-1 bands were indeed biotin-immunoreactive and, importantly, there was little to no non-specific reactivity with other electrophoresed proteins from the 293T lysates (FIG. 5A, bottom).

Figure 15A:
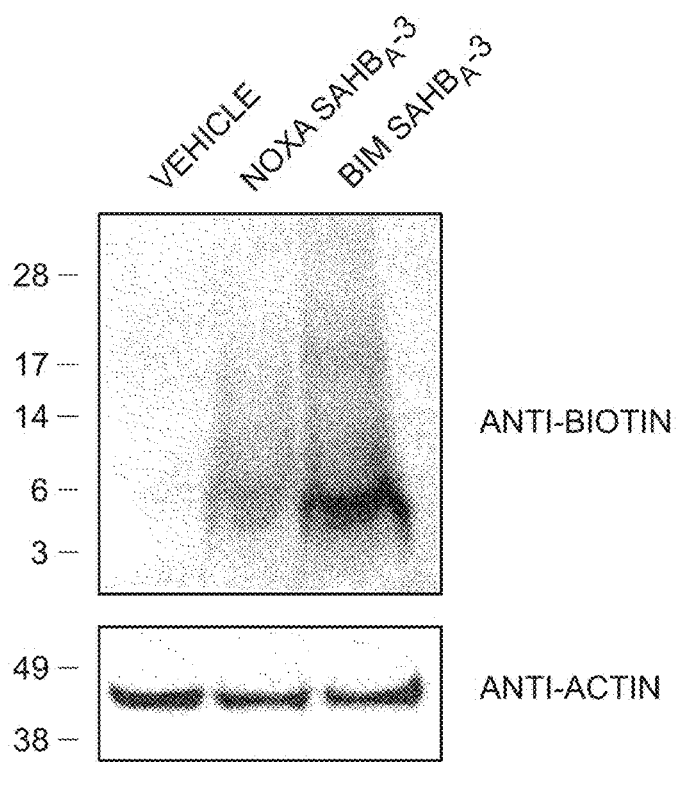
FIG. 15A: 293T cells were treated with biotinylated NOXA SAHB$_A$-3 or BIM SAHB$_A$-3 (20 μM) for 24 h followed by washing, trypsinizing, rewashing and lysing the cells. Comparative stapled peptide uptake was assessed by electrophoresis of the cellular lysates and biotin western analysis.
Figure 15B:
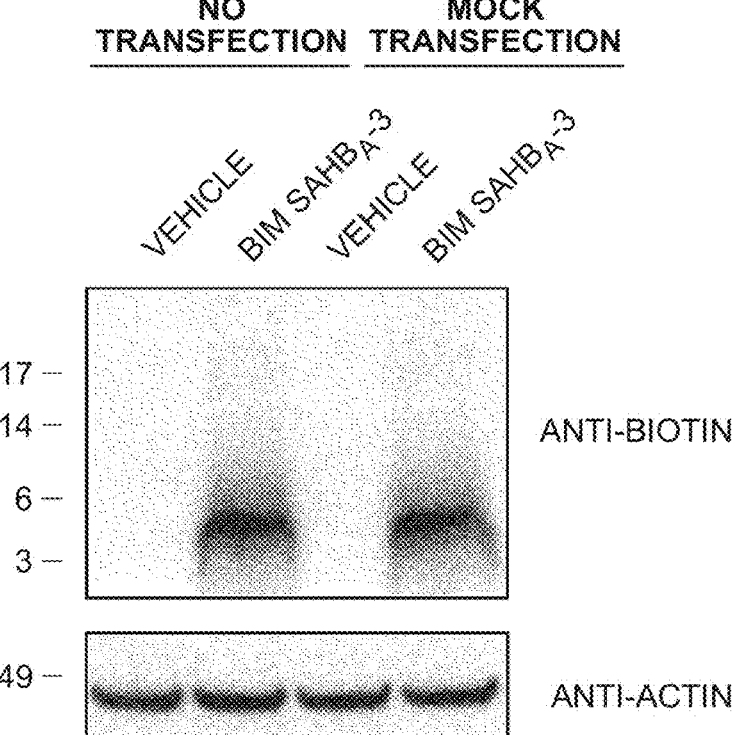
FIG. 15B: 293T cells were either mock transfected or not, and then 24 h later treated with biotinylated BIM SAHB$_A$-3 (20 μM) for an additional 4 h, and then processed as above for comparative biotin blotting of cellular lysates.

To advance our strategy to cellular testing, we first evaluated the cellular uptake potential of our biotinylated NOXA SAHB$_A$-3 and BIM SAHB$_A$-3 constructs. We incubated 293T cells with the compounds at 20 µM dosing for 24 hours, trypsinized and washed the cells to remove any adherent peptide, and then generated lysates for anti-biotin western analyses. We proceeded with BIM SAHB$_A$-3 for cellular testing (FIG. 15A). We further confirmed that the transfection conditions themselves did not independently influence the cellular uptake of BIM SAHB$_A$-3 (FIG. 15B). 293T cells transiently overexpressing HA-BFL-1ΔC C4S/C19S were treated with biotinylated BIM SAHB$_A$ (aa 147-166) or BIM SAHB$_A$-3 (20 µM, 6 h) and then lysates, generated as above, were subjected to anti-HA immunoprecipitation. Biotin western analysis of the input revealed a single, prominent protein band only in the denatured and reduced electrophoresed lysate of cells treated with BIM SAHB$_A$-3 (FIG. 14B, left). Subjecting the immunoprecipitate to anti-HA western analysis revealed the BFL-1 doublet, and biotin western analysis confirmed that the upper band indeed corresponded to biotinylated HA-BFL-1 (FIG. 14B, right).

Figure 14C:
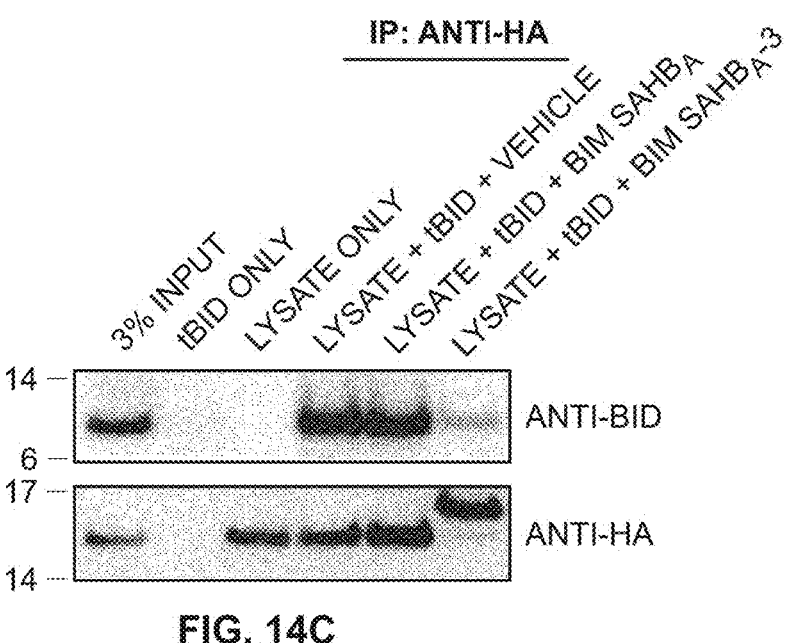
FIG. 14C: BIM SAHB$_A$-3, but not BIM SAHB$_A$, effectively competed with tBID for HA-BFL-1ΔC C4S/C19S interaction in 293T lysates, achieving robust covalent conjugation, as measured by the indicated immunoprecipitation and western analyses.
Figure 14D:
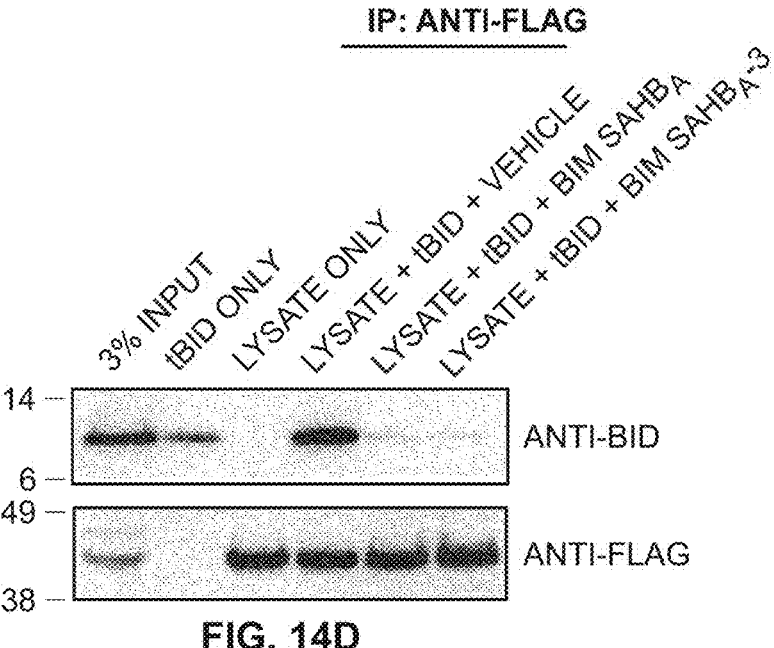
FIG. 14D: In the context of exclusive non-covalent FLAG-MCL-1 interaction, the compounds-BIM SAHB$_A$-3 and BIM SAHB$_A$-were equally effective at competing with tBID, as measured by the indicated immunoprecipitation and western analyses.

Having documented the feasibility of specific labeling of intracellular BFL-1 upon treating cells with biotinylated BIM SAHB$_A$-3, we then examined the relative influence of covalent vs. non-covalent engagement on the capacity of BIM SAHBs to disrupt BFL-1 complexes. For this experiment, we added tBID to the lysates from 293T cells transiently transfected with HA-BFL-1ΔC C4S/C19S, incubated the mixture with biotinylated BIM SAHB$_A$ or BIM SAHB$_A$-3, performed anti-HA immunoprecipitation and blotted for HA, tBID, and biotin. Strikingly, BIM SAHB$_A$ was incapable of competing with tBID for HA-BFL-1 binding, whereas the warhead-bearing BIM SAHB$_A$-3 construct covalently trapped HA-BFL-1, as exemplified by complete protein conversion to the higher molecular weight species and near total inhibition of tBID co-immunoprecipitation (FIG. 14C). When the experiment was repeated using lysates from 293T cells transiently expressing FLAG-MCL-1, which bears no cysteine in its BH3-binding pocket, both BIM SAHB$_A$ peptides were equally effective as non-covalent disruptors of tBID/FLAG-MCL-1 co-immunoprecipitation (FIG. 14D). Thus, by installing the warhead and enabling stapled peptide covalent reaction, the BFL-1 targeting efficacy of BIM SAHB$_A$ can be selectively enhanced.

Figure 14E:
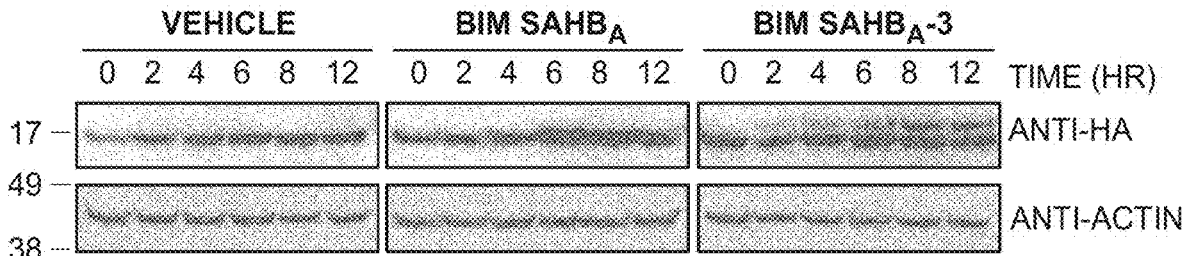
FIG. 14E: Covalent modification of HA-BFL-1ΔC C4S/C19S by cellular treatment with BIM SAHBA-3, but not the corresponding construct lacking the acrylamide-based warhead. Crosslinked BF1-1ΔC was observed by 2 hours and levels continued to increase in a time-dependent fashion throughout the 12 hour treatment period, as monitored by HA western analysis.

Finally, we turned to the corresponding non-biotinylated BIM SAHB$_A$ constructs to probe the kinetics and efficiency of covalent targeting of BFL-1 in cells. Comparing BIM SAHB$_A$- and BIM SAHB$_A$-3-treated 293T cells transiently overexpressing HA-BFL-1ΔC C4S/C19S, we observed a discrete molecular weight shift in BFL-1 by anti-HA western analysis within 2 hours of BIM SAHB$_A$-3 exposure, with a progressive increase in the crosslinked species over the 12 hour evaluation period (FIG. 14E).

Taken together, these data highlight the capacity of a stapled peptide bearing an electrophilic warhead to covalently target BFL-1 in treated lysates and cells.

Example 8: Preferential Activation of Apoptosis by a Cysteine-Reactive BIM SAHB$_A$ in BFL-1-Expressing Melanoma BFL-1 has recently been implicated as a lineage-specific driver of human melanoma, with gene amplification observed in ~30% of cases and BFL-1 overexpression mediated by the MITF transcription factor, a melanoma oncogene (Haq et al., *Proc Natl Acad Sci USA* 110:4321-4326 (2013)). Thus, to explore the functional impact of covalent BFL-1 targeting in cancer cells driven by BFL-1 expression, we tested the comparative effect of BIM SAHB$_A$-3 with a noncovalent stapled peptide modulator of BCL-2 family proteins, BIM SAHB$_{A1}$ in A375P melanoma cells. We first confirmed that BIM SAHB$_{A1}$ and BIM SAHB$_A$-3 have equivalent cellular uptake, as quantified by ImageXpress Micro (IXM) high content epifluorescence microscopy of treated A375P cells and mouse embryonic fibroblasts (MEFs), which we have used previously to benchmark the comparative cell penetrance of FITC-labeled stapled peptides (Bird et al., Biophysical determinants for cellular uptake of hydrocarbon-stapled peptide helices. *Nat Chem Biol* in press. 2016) (data not shown). The mechanism of uptake for BIM SAHBs is consistent with micropinocytosis and evidenced by the epifluorescence microscopy pattern of treated A375P and MEF cells at 4 hours (data not shown).

Figure 16A:
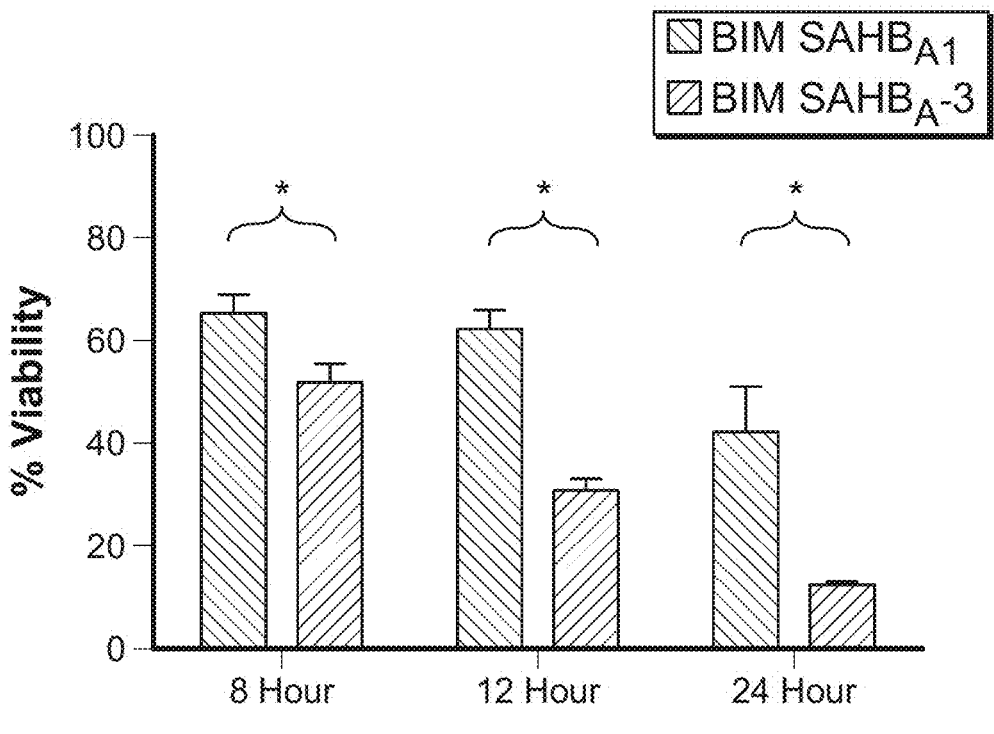
FIG. 16A: A375P cells were treated with BIM SAHB$_{A1}$ or BIM SAHB$_A$-3 (40 μM) and viability measure by CellTiter-Glo assay at the indicated time points. Data are mean±s.d. for experiments performed in technical sextuplicate, and repeated twice using independent cell cultures with similar results.
Figure 16B:
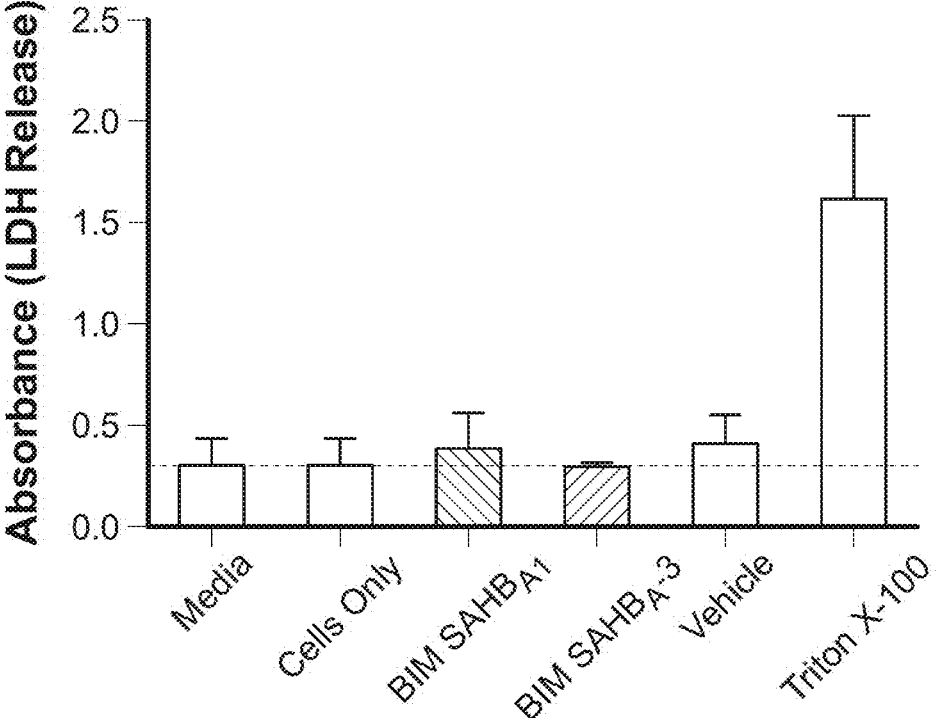
FIG. 16B: Quantitation of LDH release upon treatment of A375P cells BIM SAHB$_{A1}$ or BIM SAHB$_A$-3 (40 μM) for 30 min. Data are mean±s.d. for experiments performed in technical triplicate.
Figure 16C:
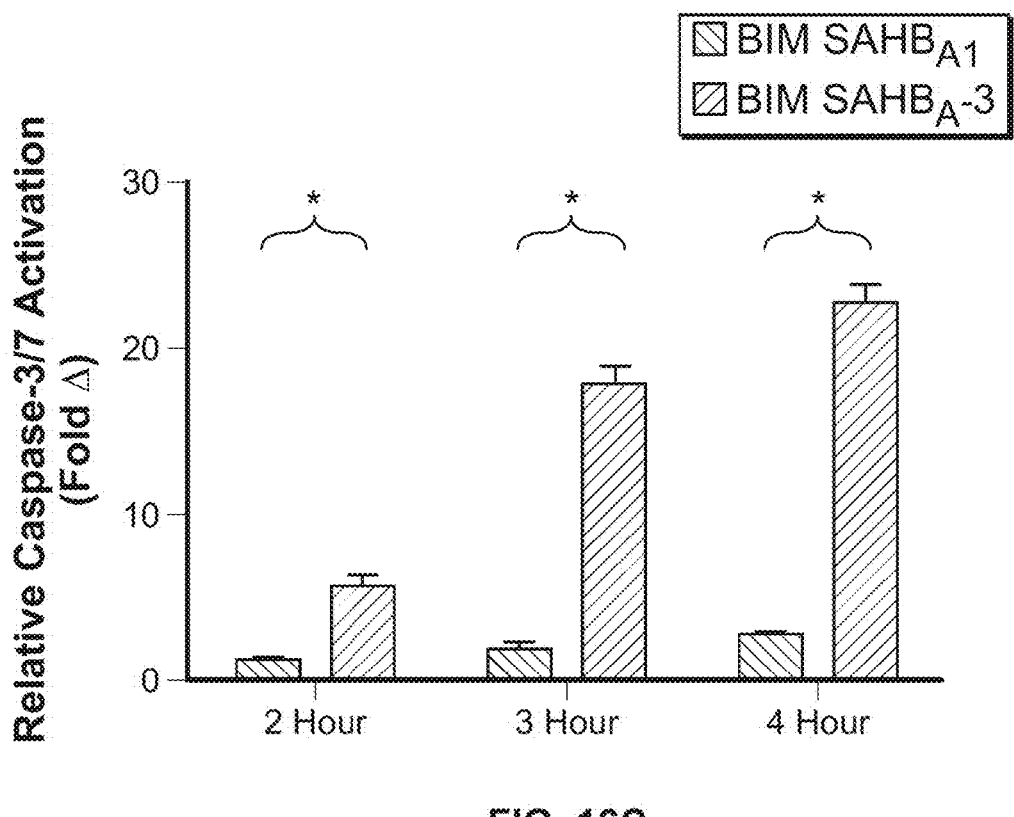
FIG. 16C: A375P cells were treated with BIM SAHB$_{A1}$ or BIM SAHB$_A$-3 (40 μM) and caspase 3/7 activation measured by Caspase-Glo assay at the indicated time points. Data are mean±s.d. for experiments performed in technical sextuplicate, and repeated twice using independent cell cultures with similar results.
Figure 16D:
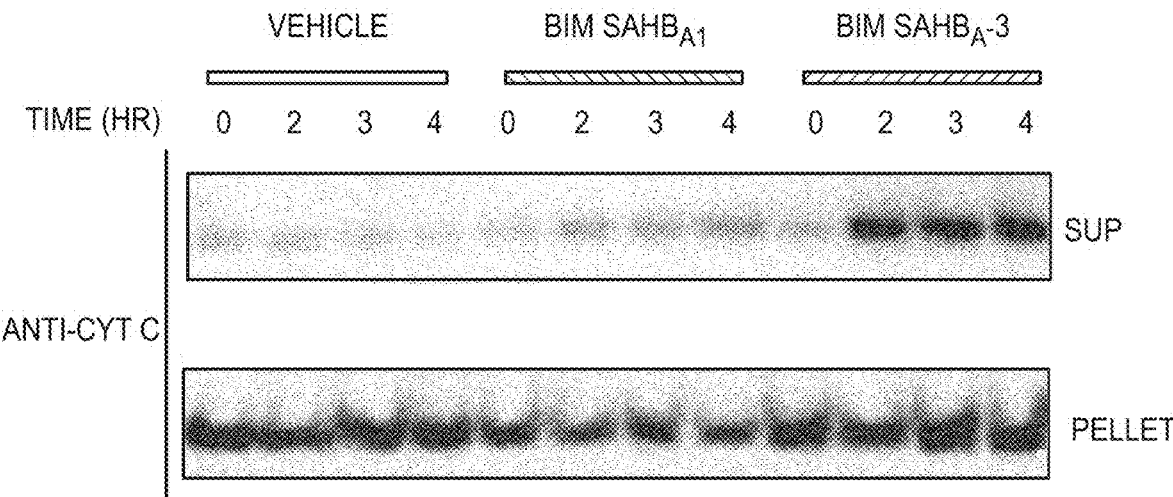
FIG. 16D: Mitochondrial cytochrome c release in A375P cells treated with BIM SAHB$_{A1}$ or BIM SAHB$_A$-3 (40 μM), as detected by cytochrome c western analysis of cytosolic and mitochondrial fractions harvested at the indicated time points. *, $p<0.001$ by two-tailed Student's t test.

Upon exposure of A375P cells to BIM SAHBs, we observed significant enhancement in cytotoxicity over time for the warhead-bearing BIM SAHB$_A$-3 compared to BIM SAHB$_{A1}$ (FIG. 16A). We confirmed by LDH release assay that BIM SAHBs had no membranolytic effect on the cells (FIG. 16B). The observed cytotoxicity was instead consistent with mitochondrial apoptosis induction, as reflected by time-responsive caspase 3/7 activation (FIG. 16C) and mitochondrial cytochrome c release (FIG. 16D). In accordance with its more pronounced impairment of cell viability, BIM SAHB$_A$-3 treatment induced higher levels of caspase 3/7 activation and cytochrome c release compared to that observed for BIM SAHB$_{A1}$ (FIG. 16C-D). To mechanistically link the enhanced susceptibility of A375P cells to preferential BIM SAHB$_A$-3 engagement of BFL-1, we incubated A375P lysates with the corresponding biotinylated BIM SAHBs, followed by SA pull-down and anti-BFL-1 and MCL-1 western analyses. Whereas BIM SAHB$_A$ and BIM SAHB$_A$-3 demonstrated equivalent binding to anti-apoptotic MCL-1, as previously observed in the context of competitive interaction with recombinant anti-apoptotic proteins (FIG. 13B), the warhead-bearing construct again showed markedly increased engagement of BFL-1 (FIG. 17A). To verify that BIM SAHB$_A$-3 can indeed label native mitochondrial BFL-1, we incubated mitochondria purified from A375P cells with biotinylated BIM SAHBs and observed BIM SAHB$_A$-3-selective biotinylation of mitochondrial protein at the identical molecular weight as immunoreactive BFL-1 (FIG. 17B). Live confocal microscopy imaging of A375P cells treated with FITC-BIM SAHB$_A$-3 further revealed the stapled peptide's striking intracellular localization at the mitochondria, the physiologic site of BFL-1 activity, in both morphologically normal A375P cells (FIG. 17C) and those undergoing apoptosis induction, as reflected by cell shrinkage, nuclear condensation, and membrane blebbing (FIG. 17D).

Importantly, we observed comparative enhancement in cytotoxicity and caspase 3/7 activation for BIM SAHB$_A$-3 in two additional BFL-1 expressing melanoma cell lines (SK-MEL-2, SK-MEL-28) (data not shown), but no evidence of this phenomenon in non-melanoma lines that either lack or maintain BFL-1 expression, but are driven by alternate oncogenic mechanisms (e.g., A549, MCF7, H929) (data not shown).

Taken together, these data highlight the mechanistic advantage of the warhead-bearing BIM SAHB$_A$-3 in the context of BFL-1-dependent cancer, as reflected by more effective engagement of native BFL-1 and greater efficacy in triggering apoptosis. Thus, in addition to harnessing a cysteine-reactive targeting strategy to selectively trap BFL-1, heightened susceptibility to covalent BFL-1 inhibitors such as BIM SAHB$_A$-3 also provide a diagnostic approach for identifying BFL-1 dependency in human cancers.

Methods Used in Examples 5-8

Stapled Peptide Synthesis: Hydrocarbon-stapled peptides corresponding to the BH3 domains of BCL-2 family proteins, and either N-terminally derivatized with acetyl, FITC-βAla, biotin-PEG, or electrophilic warheads, or C-terminally derivatized with Lys-biotin, were synthesized, purified, and quantitated using our previously reported methods (Bird et al., *Methods Enzymol.*, 446:369-386 (2008); Bird et al., *Curr. Protoc. Chem. Biol.*, 3:99-117 (2011)). Acrylamide-bearing peptides were synthesized by either coupling acrylic acid or trans-crotonic acid to the peptide N-terminus, or by first coupling the Fmoc protected cyclic amino acids (Chem-Impex International) followed by Fmoc deprotection and acylation with acrylic acid, using standard Fmoc coupling and deprotection methods. FITC derivatization of acrylamide-bearing peptides are detailed below. Stapled peptide compositions, and their observed masses and use by figure, are shown in FIG. 18.

FITC Derivatization of Acrylamide-Bearing Stapled Peptides: Cystamine dihydrochloride (1 eq) was dissolved in 10 mL DMSO, accompanied by 270 μL DIEA (3 eq), and then 400 mg (2 eq) of FITC was added. The reaction was monitored by LCMS and, after overnight stirring and reaction completion, 2 eq TCEP in 1 mL of water was added. The reduced product was purified on an Isco CombiFlash purification system equipped with a 40 g C18 reversed phase column using a water-acetonitrile gradient. The fractions containing product were lyophilized to afford 385 mg of FITC-labeled cysteamine. The subsequent conjugation reaction with acrylamide-containing stapled peptide was found to be pH dependent as expected, with no reaction occurring at pH 6 and pH 8, whereas the reaction in pH 10 borate buffer went to completion after overnight incubation in a 1:1:3 solution of 1 mM DMSO peptide stock, 5 mM DMSO stock of FITC-cysteamine, and 0.05 M borate buffer. The FITC-labeled peptide product, FITC-Cyste-3, was then purified by HPLC.

Recombinant Protein Expression and Purification: The recombinant anti-apoptotic proteins, BFL-1ΔC (aa 1-153), MCL-1ΔNΔC (aa 170-327) and BCL-X$_L$ΔC (aa 1-212) were cloned into the pET19b (Novagen: BFL-1ΔC) or pGEX-4T-1 (GE Healthcare; MCL-1ΔNΔC, BCL-X$_L$ΔC) expression vectors, expressed in *Escherichia coli* BL21(DE3), and purified by sequential affinity and size exclusion chromatography as described (Pitter et al., *Methods Enzymol.*, 446, 387-408 (2008)) and detailed below.

cDNA encoding BFL-1ΔC (aa 1-153) was cloned into the pET19b expression vector (Novagen) followed by DNA sequencing to verify the construct. Constructs bearing cysteine to serine mutations were created by PCR-based site-directed mutagenesis (QuikChange Mutagenesis Kit, Stratagene). Transformed *Escherichia coli*BL21(DE3) LOBSTR (Andersen et al., 2013) (#EC1001, Kerafast) were cultured in ampicillin-containing Luria broth (LB) and protein expression induced with 0.5 mM isopropyl β-D-1-thiogalactopyranoside (IPTG) overnight at 16° C. Bacterial pellets were resuspended in 20 mM Tris pH 7.5, 250 mM NaCl, and two complete protease inhibitor tablets (Roche), and then microfluidized (M-110L, Microfluidics) and centrifuged at 45,000×g for 1 h. The supernatant was passed over a Ni-NTA (Qiagen) column equilibrated with 50 mM Tris pH 7.5, 250 mM NaCl. The column was sequentially washed with 25 mL of equilibration buffer containing 5 mM, 10 mM and 20 mM imidazole, and then His-BFL-1ΔC was eluted in equilibration buffer containing 300 mM imidazole. The fraction containing His-BFL-1ΔC was dialyzed against 50 mM Tris pH 8, 100 mM NaCl at 4° C. and then concentrated and loaded onto a Superdex S-75 (GE Healthcare) gel filtration column equilibrated with 50 mM Tris pH 8.0, 100 mM NaCl. The column was washed with 30 mL equilibration buffer and fractions containing His-BFL-1ΔC were pooled and analyzed both by SDS-PAGE electrophoresis/ Coomassie stain and anti-BFL-1 (Abcam, #125259) and anti-His (Abcam, #18184) western blotting. Purified protein was then concentrated, flash frozen using liquid nitrogen, and stored at −80° C. until use.

MCL-1ΔNΔC (aa 170-327) and BCL-X$_L$ΔC (aa 1-212) constructs were cloned into pGEX-4T-1 (GE Healthcare) followed by DNA sequencing to verify the constructs. Transformed *Escherichia coli* BL21(DE3) (Sigma-Aldrich) were cultured in ampicillin-containing LB, and protein expression induced with 0.5 mM IPTG and grown for 4 h at 37° C. Bacterial pellets were resuspended in phosphate-buffered saline (PBS), 0.1% Triton X-100, and complete protease inhibitor tablet (Roche), and then microfluidized and centrifuged at 45,000×g for 1 h. Supernatants were passed over a glutathione sepharose (GE Healthcare) column equilibrated with PBS containing 0.1% Triton X-100. The column was sequentially washed with 25 mL of PBS containing 0.1% Triton X-100 and PBS, and then GST cleaved on-resin with thrombin (Sigma) overnight at 25° C. The GST-free protein was eluted with PBS, concentrated, and loaded onto a Superdex S-75 (GE Healthcare) gel filtration column equilibrated with 50 mM Tris pH 7.4, 150 mM NaCl. The column was washed with 30 mL equilibration buffer and fractions containing MCL-1ΔNΔC or BCL-X$_L$ΔC were pooled and analyzed by SDS-PAGE electrophoresis and Coomassie staining. For GST-MCL-1ΔNΔC purification, protein was eluted from the column using 50 mM Tris, pH 8.0, 10 mM GSH, concentrated, and purified by size exclusion chromatography using a Superdex S-75 gel filtration column, as described above. Purified proteins were concentrated, flash frozen using liquid nitrogen, and stored at −80° C.

Biolayer Interferometry: Binding analyses of NOXA peptide interactions with BFL-1ΔC were performed on an Octet RED384 system (Fortebio, Menlo Park, CA) at 30° C. Super streptavidin (SSA) tips were prewetted in 1× kinetics buffer (PBS, pH 7.4, 0.01% BSA, 0.002% Tween-20) and then conjugated to NOXA SAHBs bearing an N-terminal biotin-PEG linker (10 μg/mL). Excess streptavidin was quenched by incubation with 2 μg/mL biocytin. The tips were then washed with kinetics buffer and soaked in a serial dilution of BFL-1ΔC for 10 min to measure association rate, followed by a 15 min incubation in kinetics buffer to measure dissociation rate. Dissociation constants were calculated using Octet Data Analysis version 9.0.

In Vitro Covalent Conjugation Assay: BFL-1ΔC constructs (40 μM) were combined with NOXA SAHB$_A$ or NOXA SAHB$_A$ C25S (120 μM) and 10 mM DTT in 50 mM Tris pH 8.0, 100 mM NaCl (final volume, 5 μL), and then incubated in the dark for 1 h at room temperature (RT). After this incubation in a reducing environment, the mixture was diluted 5-fold into 50 mM Tris pH 8.0, 100 mM NaCl, 12 mM GSSG and incubated in the dark for an additional 30 min at RT. The samples were then boiled in 4× loading buffer lacking DTT and electrophoresed on 12% Bis-Tris gel. The gel was rinsed with water, subjected to FITC scan (Typhoon FLA 9500, GE Healthcare) and then Coomassie staining.

For warhead-bearing SAHBs, His-BFL-1ΔC C4S/C19S protein was pretreated with 10 mM DTT in 50 mM Tris pH 8.0, 100 mM NaCl for 30 min at RT (final volume, 9.5 μL), and then combined with a 10:1 molar ratio of NOXA SAHBA or BIM SAHBA peptides bearing warheads 1-8 (final volume, 10 μL) for an additional 2 h incubation at RT. Processing for gel electrophoresis and Coomassie staining was performed as above.

Streptavidin Pull-down: Recombinant His-BFL-1ΔC, BCL-X$_L$ΔC (tagless) and GST-MCL-1ΔNΔC (1 μM each) were combined and reduced with 3 mM DTT in PBS for 30 min at RT, and then incubated with 1 μM biotinylated SAHB$_A$, SAHB$_A$-3 or vehicle for 4 h at RT. The mixtures were then combined with PBS-washed high-capacity SA agarose (Thermo Fisher Pierce) and incubated with rotation for 2 h at RT. The beads were centrifuged at 3000 rpm, washed twice with NP-40 lysis buffer (1% NP40, 50 mM Tris pH 8.0, 100 mM NaCl, 2.5 mM MgCl$_2$), once with PBS, and then bound protein eluted by boiling in 10% SDS containing 10 mg/mL biotin. Inputs (10%) and eluates were electrophoresed on a 12% Bis-Tris gel and then subjected to silver stain and imaging.

Liposomal Release Assay: Liposomal release assays were performed as detailed below, with SAHB$_A$-3/BFL-1ΔC conjugates prepared by treating BFL-1ΔC (10 μM) with DTT (20 mM) for 30 min at 4° C., followed by sequential incubation with NOXA SAHB$_A$-3 or BIM SAHB$_A$-3 peptides at peptide:protein molar ratios of 1.2×, 0.75×, and 0.5× for 1 h each at 4° C.

Large unilamellar vesicles (LUVs) with encapsulated ANTS and DPX were generated and purified as described (Leshchiner et al., 2013; Lovell et al., 2008). The indicated combinations of BAX (400 nM), tBID (40 nM), and BFL- 1ΔC or SAHB$_A$-3/BFL-1ΔC conjugates (1.5 μM), were added to liposomes (5 μL) in 384 well plates (final volume, 30 μL), and released fluorophore was measured over 120 min using an M1000 Infinite plate reader (Tecan) with excitation and emission wavelengths of 355 nm and 520 nm, respectively. SAHB$_A$-3/BFL-1ΔC conjugates were prepared by treating BFL-1ΔC (10 μM) with DTT (20 mM) for 30 min at 4° C., followed by sequential incubation with NOXA SAHB$_A$-3 or BIM SAHB$_A$-3 peptides at peptide:protein molar ratios of 1.2×, 0.75×, and 0.5× for 1 h each at 4° C. Conjugation efficiency was confirmed by 12% Bis-Tris gel electrophoresis and Coomassie staining. The protein conjugate was then concentrated to 75 μM, loaded onto a Superdex S-75 (GE Healthcare) gel filtration column equilibrated with 20 mM HEPES pH 7.5, 300 mM NaCl, 1 mM DTT, washed with 30 mL equilibration buffer, and fractions collected, analyzed by SDS-PAGE electrophoresis, and used fresh in liposomal assays. Percent ANTS/DPX release was calculated as $[(F-F0)/(F100-F0)] \times 100$, where F0 is baseline fluorescence at time 0, F is the fluorescence recorded for each time point, and F100 is the maximum amount of ANTS/DPX release based on liposomal treatment with 1% Triton X-100.

BFL-1 Targeting in Lysates and Cells: A series of NOXA and BIM SAHB constructs, with and without installed biotin handles and/or acrylamide warheads, were employed in comparative BFL-1 targeting assays in lysates containing or intact cells expressing HA-BFL-1ΔC C4S/C19S (transfected 293T cells) or native BFL-1 (A375P), performed as described in detail below.

293T cells were maintained in DMEM containing 10% FBS and penicillin/streptomycin, and transfections performed with 2 μg pCMV plasmid containing HA-BFL-1ΔC C4S/C19S using X-tremeGENE 9 (Roche). For lysate experiments, cells were trypsinized 24 hours post-transfection, washed with PBS, and lysed by incubation with 1% CHAPS lysis buffer (150 mM NaCl, 50 mM Tris pH 7.4, 100 mM DTT). Protein concentration of the soluble fraction was measured using a BCA kit according to manufacturer's instructions (Thermo Scientific). Biotinylated NOXA SAHB$_A$-3 or BIM SAHB$_A$-3 (10 μM) was added to 100 μg of lysate and incubated at RT for 2 h. Samples were then boiled in LDS buffer and subjected to western analysis using 1:1000 dilutions of HA (Sigma-Aldrich, #12CA5) and biotin (Abcam, #53494) antibodies. To evaluate the capacity of biotinylated SAHBs to compete with tBID for interactions with BFL-1 and MCL-1, 293T cells were transfected with either HA-BFL-1ΔC C4S/C19S or FLAG-MCL-1 in the p3×FLAG-CMV-10 vector (Sigma) as above. After 24 h, cells were trypsinized, washed with PBS, lysed in 1% CHAPS buffer, and the supernatant collected for protein concentration determination by BCA kit. Lysate samples (0.5 mg) were incubated with 0.25 μM recombinant tBID (R&D Systems) and 5 μM biotinylated BIM SAHB$_A$ or BIM SAHB$_A$-3 for 6 h at RT. The mixtures were then subjected to HA or FLAG (Sigma-Aldrich, F7425) immunoprecipitation, followed by western analysis using 1:1000 dilutions of HA, FLAG, biotin, and BID (Santa Cruz sc-11423) antibodies. For HA-immunoprecipitation from 293T cells treated with biotinylated peptides, cells were transfected with HA-BFL-1ΔC C4S/C19S as above and, after 24 hours, incubated with 20 μM biotinylated BIM SAHB$_A$ or BIM SAHB$_A$-3 in DMEM containing 5% FBS for 6 hours. Cells were harvested and lysed as above, and incubated overnight with anti-HA agarose beads (Pierce). The beads were washed 3 times with lysis buffer, eluted by boiling in LDS buffer, and subjected to western analysis with HA and biotin antibodies. For 293T treatment with non-biotinylated SAHBs, cells were transfected with HA-BFL-1ΔC C4S/C19S as above, incubated with 20 μM BIM SAHB$_A$ or BIM SAHB$_A$-3 in DMEM containing 5% FBS, and lysates harvested as above at the indicated time points for western analysis using the HA and actin antibodies. For A375P melanoma studies, cells were maintained in DMEM containing 10% FBS and penicillin/streptomycin, and biotinylated NOXA SAHB$_A$-3 or BIM SAHB$_A$-3 (30 μM) was added to 1 mg of lysate, followed by overnight incubation in CHAPS lysis buffer at 4° C. Biotin capture was accomplished by incubating the mixture with high-capacity SA agarose (Thermo Scientific) for 2 h at 4° C., followed by centrifugation and washing the pelleted beads with 3×1 mL lysis buffer. Bead-bound proteins were eluted by boiling in 10% SDS containing 10 mg/mL biotin for 10 min and then subjected to electrophoresis and western blotting using BF1-1 (Abcam, #125259) and MCL-1 (Rockland, #600-401-394S) antibodies.

Cell Viability, LDH Release, and Caspase-3/7 Activation Assays: Cancer cells were cultured using their standard culture media containing 10% FBS and penicillin/streptomycin (A375P: DMEM; SK-MEL-2, SK-MEL-28 and MCF-7: EMEM; A549, H929: RPMI). Cells were plated in 96-well plates ($5 \times 10^3$ cells per well) and, after overnight incubation, treated with the indicated concentrations of BIM SAHB$_{A1}$ or BIM SAHB$_A$-3 in the corresponding media supplemented with 5% FBS for the indicated durations. Cell viability and caspase 3/7 activation was measured using CellTiter-Glo and Caspase-Glo 3/7 chemiluminescence reagents (Promega), respectively, and luminescence detected by a microplate reader (Spectramax M5, Molecular Devices). LDH release was quantified after 30 min peptide incubation by plate centrifugation at 1500 rpm for 5 min at 4° C., transfer of 100 μL cell culture media to a clear plate (Corning), incubation with 100 μL LDH reagent (Roche) for 30 min while shaking, and measurement of absorbance at 490 nm on a Spectramax M5 microplate reader.

Mitochondrial Cytochrome c Release and Biotinylation Assays: A375P cells were plated in 6-well Corning plates ($3 \times 10^5$ cells/well) and cultured as above. After 24 h, the cells were treated with BIM SAHB$_{A1}$ or BIM SAHB$_A$-3 (40 μM) in DMEM containing 5% FBS for the indicated durations, and then trypsinized, washed with PBS, and cytosol (supernatant) and mitochondrial (pellet) fractions isolated as described (Dewson, 2015). Briefly, pelleted cells were resuspended at $1 \times 10^7$ cells/mL in permeabilization buffer (20 mM HEPES/KOH PH 7.5, 250 mM sucrose, 50 mM KCl, 2.5 mM MgCl$_2$) supplemented with 0.025% digitonin and protease inhibitors, followed by incubation on ice for 10 min and centrifugation at 13,000 g. The resultant supernatant and pellet fractions were boiled in LDS buffer and subjected to western analysis using a 1:1000 dilution of cytochrome c antibody (BD Pharmingen #556433). For biotinylation studies, A375P mitochondria were isolated as above, resuspended in permeabilization buffer, and then treated with biotinylated BIM SAHB$_A$ or BIM SAHB$_A$-3 (50 μM) for 4 h at RT. Samples were then boiled in LDS buffer and subjected to western analysis using 1:1000 dilutions of BFL1 (Abcam #125259), biotin (Abcam, #53494), and VDAC1 (Abcam #14734) antibodies.

Confocal Microscopy: A375P cells were plated in chambered coverglass ($1.5 \times 10^4$ cells/well) and cultured as above. After 24 h, cells were treated with FITC-BIM SAHB$_{A1}$ or BIM SAHB$_A$-3 (1 μM) for 4 h in phenol-free DMEM containing 5% FBS. Cells were washed, stained with MitoTracker Red (Thermo), Hoechst 33342, and imaged live. Confocal images were collected with a Yokogawa CSU-X1 spinning disk confocal (Andor Technology) mounted on a Nikon Ti-E inverted microscope (Nikon Instruments). Images were acquired using a 100× 1.4 NA Plan Apo objective lens with an Orca ER CCD camera (Hamamatsu Photonics) and 488 nm laser. Acquisition parameters, shutters, filter positions and focus were controlled by Andor iQ software (Andor Technology).

Cellular Uptake of Stapled Peptides: To evaluate cellular uptake of biotinylated SAHBs by biotin western analysis of electrophoresed lysates from treated cells, 293T cells were plated in 6-well Corning plates ($2 \times 10^5$ cells/well) in DMEM containing 10% FBS and penicillin/streptomycin. After 24 h, biotinylated NOXA SAHB$_A$-3 or BIM SAHB$_A$-3 peptides (20 µM) were added to the cells in DMEM containing 5% FBS for an additional 24 h incubation. The cells were then trypsinized to remove any surface-bound peptide, washed with PBS, lysed as above in 1% CHAPS lysis buffer, and the supernatant collected for protein concentration determination by BCA kit according to manufacturer's instructions (Thermo Scientific). Cellular lysate samples (50 µg) were boiled in LDS buffer and subjected to western analysis using a 1:1000 dilution of anti-biotin (Abcam, #53494) and 1:2000 dilution of anti-actin (Sigma-Aldrich, #A1978) antibodies. To evaluate the potential effect of transfection conditions on stapled peptide uptake, 293T cells were plated in 6-well Corning plates ($2 \times 10^5$ cells/well) and cultured as above. After 24 h, a mock transfection was performed with X-tremeGENE 9 (Roche) and no plasmid alongside control cells that were not transfected. After an addition 24 hour incubation, 20 µM biotinylated BIM SAHB$_A$-3 peptide was added to the cells in DMEM containing 5% FBS and incubated for 4 h. Cells were then washed, trypsinized, and lysed as above, and lysates subjected to biotin and actin western analyses. For cellular uptake analysis by ImageXpress high-content epifluorescence microscopy, the indicated cell lines were plated in black, clear bottom 96-well plates overnight at a density of $1.5 \times 10^4$ cells per well for MEFs or $1 \times 10^4$ cells per well for A375P cells in DMEM supplemented with 10% FBS, 1% penicillin/streptomycin, and 1% glutamine. The following day, cells were treated with the FITC-labeled peptides or the equivalent amount of vehicle (0.1% DMSO) for 4 h in DMEM supplemented with 5% FBS, and then stained with Hoechst 33342 and Cell-Mask Deep Red (CMDR, Invitrogen) for 10 min. The media was then aspirated and cells fixed with 4% (wt/vol) paraformaldehyde for 10 min, followed by washing three times with PBS and an imaging by ImageXpress Microscopy (Molecular Devices). Data were collected for five sites per well at 20× magnification, with each treatment performed in triplicate, and then analyzed and quantified using MetaXpress software. The CMDR stain was used to visualize the boundaries of the cell and to create a mask for measuring FITC-peptide inside the cell, thereby excluding fluorescent debris from the analysis. A custom module in MetaXpress was applied to incrementally recede the CMDR image mask from the cellular border, further restricting the analyzed FITC signal to internalized peptide. The measurement of Total Internalized Fluorescence Intensity (TIFI) represents the level of absolute fluorescence detected per cell, per peptide construct. Maximum and minimum thresholding was utilized to exclude FITC and Cy5 outliers that were much larger and brighter than average, and total intensity and average intensity per cell thresholds were set such that vehicle-treated cells scored negative by the analysis.

Statistical Analysis: Datasets were analyzed by two-tailed Student's t test, with $p < 0.05$ considered statistically significant.

Example 9: Cytomegalovirus Stapled Peptides for Covalent Targeting of BAX

FIG. 19 depicts the structure of an inhibitor peptide found in cytomegalovirus. Distances between reactive sulfur of Cys-126 in BAX and alpha carbons of selective residues in the peptides are shown. Most relevant are distance between His-140 of 9.3 Ang and Ala-136 of 9.4 Ang. Given these distances, a relatively short amino acid linker such as Diaminobutyric acid (Dab) or Diaminopropanoic acid (Dpr) (5 or 6 Ang) combined with an electrophile such as nipecotic acid, homoproline or proline (4-5 Ang) (see Tables 1 and 2, above) could span the 9 Ang needed to precisely place the electrophile with atomic precision next to the nucleophilic Cysteine allowing the formation of a covalent bond upon interaction of the peptides. Exemplary peptides (SEQ ID NOs.: 9-21) of viral Mitochondria-localized Inhibitor of Apoptosis (vMIA) of cytomegalovirus for covalent targeting for modulation (e.g., inhibition) of BAX are shown in FIG. 19.

Figure 20:
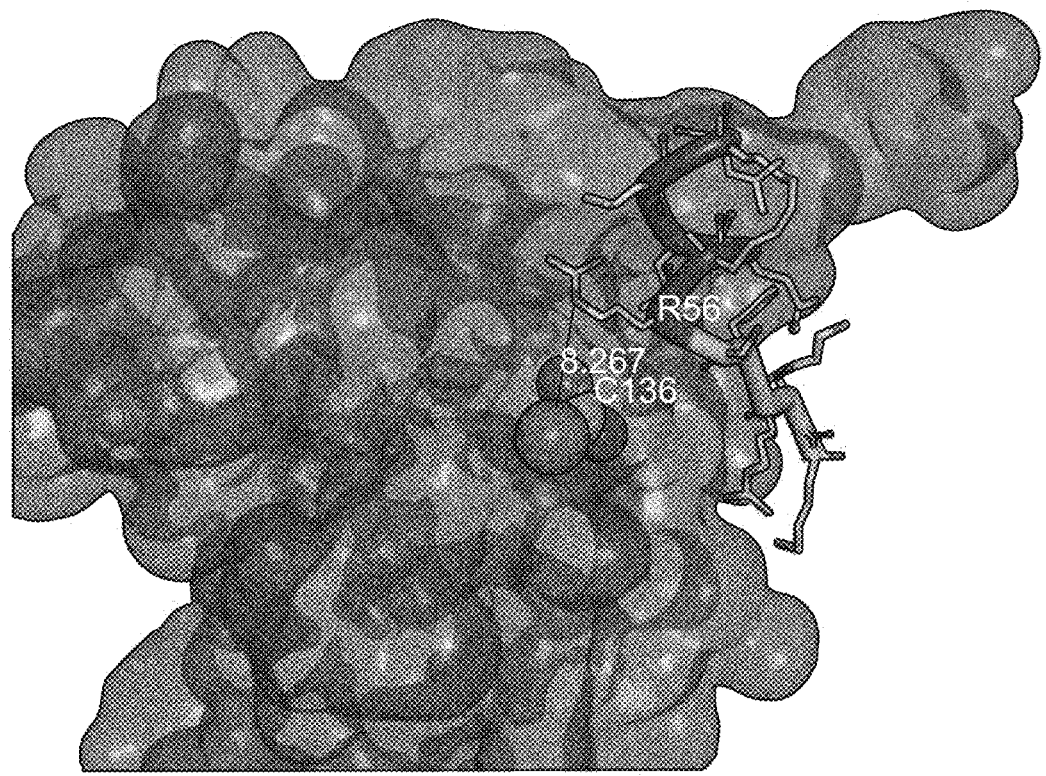
FIG. 20: Depicts the structure of eiF4E bound to an inhibitor peptide found in eiF4G. The structure is annotated with protein target cysteine residue number and the proximal helix residue number, and distance in Angstroms. The figure also provides amino acid sequences of exemplary stapled peptides of eiF4G for covalent targeting for modulation (e.g., inhibition) of eiF4E. J=non-natural electrophile containing amino acid (note however that the electrophile can be linked to the peptide through an entity other than an amino acid); 8=R-octenyl alanine; X=S-pentenyl alanine.

Example 10: Stapled eiF4G Peptides for Covalent Modification of eiF4E eIF4E is Over-Expressed in Several Cancers and Causes Increased Translation of oncogenic proteins by deregulated cap-dependent translation. Inhibitors of the eiF4E:eiF4G interactions (see FIG. 20) provide a route to normalizing cap-dependent translation. Stapled peptides (SEQ ID NOs.: 22-23) can target this protein: protein interactions and be used for covalent targeting for modulation (e.g., inhibition) of eiF4e.

Example 11: Stapled Mediator of RNA Polymerase II Transcription Subunit 11 (Med11) Peptides for Covalent Modulation of Mediator of RNA Polymerase II Transcription Subunit 22 (Med22)

RNA polymerase (Pol) II-mediated transcription requires the coactivator complex Mediator. Mediator links the transcriptional regulators and Pol II, and is connected with human disease. Mediator comprises 25 subunits that form the head, middle, tail and kinase modules. The head module constitutes one-half of the essential Mediator core, and comprises the conserved subunits Med6, Med8, Med11, Med17, Med18, Med20 and Med22. Stapled Mediator of RNA polymerase II transcription subunit 11 peptides (SEQ ID NOs.: 24-33; see FIG. 21) can be used for covalent targeting for modulation (e.g., inhibition) of Mediator of RNA polymerase II transcription subunit 22.

Example 12: Stapled FAS Ligand Peptides for Covalent Targeting of FADD

The death inducing signaling complex (DISC) formed by Fas receptor, Fas-associated death domain protein (FADD) and caspase 8 is a critical trigger of apoptosis. The Fas-FADD DISC represents a receptor platform, which once assembled initiates the induction of programmed cell death. A highly oligomeric network of homotypic protein interactions comprised of the death domains of Fas and FADD is at the center of DISC formation. Stapled FAS ligand peptides (SEQ ID NOs:34-45; FIG. 22) can be used for covalent targeting for modulation (e.g., inhibition) of FADD.

Figure 23:
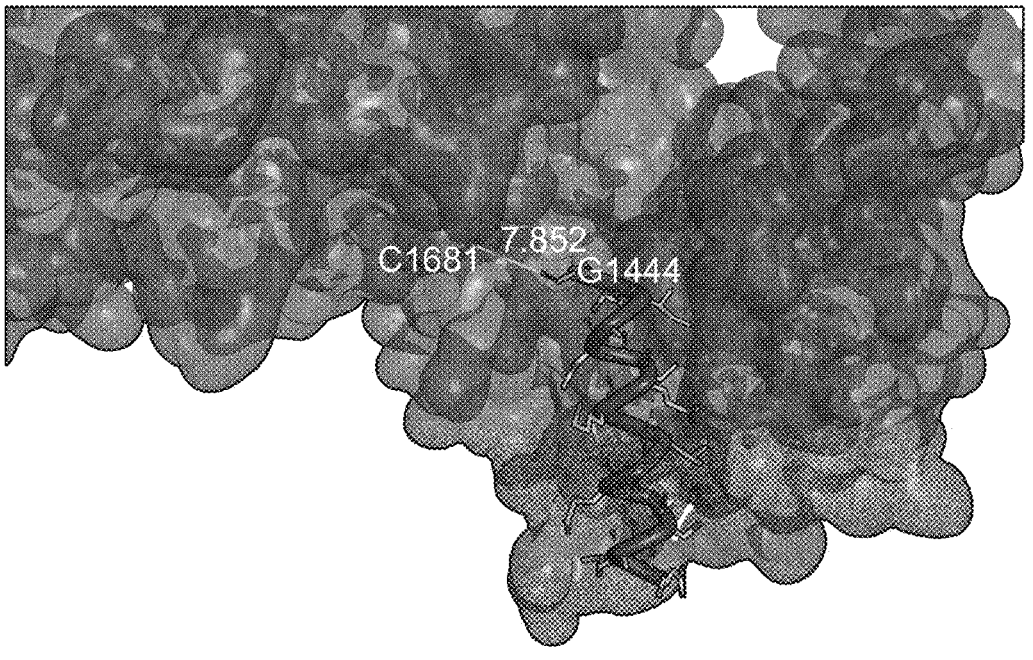
FIG. 23: Depicts the structure of a netrin receptor deleted in colorectal cancer (DCC) peptide bound to the myosin tail homology 4 (MyTH4)-FERM domain. The structure is annotated with protein target cysteine residue number and the proximal helix residue number, and distance in Angstroms. The figure also provides amino acid sequences of exemplary stapled Netrin receptor DCC peptides for covalent targeting for modulation (e.g., inhibition) of Myosin-X.

Example 13: Stapled Netrin Receptor DCC Peptides for Covalent Targeting of Myosin-X Myosin-X is an important and unconventional myosin that is crucial for cargo transportation to filopodia tips and is also used in spindle assembly by interacting with microtubules. FIG. 23 shows the structure of the myosin-X tail domain cassette, consisting of myosin tail homology 4 (MyTH4) and FERM domains in complex with its specific cargo, a netrin receptor deleted in colorectal cancer (DCC). Stapled Netrin receptor DCC peptides (SEQ ID NOs.: 46-49) can be employed for covalent targeting for modulation (e.g., inhibition) of Myosin-X.

Example 14: Stapled eIF4A Peptides for Covalent Targeting of PDCD4

Tumor suppressor programmed cell death protein 4 (PDCD4) inhibits the translation initiation factor eIF4A, an RNA helicase that catalyzes the unwinding of secondary structure at the 5'-untranslated region of mRNAs and controls the initiation of translation. Stapled eIF4A peptides (SEQ ID NOs.: 51-56; FIG. 24) can be utilized for covalent targeting for modulation (e.g., inhibition) of PDCD4.

Example 15: Stapled RASSF1 Peptides for Covalent Targeting of DAXX

DAXX is a scaffold protein with diverse roles including transcription and cell cycle regulation. The N-terminal residues of the tumor suppressor Rassf1C fold into an amphipathic alpha helix upon binding the C-terminal half of DAXX that is intrinsically disordered and which forms a left-handed four-helix bundle (H1, H2, H4, H5) via a shallow cleft along the flexible helices H2 and H5. Stapled RASSF1 peptides (SEQ ID NOs.: 57-61; FIG. 25) can be used for covalent targeting for modulation (e.g., inhibition) of DAXX.

Example 16: Stapled p53 Peptides for Covalent Targeting of p300

Coactivators CREB-binding protein and p300 play important roles in mediating the transcriptional activity of p53. The N-terminal transactivation domain of p53 forms a short alpha helix and interacts with the Taz2 (C/H3) domain of p300 through an extended surface (FIG. 26). Stapled p53 peptides (SEQ ID NOs.: 63-67) can be employed for covalent targeting for modulation (e.g., inhibition) of p300.

Example 17: Stapled Peptides for Covalent Targeting of Tryptophanyl-tRNA Synthetase Human tryptophanyl-tRNA synthetase (TrpRS) is secreted into the extracellular region of vascular endothelial cells. Deletion of the tRNA anticodon-binding (TAB) domain insertion, consisting of eight residues in the human TrpRS, abolished the enzyme's apoptotic activity for endothelial cells, whereas its translational catalysis and cell-binding activities remained unchanged. Stapled peptides (SEQ ID NOs.: 69-75; FIG. 27) can be used for covalent targeting for modulation (e.g., inhibition), and dimer disruption, of tryptophanyl-tRNA synthetase.

Example 18: Stapled SOS Peptides for Covalent Targeting of RAS

Human H-Ras complexes with the Ras guanine-nucleotide-exchange-factor region of the Son of sevenless (Sos) protein. The normally tight interaction of nucleotides with Ras is disrupted by Sos in two ways. First, the insertion into Ras of an alpha-helix from Sos results in the displacement of the Switch 1 region of Ras, opening up the nucleotide-binding site. Second, side chains presented by this helix and by a distorted conformation of the Switch 2 region of Ras alter the chemical environment of the binding site for the phosphate groups of the nucleotide and the associated magnesium ion, so that their binding is no longer favored. Stapled SOS peptides (SEQ ID NOS.: 76-117; FIGS. 28 and 29) can be used for covalent targeting for modulation (e.g., inhibition) of RAS.

Methods for Examples 9-18

A progressive and iterative strategy modeled on the above Bfl-1 validation study is employed to identify the ideal placement and location of the electrophilic warhead, establish that it reacts covalently with the target protein, certify that the electrophilic stapled peptide reacts specifically with the target protein in cells, determine the cellular phenotype of cells having a covalently modified target protein, substantiate this phenotype by probing downstream signaling pathways or effector proteins, and finally demonstrating the in vivo efficacy of this electrophilic stapled peptide in a relevant animal model.

Specifically the following steps are undertaken:

Synthesis of Stapled Peptides Bearing Electrophilic Warheads: Hydrocarbon-stapled peptides corresponding to the identified target-interacting alpha-helical domain is synthesized using the above-described methods and techniques. The electrophilic warhead is placed at discrete positions in the peptide sequence, including at the N- or C-termini, or other positions within the peptide backbone as guided, when available, by structural information. When the warhead is not positioned at the N-terminus, the electrophile is linked to the peptide using an orthogonally protected Lysine or similar amino functionalized Lysine analog such as ornithine, diaminobutanoic acid, or diaminopropionic acid, where the orthogonal protecting group is, for example, Mtt or ivDde. Once the peptide synthesis is complete, olefin metathesis is conducted as per our above-described procedures and the N-term or side chain amino group is unmasked and a cyclic amino acid, such as proline or a homoproline analog, is incorporated as a linker between the stapled peptide and the electrophile. The electrophile can be incorporated to the unmasked amine as a carboxylic acid using established coupling chemistries. Distinct acrylamide or substituted acrylamides are incorporated as well as distinct cyclic amino acids or substituted benzene rings serving as the linker, and finally different locations or lengths of the amino-functionalized amino acid or N-terminally located linker/electrophile yield a panel of stapled peptides for evaluation of covalent target protein engagement. A final variable is staple location, whereby, the staple is positioned so as to maximize alpha-helical enhancement, target binding affinity and cellular penetrance so as to generate and identify lead stapled peptides bearing electrophilic warheads.

Recombinant Protein Expression and Purification: The recombinant target protein, its analogs, mutants, or closely related proteins are cloned into expression vectors, such as the bacterial expression vectors pET19b (Novagen) or pGEX-4T-1 (GE Healthcare), transformed into in *Escherichia coli* BL21(DE3), and expression induced and then protein purified by sequential affinity and size exclusion chromatography.

In Vitro Covalent Conjugation Assay: For electrophilic stapled peptides, target protein is pretreated with 10 mM DTT in 50 mM Tris pH 8.0, 100 mM NaCl for 30 min at RT (final volume, 9.5 µL), and then combined with a 10:1 molar ratio of electrophilic stapled peptides bearing distinct warheads or distinct locations of the warhead or staple (final volume, 10 µL) for an additional 2 h incubation at RT. The samples were then boiled in 4× loading buffer and electrophoresed on 12% Bis-Tris gel. The gel is rinsed with water and subjected to Coomassie staining.

Streptavidin Pull-down: Recombinant protein (1 µM) is reduced with 3 mM DTT in PBS for 30 min at RT, and then incubated with 1 µM biotinylated peptide (synthesized explicitly for this purpose by incorporating Lys(biotin) at the C-terminus of the peptides) for 4 h at RT. The mixtures are combined with PBS-washed high-capacity SA agarose (Thermo Fisher Pierce) and incubated with rotation for 2 h at RT. The beads are centrifuged at 3000 rpm, washed twice with NP-40 lysis buffer (1% NP40, 50 mM Tris pH 8.0, 100 mM NaCl, 2.5 mM MgCl2), once with PBS, and then bound protein eluted by boiling in 10% SDS containing 10 mg/mL biotin. Inputs (10%) and eluates are electrophoresed on a 12% Bis-Tris gel and then subjected to silver stain and imaging.

In Vitro Biochemical Activity Assay: An activity-tailored assay is performed using established techniques to demonstrate that covalent modification of the target protein impairs or possibly enhances the activity of the target protein in this in vitro activity assay, as exemplified above by a liposomal release to gauge target protein-inhibition of poration.

Protein Targeting in Lysates and Cells: A series of electrophilic stapled peptide constructs, with and without installed biotin handles and/or acrylamide warheads, are employed in comparative protein targeting assays in lysates containing, or intact cells expressing, HA-tagged versions of the target protein (transfected 293T cells) or in an identified cell line containing the relevant native protein.

Cell Activity Testing: The functional consequences of electrophilic stapled peptide engagement of a target protein in cells are assessed by tailored cellular read-out assays. For phenotypic read-outs of target proteins involved in regulating apoptosis induction or cell killing, for example, cancer cells are cultured using their standard culture media containing 10% FBS and penicillin/streptomycin. Cells are plated in 96-well plates ($5 \times 10^3$ cells per well) and, after overnight incubation, treated with the indicated concentrations of electrophilic stapled peptide in the corresponding media supplemented with 5% FBS for the indicated durations. Cell viability and caspase 3/7 activation are measured using CellTiter-Glo and Caspase-Glo 3/7 chemiluminescence reagents (Promega), respectively, and luminescence detected by a microplate reader (Spectramax M5, Molecular Devices). LDH release is quantified after 30 min peptide incubation by plate centrifugation at 1500 rpm for 5 min at 4° C., transfer of 100 mL cell culture media to a clear plate (Corning), incubation with 100 mL LDH reagent (Roche) for 30 min while shaking, and measurement of absorbance at 490 nm on a Spectramax M5 microplate reader.

Confocal Microscopy: To identify the intracellular location of electrophilic stapled peptides, cells are plated in chambered coverglass ($1.5 \times 10^4$ cells/well) and cultured as above. After 24 h, cells are treated with FITC-derivatized peptide (1 µM) for 4 h in phenol-red free DMEM containing 5% FBS. Cells are washed, stained with MitoTracker Red (Thermo), Hoechst 33342, and imaged live. Confocal images are acquired with a Yokogawa CSU-X1 spinning disk confocal (Andor Technology) mounted on a Nikon Ti-E inverted microscope (Nikon Instruments). Images are acquired using a 100× 1.4 NA Plan Apo objective lens with an Orca ER CCD camera (Hamamatsu Photonics) and 488 nm laser. Acquisition parameters, shutters, filter positions and focus are controlled by Andor iQ software (Andor Technology).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

SEQUENCE LISTING

```
Sequence total quantity: 187
SEQ ID NO: 1              moltype = AA  length = 25
FEATURE                   Location/Qualifiers
source                    1..25
                          mol_type = protein
                          organism = synthetic construct
SEQUENCE: 1
AELEVESATQ LRRFGDKLNF RQKLL                                    25

SEQ ID NO: 2              moltype = AA  length = 26
FEATURE                   Location/Qualifiers
source                    1..26
                          mol_type = protein
                          organism = synthetic construct
SEQUENCE: 2
DMPREIWIAQ ELRRIGDEFN AYYARR                                   26

SEQ ID NO: 3              moltype = AA  length = 27
FEATURE                   Location/Qualifiers
source                    1..27
                          mol_type = protein
                          organism = synthetic construct
SEQUENCE: 3
```

-continued

```
QDASTKKLSE SLKRIGDELD SNMELQR                                         27

SEQ ID NO: 4           moltype = AA  length = 34
FEATURE                Location/Qualifiers
source                 1..34
                       mol_type = protein
                       organism = synthetic construct
SEQUENCE: 4
SSTMGQVGRQ LAIIGDDINR RYDSEFQTML QHLQ                                 34

SEQ ID NO: 5           moltype = AA  length = 25
FEATURE                Location/Qualifiers
source                 1..25
                       mol_type = protein
                       organism = synthetic construct
SEQUENCE: 5
PGGRLAEVST VLLRLGDELE QIRPS                                           25

SEQ ID NO: 6           moltype = AA  length = 29
FEATURE                Location/Qualifiers
source                 1..29
                       mol_type = protein
                       organism = synthetic construct
SEQUENCE: 6
SESQEDIIRN IARHLAQVGD SMDRSIPPG                                       29

SEQ ID NO: 7           moltype = AA  length = 33
FEATURE                Location/Qualifiers
source                 1..33
                       mol_type = protein
                       organism = synthetic construct
SEQUENCE: 7
EEEQWAREIG AQLRRMADDL NAQYERRRQE EQQ                                  33

SEQ ID NO: 8           moltype = AA  length = 30
FEATURE                Location/Qualifiers
source                 1..30
                       mol_type = protein
                       organism = synthetic construct
SEQUENCE: 8
KKFEPKSGWM TFLEVTGKIC EMLSLLKQYC                                      30

SEQ ID NO: 9           moltype = AA  length = 21
FEATURE                Location/Qualifiers
source                 1..21
                       mol_type = protein
                       organism = synthetic construct
SEQUENCE: 9
CEALKKALRR HRFLWQRRQR A                                               21

SEQ ID NO: 10          moltype = AA  length = 20
FEATURE                Location/Qualifiers
VARIANT                6
                       note = Non-natural electrophile containing amino acid or
                        not present
source                 1..20
                       mol_type = protein
                       organism = synthetic construct
SEQUENCE: 10
EALKKALRRH RFLWQRRQRA                                                 20

SEQ ID NO: 11          moltype = AA  length = 20
FEATURE                Location/Qualifiers
VARIANT                10
                       note = Non-natural electrophile containing amino acid or
                        not present
source                 1..20
                       mol_type = protein
                       organism = synthetic construct
SEQUENCE: 11
EALKKALRRA RFLWQRRQRA                                                 20

SEQ ID NO: 12          moltype = AA  length = 20
FEATURE                Location/Qualifiers
VARIANT                14
                       note = Non-natural electrophile containing amino acid or
                        not present
source                 1..20
                       mol_type = protein
```

-continued

```
                        organism = synthetic construct
SEQUENCE: 12
EALKKALRRH RFLAQRRQRA                                              20

SEQ ID NO: 13           moltype = AA   length = 14
FEATURE                 Location/Qualifiers
MOD_RES                 3
                        note = S-pentenyl alanine
VARIANT                 4
                        note = Non-natural electrophile containing amino acid or
                         not present
MOD_RES                 7
                        note = S-pentenyl alanine
source                  1..14
                        mol_type = protein
                        organism = synthetic construct
SEQUENCE: 13
LKAALRAHRF LWQR                                                    14

SEQ ID NO: 14           moltype = AA   length = 14
FEATURE                 Location/Qualifiers
MOD_RES                 3
                        note = S-pentenyl alanine
MOD_RES                 7
                        note = S-pentenyl alanine
VARIANT                 8
                        note = Non-natural electrophile containing amino acid or
                         not present
source                  1..14
                        mol_type = protein
                        organism = synthetic construct
SEQUENCE: 14
LKAALRAARF LWQR                                                    14

SEQ ID NO: 15           moltype = AA   length = 14
FEATURE                 Location/Qualifiers
MOD_RES                 3
                        note = S-pentenyl alanine
MOD_RES                 7
                        note = S-pentenyl alanine
VARIANT                 12
                        note = Non-natural electrophile containing amino acid or
                         not present
source                  1..14
                        mol_type = protein
                        organism = synthetic construct
SEQUENCE: 15
LKAALRAHRF LAQR                                                    14

SEQ ID NO: 16           moltype = AA   length = 14
FEATURE                 Location/Qualifiers
VARIANT                 4
                        note = Non-natural electrophile containing amino acid or
                         not present
MOD_RES                 9
                        note = S-pentenyl alanine
MOD_RES                 13
                        note = S-pentenyl alanine
source                  1..14
                        mol_type = protein
                        organism = synthetic construct
SEQUENCE: 16
LKKALRRHAF LWAR                                                    14

SEQ ID NO: 17           moltype = AA   length = 14
FEATURE                 Location/Qualifiers
VARIANT                 8
                        note = Non-natural electrophile containing amino acid or
                         not present
MOD_RES                 9
                        note = S-pentenyl alanine
MOD_RES                 13
                        note = S-pentenyl alanine
source                  1..14
                        mol_type = protein
                        organism = synthetic construct
SEQUENCE: 17
LKKALRRAAF LWAR                                                    14
```

-continued

```
SEQ ID NO: 18           moltype = AA  length = 14
FEATURE                 Location/Qualifiers
MOD_RES                 9
                        note = S-pentenyl alanine
VARIANT                 12
                        note = Non-natural electrophile containing amino acid or
                         not present
MOD_RES                 13
                        note = S-pentenyl alanine
source                  1..14
                        mol_type = protein
                        organism = synthetic construct
SEQUENCE: 18
LKKALRRHAF LAAR                                                          14

SEQ ID NO: 19           moltype = AA  length = 14
FEATURE                 Location/Qualifiers
MOD_RES                 2
                        note = R-octenyl alanine
VARIANT                 4
                        note = Non-natural electrophile containing amino acid or
                         not present
MOD_RES                 9
                        note = S-pentenyl alanine
source                  1..14
                        mol_type = protein
                        organism = synthetic construct
SEQUENCE: 19
LAKALRRHAF LWQR                                                          14

SEQ ID NO: 20           moltype = AA  length = 14
FEATURE                 Location/Qualifiers
MOD_RES                 2
                        note = R-octenyl alanine
VARIANT                 8
                        note = Non-natural electrophile containing amino acid or
                         not present
MOD_RES                 9
                        note = S-pentenyl alanine
source                  1..14
                        mol_type = protein
                        organism = synthetic construct
SEQUENCE: 20
LAKALRRAAF LWQR                                                          14

SEQ ID NO: 21           moltype = AA  length = 14
FEATURE                 Location/Qualifiers
MOD_RES                 2
                        note = R-octenyl alanine
MOD_RES                 9
                        note = S-pentenyl alanine
VARIANT                 12
                        note = Non-natural electrophile containing amino acid or
                         not present
source                  1..14
                        mol_type = protein
                        organism = synthetic construct
SEQUENCE: 21
LAKALRRHAF LAQR                                                          14

SEQ ID NO: 22           moltype = AA  length = 13
FEATURE                 Location/Qualifiers
MOD_RES                 13
                        note = S-pentenyl alanine
source                  1..13
                        mol_type = protein
                        organism = synthetic construct
SEQUENCE: 22
KKRYSRLQLL LLA                                                           13

SEQ ID NO: 23           moltype = AA  length = 13
FEATURE                 Location/Qualifiers
VARIANT                 6
                        note = Non-natural electrophile containing amino acid or
                         not present
MOD_RES                 13
                        note = S-pentenyl alanine
source                  1..13
                        mol_type = protein
```

```
                        organism = synthetic construct
SEQUENCE: 23
KKRYSALQLL LLA                                                      13

SEQ ID NO: 24          moltype = AA  length = 18
FEATURE                Location/Qualifiers
MOD_RES                2
                       note = R-octenyl alanine
MOD_RES                9
                       note = S-pentenyl alanine
VARIANT                13
                       note = Non-natural electrophile containing amino acid or
                        not present
source                 1..18
                       mol_type = protein
                       organism = synthetic construct
SEQUENCE: 24
QATEKMEEAL DLASAILD                                                 18

SEQ ID NO: 25          moltype = AA  length = 18
FEATURE                Location/Qualifiers
MOD_RES                2
                       note = R-octenyl alanine
MOD_RES                9
                       note = S-pentenyl alanine
VARIANT                17
                       note = Non-natural electrophile containing amino acid or
                        not present
source                 1..18
                       mol_type = protein
                       organism = synthetic construct
SEQUENCE: 25
QATEKMEEAL DLLSAIAD                                                 18

SEQ ID NO: 26          moltype = AA  length = 18
FEATURE                Location/Qualifiers
MOD_RES                1
                       note = S-pentenyl alanine
MOD_RES                5
                       note = S-pentenyl alanine
VARIANT                13
                       note = Non-natural electrophile containing amino acid or
                        not present
source                 1..18
                       mol_type = protein
                       organism = synthetic construct
SEQUENCE: 26
ADTEAMEEQL DLASAILD                                                 18

SEQ ID NO: 27          moltype = AA  length = 18
FEATURE                Location/Qualifiers
MOD_RES                1
                       note = S-pentenyl alanine
MOD_RES                5
                       note = S-pentenyl alanine
VARIANT                17
                       note = Non-natural electrophile containing amino acid or
                        not present
source                 1..18
                       mol_type = protein
                       organism = synthetic construct
SEQUENCE: 27
ADTEAMEEQL DLLSAIAD                                                 18

SEQ ID NO: 28          moltype = AA  length = 18
FEATURE                Location/Qualifiers
MOD_RES                5
                       note = R-octenyl alanine
MOD_RES                12
                       note = S-pentenyl alanine
VARIANT                13
                       note = Non-natural electrophile containing amino acid or
                        not present
source                 1..18
                       mol_type = protein
                       organism = synthetic construct
SEQUENCE: 28
QDTEAMEEQL DAASAILD                                                 18
```

-continued

```
SEQ ID NO: 29           moltype = AA   length = 18
FEATURE                 Location/Qualifiers
MOD_RES                 5
                        note = R-octenyl alanine
MOD_RES                 12
                        note = S-pentenyl alanine
VARIANT                 17
                        note = Non-natural electrophile containing amino acid or
                         not present
source                  1..18
                        mol_type = protein
                        organism = synthetic construct
SEQUENCE: 29
QDTEAMEEQL DALSAIAD                                                        18

SEQ ID NO: 30           moltype = AA   length = 18
FEATURE                 Location/Qualifiers
MOD_RES                 5
                        note = S-pentenyl alanine
MOD_RES                 9
                        note = S-pentenyl alanine
VARIANT                 13
                        note = Non-natural electrophile containing amino acid or
                         not present
source                  1..18
                        mol_type = protein
                        organism = synthetic construct
SEQUENCE: 30
QDTEAMEEAL DLASAILD                                                        18

SEQ ID NO: 31           moltype = AA   length = 18
FEATURE                 Location/Qualifiers
MOD_RES                 5
                        note = S-pentenyl alanine
MOD_RES                 9
                        note = S-pentenyl alanine
VARIANT                 17
                        note = Non-natural electrophile containing amino acid or
                         not present
source                  1..18
                        mol_type = protein
                        organism = synthetic construct
SEQUENCE: 31
QDTEAMEEAL DLLSAIAD                                                        18

SEQ ID NO: 32           moltype = AA   length = 18
FEATURE                 Location/Qualifiers
MOD_RES                 7
                        note = R-octenyl alanine
VARIANT                 13
                        note = Non-natural electrophile containing amino acid or
                         not present
MOD_RES                 14
                        note = S-pentenyl alanine
source                  1..18
                        mol_type = protein
                        organism = synthetic construct
SEQUENCE: 32
QDTEKMAEQL DLAAAILD                                                        18

SEQ ID NO: 33           moltype = AA   length = 18
FEATURE                 Location/Qualifiers
MOD_RES                 7
                        note = R-octenyl alanine
MOD_RES                 14
                        note = S-pentenyl alanine
VARIANT                 17
                        note = Non-natural electrophile containing amino acid or
                         not present
source                  1..18
                        mol_type = protein
                        organism = synthetic construct
SEQUENCE: 33
QDTEKMAEQL DLLAAIAD                                                        18

SEQ ID NO: 34           moltype = AA   length = 31
FEATURE                 Location/Qualifiers
source                  1..31
                        mol_type = protein
```

-continued

```
                        organism = synthetic construct
SEQUENCE: 34
NLSDVDLSKY ITTIAGVMTL SQVKGFVRKN G                           31

SEQ ID NO: 35           moltype = AA   length = 27
FEATURE                 Location/Qualifiers
VARIANT                 2
                        note = Non-natural electrophile containing amino acid or
                         not present
MOD_RES                 4
                        note = S-pentenyl alanine
MOD_RES                 8
                        note = S-pentenyl alanine
source                  1..27
                        mol_type = protein
                        organism = synthetic construct
SEQUENCE: 35
NASAVDLAKY ITTIAGVMTL SQVKGFV                                27

SEQ ID NO: 36           moltype = AA   length = 27
FEATURE                 Location/Qualifiers
MOD_RES                 4
                        note = S-pentenyl alanine
VARIANT                 6
                        note = Non-natural electrophile containing amino acid or
                         not present
MOD_RES                 8
                        note = S-pentenyl alanine
source                  1..27
                        mol_type = protein
                        organism = synthetic construct
SEQUENCE: 36
NLSAVALAKY ITTIAGVMTL SQVKGFV                                27

SEQ ID NO: 37           moltype = AA   length = 27
FEATURE                 Location/Qualifiers
MOD_RES                 4
                        note = S-pentenyl alanine
MOD_RES                 8
                        note = S-pentenyl alanine
VARIANT                 9
                        note = Non-natural electrophile containing amino acid or
                         not present
source                  1..27
                        mol_type = protein
                        organism = synthetic construct
SEQUENCE: 37
NLSAVDLAAY ITTIAGVMTL SQVKGFV                                27

SEQ ID NO: 38           moltype = AA   length = 27
FEATURE                 Location/Qualifiers
VARIANT                 2
                        note = Non-natural electrophile containing amino acid or
                         not present
MOD_RES                 8
                        note = S-pentenyl alanine
MOD_RES                 12
                        note = S-pentenyl alanine
source                  1..27
                        mol_type = protein
                        organism = synthetic construct
SEQUENCE: 38
NASDVDLAKY IATIAGVMTL SQVKGFV                                27

SEQ ID NO: 39           moltype = AA   length = 27
FEATURE                 Location/Qualifiers
VARIANT                 6
                        note = Non-natural electrophile containing amino acid or
                         not present
MOD_RES                 8
                        note = S-pentenyl alanine
MOD_RES                 12
                        note = S-pentenyl alanine
source                  1..27
                        mol_type = protein
                        organism = synthetic construct
SEQUENCE: 39
NLSDVALAKY IATIAGVMTL SQVKGFV                                27
```

-continued

```
SEQ ID NO: 40          moltype = AA  length = 27
FEATURE                Location/Qualifiers
MOD_RES                8
                       note = S-pentenyl alanine
VARIANT                9
                       note = Non-natural electrophile containing amino acid or
                        not present
MOD_RES                12
                       note = S-pentenyl alanine
source                 1..27
                       mol_type = protein
                       organism = synthetic construct
SEQUENCE: 40
NLSDVDLAAY IATIAGVMTL SQVKGFV                                          27

SEQ ID NO: 41          moltype = AA  length = 27
FEATURE                Location/Qualifiers
MOD_RES                1
                       note = R-octenyl alanine
VARIANT                2
                       note = Non-natural electrophile containing amino acid or
                        not present
MOD_RES                8
                       note = S-pentenyl alanine
source                 1..27
                       mol_type = protein
                       organism = synthetic construct
SEQUENCE: 41
AASDVDLAKY ITTIAGVMTL SQVKGFV                                          27

SEQ ID NO: 42          moltype = AA  length = 27
FEATURE                Location/Qualifiers
MOD_RES                1
                       note = R-octenyl alanine
VARIANT                6
                       note = Non-natural electrophile containing amino acid or
                        not present
MOD_RES                8
                       note = S-pentenyl alanine
source                 1..27
                       mol_type = protein
                       organism = synthetic construct
SEQUENCE: 42
ALSDVALAKY ITTIAGVMTL SQVKGFV                                          27

SEQ ID NO: 43          moltype = AA  length = 27
FEATURE                Location/Qualifiers
MOD_RES                1
                       note = R-octenyl alanine
MOD_RES                8
                       note = S-pentenyl alanine
VARIANT                9
                       note = Non-natural electrophile containing amino acid or
                        not present
source                 1..27
                       mol_type = protein
                       organism = synthetic construct
SEQUENCE: 43
ALSDVDLAAY ITTIAGVMTL SQVKGFV                                          27

SEQ ID NO: 44          moltype = AA  length = 27
FEATURE                Location/Qualifiers
VARIANT                2
                       note = Non-natural electrophile containing amino acid or
                        not present
MOD_RES                6
                       note = R-octenyl alanine
MOD_RES                13
                       note = S-pentenyl alanine
source                 1..27
                       mol_type = protein
                       organism = synthetic construct
SEQUENCE: 44
NASDVALSKY ITAIAGVMTL SQVKGFV                                          27

SEQ ID NO: 45          moltype = AA  length = 27
FEATURE                Location/Qualifiers
MOD_RES                6
                       note = R-octenyl alanine
```

-continued

```
VARIANT                  9
                         note = Non-natural electrophile containing amino acid or
                          not present
MOD_RES                  13
                         note = S-pentenyl alanine
source                   1..27
                         mol_type = protein
                         organism = synthetic construct
SEQUENCE: 45
NLSDVALSAY ITAIAGVMTL SQVKGFV                                            27

SEQ ID NO: 46            moltype = AA  length = 23
FEATURE                  Location/Qualifiers
source                   1..23
                         mol_type = protein
                         organism = synthetic construct
SEQUENCE: 46
LSEQMASLEG LMKQLNAITG SAF                                                23

SEQ ID NO: 47            moltype = AA  length = 17
FEATURE                  Location/Qualifiers
MOD_RES                  4
                         note = R-octenyl alanine
MOD_RES                  11
                         note = S-pentenyl alanine
VARIANT                  17
                         note = Non-natural electrophile containing amino acid or
                          not present
source                   1..17
                         mol_type = protein
                         organism = synthetic construct
SEQUENCE: 47
QMAALEGLMK ALNAITA                                                       17

SEQ ID NO: 48            moltype = AA  length = 17
FEATURE                  Location/Qualifiers
MOD_RES                  6
                         note = S-pentenyl alanine
MOD_RES                  10
                         note = S-pentenyl alanine
VARIANT                  17
                         note = Non-natural electrophile containing amino acid or
                          not present
source                   1..17
                         mol_type = protein
                         organism = synthetic construct
SEQUENCE: 48
QMASLAGLMA QLNAITA                                                       17

SEQ ID NO: 49            moltype = AA  length = 17
FEATURE                  Location/Qualifiers
MOD_RES                  7
                         note = S-pentenyl alanine
MOD_RES                  11
                         note = S-pentenyl alanine
VARIANT                  17
                         note = Non-natural electrophile containing amino acid or
                          not present
source                   1..17
                         mol_type = protein
                         organism = synthetic construct
SEQUENCE: 49
QMASLEALMK ALNAITA                                                       17

SEQ ID NO: 50            moltype = AA  length = 29
FEATURE                  Location/Qualifiers
source                   1..29
                         mol_type = protein
                         organism = synthetic construct
SEQUENCE: 50
IFINTRRKVD WLTEKMHARD FTVSAMHGD                                          29

SEQ ID NO: 51            moltype = AA  length = 15
FEATURE                  Location/Qualifiers
VARIANT                  1
                         note = Non-natural electrophile containing amino acid or
                          not present
MOD_RES                  6
                         note = R-octenyl alanine
```

```
MOD_RES                13
                       note = S-pentenyl alanine
source                 1..15
                       mol_type = protein
                       organism = synthetic construct
SEQUENCE: 51
ARRKVAWLTE KMAAR                                                        15

SEQ ID NO: 52          moltype = AA   length = 15
FEATURE                Location/Qualifiers
VARIANT                1
                       note = Non-natural electrophile containing amino acid or
                        not present
source                 1..15
                       mol_type = protein
                       organism = synthetic construct
SEQUENCE: 52
ARRKVDWLTE KMHAR                                                        15

SEQ ID NO: 53          moltype = AA   length = 15
FEATURE                Location/Qualifiers
VARIANT                1
                       note = Non-natural electrophile containing amino acid or
                        not present
MOD_RES                2
                       note = R-octenyl alanine
MOD_RES                9
                       note = S-pentenyl alanine
source                 1..15
                       mol_type = protein
                       organism = synthetic construct
SEQUENCE: 53
AARKVDWLAE KMHAR                                                        15

SEQ ID NO: 54          moltype = AA   length = 16
FEATURE                Location/Qualifiers
VARIANT                1
                       note = Non-natural electrophile containing amino acid or
                        not present
MOD_RES                9
                       note = R-octenyl alanine
MOD_RES                16
                       note = S-pentenyl alanine
source                 1..16
                       mol_type = protein
                       organism = synthetic construct
SEQUENCE: 54
ARRKVDWLAE KMHARA                                                       16

SEQ ID NO: 55          moltype = AA   length = 15
FEATURE                Location/Qualifiers
VARIANT                1
                       note = Non-natural electrophile containing amino acid or
                        not present
MOD_RES                11
                       note = S-pentenyl alanine
MOD_RES                15
                       note = S-pentenyl alanine
source                 1..15
                       mol_type = protein
                       organism = synthetic construct
SEQUENCE: 55
ARRKVDWLTE AMHAA                                                        15

SEQ ID NO: 56          moltype = AA   length = 15
FEATURE                Location/Qualifiers
VARIANT                1
                       note = Non-natural electrophile containing amino acid or
                        not present
MOD_RES                4
                       note = R-octenyl alanine
MOD_RES                11
                       note = S-pentenyl alanine
source                 1..15
                       mol_type = protein
                       organism = synthetic construct
SEQUENCE: 56
ARRAVDWLTE AMHAR                                                        15
```

-continued

```
SEQ ID NO: 57            moltype = AA   length = 18
FEATURE                  Location/Qualifiers
source                   1..18
                         mol_type = protein
                         organism = synthetic construct
SEQUENCE: 57
GSQEDSDSEL EQYFTARW                                                  18

SEQ ID NO: 58            moltype = AA   length = 13
FEATURE                  Location/Qualifiers
VARIANT                  1
                         note = Non-natural electrophile containing amino acid or
                          not present
source                   1..13
                         mol_type = protein
                         organism = synthetic construct
SEQUENCE: 58
ADSELEQYFT ARW                                                       13

SEQ ID NO: 59            moltype = AA   length = 13
FEATURE                  Location/Qualifiers
VARIANT                  1
                         note = Non-natural electrophile containing amino acid or
                          not present
MOD_RES                  3
                         note = S-pentenyl alanine
MOD_RES                  7
                         note = S-pentenyl alanine
source                   1..13
                         mol_type = protein
                         organism = synthetic construct
SEQUENCE: 59
ADAELEAYFT ARW                                                       13

SEQ ID NO: 60            moltype = AA   length = 13
FEATURE                  Location/Qualifiers
VARIANT                  1
                         note = Non-natural electrophile containing amino acid or
                          not present
MOD_RES                  3
                         note = R-octenyl alanine
MOD_RES                  10
                         note = S-pentenyl alanine
source                   1..13
                         mol_type = protein
                         organism = synthetic construct
SEQUENCE: 60
ADAELEQYFA ARW                                                       13

SEQ ID NO: 61            moltype = AA   length = 13
FEATURE                  Location/Qualifiers
VARIANT                  1
                         note = Non-natural electrophile containing amino acid or
                          not present
source                   1..13
                         mol_type = protein
                         organism = synthetic construct
SEQUENCE: 61
ADSELEQYFT ARW                                                       13

SEQ ID NO: 62            moltype = AA   length = 39
FEATURE                  Location/Qualifiers
source                   1..39
                         mol_type = protein
                         organism = synthetic construct
SEQUENCE: 62
MEEPQSDPSV EPPLSQETFS DLWKLLPENN VLSPLPSQA                           39

SEQ ID NO: 63            moltype = AA   length = 14
FEATURE                  Location/Qualifiers
VARIANT                  14
                         note = Non-natural electrophile containing amino acid or
                          not present
source                   1..14
                         mol_type = protein
                         organism = synthetic construct
SEQUENCE: 63
LSQETFSDLW KLLA                                                      14
```

-continued

```
SEQ ID NO: 64          moltype = AA   length = 14
FEATURE                Location/Qualifiers
MOD_RES                3
                       note = S-pentenyl alanine
MOD_RES                7
                       note = S-pentenyl alanine
VARIANT                14
                       note = Non-natural electrophile containing amino acid or
                        not present
source                 1..14
                       mol_type = protein
                       organism = synthetic construct
SEQUENCE: 64
LSAETFADLW KLLA                                                     14

SEQ ID NO: 65          moltype = AA   length = 14
FEATURE                Location/Qualifiers
MOD_RES                3
                       note = R-octenyl alanine
MOD_RES                10
                       note = S-pentenyl alanine
VARIANT                14
                       note = Non-natural electrophile containing amino acid or
                        not present
source                 1..14
                       mol_type = protein
                       organism = synthetic construct
SEQUENCE: 65
LSAETFSDLA KLLA                                                     14

SEQ ID NO: 66          moltype = AA   length = 14
FEATURE                Location/Qualifiers
MOD_RES                7
                       note = S-pentenyl alanine
MOD_RES                11
                       note = S-pentenyl alanine
VARIANT                14
                       note = Non-natural electrophile containing amino acid or
                        not present
source                 1..14
                       mol_type = protein
                       organism = synthetic construct
SEQUENCE: 66
LSQETFADLW ALLA                                                     14

SEQ ID NO: 67          moltype = AA   length = 14
FEATURE                Location/Qualifiers
MOD_RES                8
                       note = S-pentenyl alanine
MOD_RES                12
                       note = S-pentenyl alanine
VARIANT                14
                       note = Non-natural electrophile containing amino acid or
                        not present
source                 1..14
                       mol_type = protein
                       organism = synthetic construct
SEQUENCE: 67
LSQETFSALW KALA                                                     14

SEQ ID NO: 68          moltype = AA   length = 26
FEATURE                Location/Qualifiers
source                 1..26
                       mol_type = protein
                       organism = synthetic construct
SEQUENCE: 68
GMSSGFYKNV VKIQKHVTFN QVKGIF                                        26

SEQ ID NO: 69          moltype = AA   length = 15
FEATURE                Location/Qualifiers
VARIANT                10
                       note = Non-natural electrophile containing amino acid or
                        not present
source                 1..15
                       mol_type = protein
                       organism = synthetic construct
SEQUENCE: 69
FYKNVVKIQA HVTFN                                                    15
```

-continued

```
SEQ ID NO: 70          moltype = AA  length = 15
FEATURE                Location/Qualifiers
MOD_RES                8
                       note = R-octenyl alanine
VARIANT                9
                       note = Non-natural electrophile containing amino acid or
                        not present
MOD_RES                14
                       note = S-pentenyl alanine
source                 1..15
                       mol_type = protein
                       organism = synthetic construct
SEQUENCE: 70
FYKNVVKAQA HVTFA                                                        15

SEQ ID NO: 71          moltype = AA  length = 15
FEATURE                Location/Qualifiers
MOD_RES                4
                       note = R-octenyl alanine
VARIANT                9
                       note = Non-natural electrophile containing amino acid or
                        not present
MOD_RES                10
                       note = S-pentenyl alanine
source                 1..15
                       mol_type = protein
                       organism = synthetic construct
SEQUENCE: 71
FYKAVVKIQA AVTFN                                                        15

SEQ ID NO: 72          moltype = AA  length = 15
FEATURE                Location/Qualifiers
MOD_RES                2
                       note = R-octenyl alanine
MOD_RES                8
                       note = S-pentenyl alanine
VARIANT                9
                       note = Non-natural electrophile containing amino acid or
                        not present
source                 1..15
                       mol_type = protein
                       organism = synthetic construct
SEQUENCE: 72
FAKNVVKIAA HVTFN                                                        15

SEQ ID NO: 73          moltype = AA  length = 15
FEATURE                Location/Qualifiers
MOD_RES                9
                       note = S-pentenyl alanine
VARIANT                10
                       note = Non-natural electrophile containing amino acid or
                        not present
MOD_RES                13
                       note = S-pentenyl alanine
source                 1..15
                       mol_type = protein
                       organism = synthetic construct
SEQUENCE: 73
FYKNVVKIAA HVAFN                                                        15

SEQ ID NO: 74          moltype = AA  length = 15
FEATURE                Location/Qualifiers
VARIANT                10
                       note = Non-natural electrophile containing amino acid or
                        not present
MOD_RES                11
                       note = S-pentenyl alanine
MOD_RES                15
                       note = S-pentenyl alanine
source                 1..15
                       mol_type = protein
                       organism = synthetic construct
SEQUENCE: 74
FYKNVVKIQA AVTFA                                                        15

SEQ ID NO: 75          moltype = AA  length = 15
FEATURE                Location/Qualifiers
MOD_RES                7
                       note = S-pentenyl alanine
```

-continued

```
VARIANT                 10
                        note = Non-natural electrophile containing amino acid or
                         not present
MOD_RES                 11
                        note = S-pentenyl alanine
source                  1..15
                        mol_type = protein
                        organism = synthetic construct
SEQUENCE: 75
FYKNVVAIQA AVTFN                                                        15

SEQ ID NO: 76           moltype = AA  length = 16
FEATURE                 Location/Qualifiers
MOD_RES                 1
                        note = S-pentenyl alanine
MOD_RES                 5
                        note = S-pentenyl alanine
VARIANT                 14
                        note = Non-natural electrophile containing amino acid or
                         not present
source                  1..16
                        mol_type = protein
                        organism = synthetic construct
SEQUENCE: 76
AFGIALTNIL KTEAGN                                                       16

SEQ ID NO: 77           moltype = AA  length = 16
FEATURE                 Location/Qualifiers
MOD_RES                 2
                        note = S-pentenyl alanine
MOD_RES                 6
                        note = S-pentenyl alanine
VARIANT                 14
                        note = Non-natural electrophile containing amino acid or
                         not present
source                  1..16
                        mol_type = protein
                        organism = synthetic construct
SEQUENCE: 77
FAGIYATNIL KTEAGN                                                       16

SEQ ID NO: 78           moltype = AA  length = 16
FEATURE                 Location/Qualifiers
MOD_RES                 3
                        note = S-pentenyl alanine
MOD_RES                 7
                        note = S-pentenyl alanine
VARIANT                 14
                        note = Non-natural electrophile containing amino acid or
                         not present
source                  1..16
                        mol_type = protein
                        organism = synthetic construct
SEQUENCE: 78
FFAIYLANIL KTEAGN                                                       16

SEQ ID NO: 79           moltype = AA  length = 16
FEATURE                 Location/Qualifiers
MOD_RES                 4
                        note = S-pentenyl alanine
MOD_RES                 8
                        note = S-pentenyl alanine
VARIANT                 14
                        note = Non-natural electrophile containing amino acid or
                         not present
source                  1..16
                        mol_type = protein
                        organism = synthetic construct
SEQUENCE: 79
FFGAYLTAIL KTEAGN                                                       16

SEQ ID NO: 80           moltype = AA  length = 16
FEATURE                 Location/Qualifiers
MOD_RES                 5
                        note = S-pentenyl alanine
MOD_RES                 9
                        note = S-pentenyl alanine
VARIANT                 14
                        note = Non-natural electrophile containing amino acid or
```

```
                                           -continued
```

```
                            not present
source                      1..16
                            mol_type = protein
                            organism = synthetic construct
SEQUENCE: 80
FFGIALTNAL KTEAGN                                                    16

SEQ ID NO: 81               moltype = AA  length = 16
FEATURE                     Location/Qualifiers
MOD_RES                     6
                            note = S-pentenyl alanine
MOD_RES                     10
                            note = S-pentenyl alanine
VARIANT                     14
                            note = Non-natural electrophile containing amino acid or
                             not present
source                      1..16
                            mol_type = protein
                            organism = synthetic construct
SEQUENCE: 81
FFGIYATNIA KTEAGN                                                    16

SEQ ID NO: 82               moltype = AA  length = 16
FEATURE                     Location/Qualifiers
MOD_RES                     7
                            note = S-pentenyl alanine
MOD_RES                     11
                            note = S-pentenyl alanine
VARIANT                     14
                            note = Non-natural electrophile containing amino acid or
                             not present
source                      1..16
                            mol_type = protein
                            organism = synthetic construct
SEQUENCE: 82
FFGIYLANIL ATEAGN                                                    16

SEQ ID NO: 83               moltype = AA  length = 16
FEATURE                     Location/Qualifiers
MOD_RES                     8
                            note = S-pentenyl alanine
MOD_RES                     12
                            note = S-pentenyl alanine
VARIANT                     14
                            note = Non-natural electrophile containing amino acid or
                             not present
source                      1..16
                            mol_type = protein
                            organism = synthetic construct
SEQUENCE: 83
FFGIYLTAIL KAEAGN                                                    16

SEQ ID NO: 84               moltype = AA  length = 16
FEATURE                     Location/Qualifiers
MOD_RES                     9
                            note = S-pentenyl alanine
MOD_RES                     13
                            note = S-pentenyl alanine
VARIANT                     14
                            note = Non-natural electrophile containing amino acid or
                             not present
source                      1..16
                            mol_type = protein
                            organism = synthetic construct
SEQUENCE: 84
FFGIYLTNAL KTAAGN                                                    16

SEQ ID NO: 85               moltype = AA  length = 16
FEATURE                     Location/Qualifiers
MOD_RES                     11
                            note = S-pentenyl alanine
VARIANT                     14
                            note = Non-natural electrophile containing amino acid or
                             not present
MOD_RES                     15
                            note = S-pentenyl alanine
source                      1..16
                            mol_type = protein
                            organism = synthetic construct
```

SEQUENCE: 85
FFGIYLTNIL ATEAAN                                                              16

SEQ ID NO: 86            moltype = AA   length = 16
FEATURE                  Location/Qualifiers
MOD_RES                  12
                         note = S-pentenyl alanine
VARIANT                  14
                         note = Non-natural electrophile containing amino acid or
                          not present
MOD_RES                  16
                         note = S-pentenyl alanine
source                   1..16
                         mol_type = protein
                         organism = synthetic construct
SEQUENCE: 86
FFGIYLTNIL KAEAGA                                                              16

SEQ ID NO: 87            moltype = AA   length = 17
FEATURE                  Location/Qualifiers
MOD_RES                  13
                         note = S-pentenyl alanine
VARIANT                  14
                         note = Non-natural electrophile containing amino acid or
                          not present
MOD_RES                  17
                         note = S-pentenyl alanine
source                   1..17
                         mol_type = protein
                         organism = synthetic construct
SEQUENCE: 87
FFGIYLTNIL KTAAGNA                                                             17

SEQ ID NO: 88            moltype = AA   length = 16
FEATURE                  Location/Qualifiers
MOD_RES                  1
                         note = R-octenyl alanine
MOD_RES                  8
                         note = S-pentenyl alanine
VARIANT                  14
                         note = Non-natural electrophile containing amino acid or
                          not present
source                   1..16
                         mol_type = protein
                         organism = synthetic construct
SEQUENCE: 88
AFGIYLTAIL KTEAGN                                                              16

SEQ ID NO: 89            moltype = AA   length = 16
FEATURE                  Location/Qualifiers
MOD_RES                  2
                         note = R-octenyl alanine
MOD_RES                  9
                         note = S-pentenyl alanine
VARIANT                  14
                         note = Non-natural electrophile containing amino acid or
                          not present
source                   1..16
                         mol_type = protein
                         organism = synthetic construct
SEQUENCE: 89
FAGIYLTNAL KTEAGN                                                              16

SEQ ID NO: 90            moltype = AA   length = 16
FEATURE                  Location/Qualifiers
MOD_RES                  3
                         note = R-octenyl alanine
MOD_RES                  10
                         note = S-pentenyl alanine
VARIANT                  14
                         note = Non-natural electrophile containing amino acid or
                          not present
source                   1..16
                         mol_type = protein
                         organism = synthetic construct
SEQUENCE: 90
FFAIYLTNIA KTEAGN                                                              16

SEQ ID NO: 91            moltype = AA   length = 16

-continued

```
FEATURE                 Location/Qualifiers
MOD_RES                 4
                        note = R-octenyl alanine
MOD_RES                 11
                        note = S-pentenyl alanine
VARIANT                 14
                        note = Non-natural electrophile containing amino acid or
                         not present
source                  1..16
                        mol_type = protein
                        organism = synthetic construct
SEQUENCE: 91
FFGAYLTNIL ATEAGN                                                            16

SEQ ID NO: 92           moltype = AA  length = 16
FEATURE                 Location/Qualifiers
MOD_RES                 5
                        note = R-octenyl alanine
MOD_RES                 12
                        note = S-pentenyl alanine
VARIANT                 14
                        note = Non-natural electrophile containing amino acid or
                         not present
source                  1..16
                        mol_type = protein
                        organism = synthetic construct
SEQUENCE: 92
FFGIALTNIL KAEAGN                                                            16

SEQ ID NO: 93           moltype = AA  length = 16
FEATURE                 Location/Qualifiers
MOD_RES                 6
                        note = R-octenyl alanine
MOD_RES                 13
                        note = S-pentenyl alanine
VARIANT                 14
                        note = Non-natural electrophile containing amino acid or
                         not present
source                  1..16
                        mol_type = protein
                        organism = synthetic construct
SEQUENCE: 93
FFGIYATNIL KTAAGN                                                            16

SEQ ID NO: 94           moltype = AA  length = 16
FEATURE                 Location/Qualifiers
MOD_RES                 8
                        note = R-octenyl alanine
VARIANT                 14
                        note = Non-natural electrophile containing amino acid or
                         not present
MOD_RES                 15
                        note = S-pentenyl alanine
source                  1..16
                        mol_type = protein
                        organism = synthetic construct
SEQUENCE: 94
FFGIYLTAIL KTEAAN                                                            16

SEQ ID NO: 95           moltype = AA  length = 16
FEATURE                 Location/Qualifiers
MOD_RES                 9
                        note = R-octenyl alanine
VARIANT                 14
                        note = Non-natural electrophile containing amino acid or
                         not present
MOD_RES                 16
                        note = S-pentenyl alanine
source                  1..16
                        mol_type = protein
                        organism = synthetic construct
SEQUENCE: 95
FFGIYLTNAL KTEAGA                                                            16

SEQ ID NO: 96           moltype = AA  length = 17
FEATURE                 Location/Qualifiers
MOD_RES                 10
                        note = R-octenyl alanine
VARIANT                 14
```

-continued

```
                         note = Non-natural electrophile containing amino acid or
                          not present
MOD_RES                  17
                         note = S-pentenyl alanine
source                   1..17
                         mol_type = protein
                         organism = synthetic construct
SEQUENCE: 96
FFGIYLTNIA KTEAGNA                                                       17

SEQ ID NO: 97            moltype = AA  length = 16
FEATURE                  Location/Qualifiers
VARIANT                  14
                         note = Non-natural electrophile containing amino acid or
                          not present
source                   1..16
                         mol_type = protein
                         organism = synthetic construct
SEQUENCE: 97
FFGIYLTNIL KTEAGN                                                        16

SEQ ID NO: 98            moltype = AA  length = 16
FEATURE                  Location/Qualifiers
MOD_RES                  1
                         note = S-pentenyl alanine
MOD_RES                  5
                         note = S-pentenyl alanine
VARIANT                  10
                         note = Non-natural electrophile containing amino acid or
                          not present
source                   1..16
                         mol_type = protein
                         organism = synthetic construct
SEQUENCE: 98
AFGIALTNIA KTEEGN                                                        16

SEQ ID NO: 99            moltype = AA  length = 16
FEATURE                  Location/Qualifiers
MOD_RES                  2
                         note = S-pentenyl alanine
MOD_RES                  6
                         note = S-pentenyl alanine
VARIANT                  10
                         note = Non-natural electrophile containing amino acid or
                          not present
source                   1..16
                         mol_type = protein
                         organism = synthetic construct
SEQUENCE: 99
FAGIYATNIA KTEEGN                                                        16

SEQ ID NO: 100           moltype = AA  length = 16
FEATURE                  Location/Qualifiers
MOD_RES                  3
                         note = S-pentenyl alanine
MOD_RES                  7
                         note = S-pentenyl alanine
VARIANT                  10
                         note = Non-natural electrophile containing amino acid or
                          not present
source                   1..16
                         mol_type = protein
                         organism = synthetic construct
SEQUENCE: 100
FFAIYLANIA KTEEGN                                                        16

SEQ ID NO: 101           moltype = AA  length = 16
FEATURE                  Location/Qualifiers
MOD_RES                  4
                         note = S-pentenyl alanine
MOD_RES                  8
                         note = S-pentenyl alanine
VARIANT                  10
                         note = Non-natural electrophile containing amino acid or
                          not present
source                   1..16
                         mol_type = protein
                         organism = synthetic construct
SEQUENCE: 101
```

-continued

```
FFGAYLTAIA KTEEGN                                                  16

SEQ ID NO: 102         moltype = AA   length = 16
FEATURE                Location/Qualifiers
MOD_RES                5
                       note = S-pentenyl alanine
MOD_RES                9
                       note = S-pentenyl alanine
VARIANT                10
                       note = Non-natural electrophile containing amino acid or
                        not present
source                 1..16
                       mol_type = protein
                       organism = synthetic construct
SEQUENCE: 102
FFGIALTNAA KTEEGN                                                  16

SEQ ID NO: 103         moltype = AA   length = 16
FEATURE                Location/Qualifiers
MOD_RES                7
                       note = S-pentenyl alanine
VARIANT                10
                       note = Non-natural electrophile containing amino acid or
                        not present
MOD_RES                11
                       note = S-pentenyl alanine
source                 1..16
                       mol_type = protein
                       organism = synthetic construct
SEQUENCE: 103
FFGIYLANIA ATEEGN                                                  16

SEQ ID NO: 104         moltype = AA   length = 16
FEATURE                Location/Qualifiers
MOD_RES                8
                       note = S-pentenyl alanine
VARIANT                10
                       note = Non-natural electrophile containing amino acid or
                        not present
MOD_RES                12
                       note = S-pentenyl alanine
source                 1..16
                       mol_type = protein
                       organism = synthetic construct
SEQUENCE: 104
FFGIYLTAIA KAEEGN                                                  16

SEQ ID NO: 105         moltype = AA   length = 16
FEATURE                Location/Qualifiers
MOD_RES                9
                       note = S-pentenyl alanine
VARIANT                10
                       note = Non-natural electrophile containing amino acid or
                        not present
MOD_RES                13
                       note = S-pentenyl alanine
source                 1..16
                       mol_type = protein
                       organism = synthetic construct
SEQUENCE: 105
FFGIYLTNAA KTAEGN                                                  16

SEQ ID NO: 106         moltype = AA   length = 16
FEATURE                Location/Qualifiers
VARIANT                10
                       note = Non-natural electrophile containing amino acid or
                        not present
MOD_RES                11
                       note = S-pentenyl alanine
MOD_RES                15
                       note = S-pentenyl alanine
source                 1..16
                       mol_type = protein
                       organism = synthetic construct
SEQUENCE: 106
FFGIYLTNIA ATEEAN                                                  16

SEQ ID NO: 107         moltype = AA   length = 16
FEATURE                Location/Qualifiers
```

-continued

```
VARIANT            10
                   note = Non-natural electrophile containing amino acid or
                    not present
MOD_RES            12
                   note = S-pentenyl alanine
MOD_RES            16
                   note = S-pentenyl alanine
source             1..16
                   mol_type = protein
                   organism = synthetic construct
SEQUENCE: 107
FFGIYLTNIA KAEEGA                                                  16

SEQ ID NO: 108     moltype = AA   length = 17
FEATURE            Location/Qualifiers
VARIANT            10
                   note = Non-natural electrophile containing amino acid or
                    not present
MOD_RES            13
                   note = S-pentenyl alanine
MOD_RES            17
                   note = S-pentenyl alanine
source             1..17
                   mol_type = protein
                   organism = synthetic construct
SEQUENCE: 108
FFGIYLTNIA KTAEGNA                                                 17

SEQ ID NO: 109     moltype = AA   length = 16
FEATURE            Location/Qualifiers
MOD_RES            1
                   note = R-octenyl alanine
MOD_RES            8
                   note = S-pentenyl alanine
VARIANT            10
                   note = Non-natural electrophile containing amino acid or
                    not present
source             1..16
                   mol_type = protein
                   organism = synthetic construct
SEQUENCE: 109
AFGIYLTAIA KTEEGN                                                  16

SEQ ID NO: 110     moltype = AA   length = 16
FEATURE            Location/Qualifiers
MOD_RES            2
                   note = R-octenyl alanine
MOD_RES            9
                   note = S-pentenyl alanine
VARIANT            10
                   note = Non-natural electrophile containing amino acid or
                    not present
source             1..16
                   mol_type = protein
                   organism = synthetic construct
SEQUENCE: 110
FAGIYLTNAA KTEEGN                                                  16

SEQ ID NO: 111     moltype = AA   length = 16
FEATURE            Location/Qualifiers
MOD_RES            4
                   note = R-octenyl alanine
VARIANT            10
                   note = Non-natural electrophile containing amino acid or
                    not present
MOD_RES            11
                   note = S-pentenyl alanine
source             1..16
                   mol_type = protein
                   organism = synthetic construct
SEQUENCE: 111
FFGAYLTNIA ATEEGN                                                  16

SEQ ID NO: 112     moltype = AA   length = 16
FEATURE            Location/Qualifiers
MOD_RES            5
                   note = R-octenyl alanine
VARIANT            10
                   note = Non-natural electrophile containing amino acid or
```

-continued

```
                            not present
MOD_RES                     12
                            note = S-pentenyl alanine
source                      1..16
                            mol_type = protein
                            organism = synthetic construct
SEQUENCE: 112
FFGIALTNIA KAEEGN                                                    16

SEQ ID NO: 113              moltype = AA   length = 16
FEATURE                     Location/Qualifiers
MOD_RES                     6
                            note = R-octenyl alanine
VARIANT                     10
                            note = Non-natural electrophile containing amino acid or
                             not present
MOD_RES                     13
                            note = S-pentenyl alanine
source                      1..16
                            mol_type = protein
                            organism = synthetic construct
SEQUENCE: 113
FFGIYATNIA KTAEGN                                                    16

SEQ ID NO: 114              moltype = AA   length = 16
FEATURE                     Location/Qualifiers
MOD_RES                     7
                            note = R-octenyl alanine
VARIANT                     10
                            note = Non-natural electrophile containing amino acid or
                             not present
MOD_RES                     14
                            note = S-pentenyl alanine
source                      1..16
                            mol_type = protein
                            organism = synthetic construct
SEQUENCE: 114
FFGIYLANIA KTEAGN                                                    16

SEQ ID NO: 115              moltype = AA   length = 16
FEATURE                     Location/Qualifiers
MOD_RES                     8
                            note = R-octenyl alanine
VARIANT                     10
                            note = Non-natural electrophile containing amino acid or
                             not present
MOD_RES                     15
                            note = S-pentenyl alanine
source                      1..16
                            mol_type = protein
                            organism = synthetic construct
SEQUENCE: 115
FFGIYLTAIA KTEEAN                                                    16

SEQ ID NO: 116              moltype = AA   length = 16
FEATURE                     Location/Qualifiers
MOD_RES                     9
                            note = R-octenyl alanine
VARIANT                     10
                            note = Non-natural electrophile containing amino acid or
                             not present
MOD_RES                     16
                            note = S-pentenyl alanine
source                      1..16
                            mol_type = protein
                            organism = synthetic construct
SEQUENCE: 116
FFGIYLTNAA KTEEGA                                                    16

SEQ ID NO: 117              moltype = AA   length = 16
FEATURE                     Location/Qualifiers
VARIANT                     10
                            note = Non-natural electrophile containing amino acid or
                             not present
source                      1..16
                            mol_type = protein
                            organism = synthetic construct
SEQUENCE: 117
FFGIYLTNIA KTEEGN                                                    16
```

```
SEQ ID NO: 118           moltype =   length =
SEQUENCE: 118
000

SEQ ID NO: 119           moltype =   length =
SEQUENCE: 119
000

SEQ ID NO: 120           moltype =   length =
SEQUENCE: 120
000

SEQ ID NO: 121           moltype =   length =
SEQUENCE: 121
000

SEQ ID NO: 122           moltype =   length =
SEQUENCE: 122
000

SEQ ID NO: 123           moltype =   length =
SEQUENCE: 123
000

SEQ ID NO: 124           moltype = AA  length = 25
FEATURE                  Location/Qualifiers
VARIANT                  13
                         note = Any non-natural amino acid
VARIANT                  17
                         note = Any non-natural amino acid
source                   1..25
                         mol_type = protein
                         organism = synthetic construct
SEQUENCE: 124
AELEVECATQ LRXFGDXLNF RQKLL                                            25

SEQ ID NO: 125           moltype = AA  length = 25
FEATURE                  Location/Qualifiers
VARIANT                  13
                         note = Any non-natural amino acid
VARIANT                  17
                         note = Any non-natural amino acid
source                   1..25
                         mol_type = protein
                         organism = synthetic construct
SEQUENCE: 125
AELEVECATQ LRXFGDXLNF RQKDL                                            25

SEQ ID NO: 126           moltype = AA  length = 25
FEATURE                  Location/Qualifiers
VARIANT                  13
                         note = Any non-natural amino acid
VARIANT                  17
                         note = Any non-natural amino acid
source                   1..25
                         mol_type = protein
                         organism = synthetic construct
SEQUENCE: 126
AELEVELATQ LRXFGDXLNF RQKLL                                            25

SEQ ID NO: 127           moltype = AA  length = 25
FEATURE                  Location/Qualifiers
VARIANT                  13
                         note = Any non-natural amino acid
VARIANT                  17
                         note = Any non-natural amino acid
source                   1..25
                         mol_type = protein
                         organism = synthetic construct
SEQUENCE: 127
AELEVECLTQ LRXFGDXLNF RQKLL                                            25

SEQ ID NO: 128           moltype = AA  length = 25
FEATURE                  Location/Qualifiers
VARIANT                  13
                         note = Any non-natural amino acid
VARIANT                  17
                         note = Any non-natural amino acid
```

-continued

```
source                  1..25
                        mol_type = protein
                        organism = synthetic construct
SEQUENCE: 128
AELEVESATQ LRXFGDXLNF RQKLL                                          25

SEQ ID NO: 129          moltype = AA   length = 23
FEATURE                 Location/Qualifiers
VARIANT                 11
                        note = Any non-natural amino acid
VARIANT                 15
                        note = Any non-natural amino acid
source                  1..23
                        mol_type = protein
                        organism = synthetic construct
SEQUENCE: 129
LEVECATQLR XFGDXLNFRQ KLL                                            23

SEQ ID NO: 130          moltype = AA   length = 22
FEATURE                 Location/Qualifiers
VARIANT                 13
                        note = Any non-natural amino acid
VARIANT                 17
                        note = Any non-natural amino acid
source                  1..22
                        mol_type = protein
                        organism = synthetic construct
SEQUENCE: 130
AELEVECATQ LRXFGDXLNF RQ                                             22

SEQ ID NO: 131          moltype = AA   length = 25
FEATURE                 Location/Qualifiers
VARIANT                 13
                        note = Any non-natural amino acid
VARIANT                 17
                        note = Any non-natural amino acid
source                  1..25
                        mol_type = protein
                        organism = synthetic construct
SEQUENCE: 131
AELEVECATQ LRXYGDXLNF RQKLL                                          25

SEQ ID NO: 132          moltype = AA   length = 25
FEATURE                 Location/Qualifiers
VARIANT                 13
                        note = Any non-natural amino acid
VARIANT                 17
                        note = Any non-natural amino acid
source                  1..25
                        mol_type = protein
                        organism = synthetic construct
SEQUENCE: 132
AELEVECATQ LRXIGDXLNF RQKLL                                          25

SEQ ID NO: 133          moltype = AA   length = 20
FEATURE                 Location/Qualifiers
VARIANT                 9
                        note = Any non-natural amino acid
VARIANT                 13
                        note = Any non-natural amino acid
source                  1..20
                        mol_type = protein
                        organism = synthetic construct
SEQUENCE: 133
VECATQLRXF GDXLNFRQKL                                                20

SEQ ID NO: 134          moltype = AA   length = 20
FEATURE                 Location/Qualifiers
VARIANT                 9
                        note = Any non-natural amino acid
VARIANT                 13
                        note = Any non-natural amino acid
source                  1..20
                        mol_type = protein
                        organism = synthetic construct
SEQUENCE: 134
VECATQLRXF GFXLNFRQKL                                                20

SEQ ID NO: 135          moltype = AA   length = 25
```

-continued

```
FEATURE             Location/Qualifiers
VARIANT             6
                    note = Any non-natural amino acid
VARIANT             10
                    note = Any non-natural amino acid
source              1..25
                    mol_type = protein
                    organism = synthetic construct
SEQUENCE: 135
AELEVXCATX LRRFGDKLNF RQKLL                                       25

SEQ ID NO: 136      moltype = AA  length = 25
FEATURE             Location/Qualifiers
VARIANT             19
                    note = Any non-natural amino acid
VARIANT             23
                    note = Any non-natural amino acid
source              1..25
                    mol_type = protein
                    organism = synthetic construct
SEQUENCE: 136
AELEVECATQ LRRFGDKLXF RQXLL                                       25

SEQ ID NO: 137      moltype = AA  length = 24
FEATURE             Location/Qualifiers
VARIANT             1
                    note = Non-natural electrophile containing amino acid or
                     not present
VARIANT             11
                    note = Any non-natural amino acid
VARIANT             15
                    note = Any non-natural amino acid
source              1..24
                    mol_type = protein
                    organism = synthetic construct
SEQUENCE: 137
XEVESATQLR XFGDXLNFRQ KLLK                                        24

SEQ ID NO: 138      moltype = AA  length = 20
FEATURE             Location/Qualifiers
VARIANT             1
                    note = Non-natural electrophile containing amino acid or
                     not present
VARIANT             7
                    note = Any non-natural amino acid
VARIANT             11
                    note = Any non-natural amino acid
source              1..20
                    mol_type = protein
                    organism = synthetic construct
SEQUENCE: 138
XATQLRXFGD XLNFRQKLLK                                             20

SEQ ID NO: 139      moltype = AA  length = 23
FEATURE             Location/Qualifiers
VARIANT             1
                    note = Non-natural electrophile containing amino acid or
                     not present
VARIANT             11
                    note = Any non-natural amino acid
VARIANT             15
                    note = Any non-natural amino acid
source              1..23
                    mol_type = protein
                    organism = synthetic construct
SEQUENCE: 139
XEVESATQLR XFGDXLNFRQ KLL                                         23

SEQ ID NO: 140      moltype = AA  length = 19
FEATURE             Location/Qualifiers
VARIANT             1
                    note = Non-natural electrophile containing amino acid or
                     not present
VARIANT             7
                    note = Any non-natural amino acid
VARIANT             11
                    note = Any non-natural amino acid
source              1..19
                    mol_type = protein
```

-continued

```
                               organism = synthetic construct
SEQUENCE: 140
XATQLRXFGD XLNFRQKLL                                         19

SEQ ID NO: 141          moltype = AA   length = 17
FEATURE                 Location/Qualifiers
VARIANT                 1
                        note = Non-natural electrophile containing amino acid or
                         not present
VARIANT                 8
                        note = Any non-natural amino acid
VARIANT                 12
                        note = Any non-natural amino acid
source                  1..17
                        mol_type = protein
                        organism = synthetic construct
SEQUENCE: 141
XLSESLKXIG DXLDSNK                                           17

SEQ ID NO: 142          moltype = AA   length = 19
FEATURE                 Location/Qualifiers
VARIANT                 1
                        note = Non-natural electrophile containing amino acid or
                         not present
VARIANT                 7
                        note = Any non-natural amino acid
VARIANT                 11
                        note = Any non-natural amino acid
source                  1..19
                        mol_type = protein
                        organism = synthetic construct
SEQUENCE: 142
XAQELRXIGD XFNAYYARK                                         19

SEQ ID NO: 143          moltype = AA   length = 20
FEATURE                 Location/Qualifiers
VARIANT                 1
                        note = Non-natural electrophile containing amino acid or
                         not present
VARIANT                 8
                        note = Any non-natural amino acid
VARIANT                 12
                        note = Any non-natural amino acid
source                  1..20
                        mol_type = protein
                        organism = synthetic construct
SEQUENCE: 143
XIAQELRXIG DXFNAYYARK                                        20

SEQ ID NO: 144          moltype = AA   length = 19
FEATURE                 Location/Qualifiers
VARIANT                 1
                        note = Non-natural electrophile containing amino acid or
                         not present
VARIANT                 7
                        note = Any non-natural amino acid
VARIANT                 11
                        note = Any non-natural amino acid
source                  1..19
                        mol_type = protein
                        organism = synthetic construct
SEQUENCE: 144
XAQELRXIGD XFNAYYARR                                         19

SEQ ID NO: 145          moltype = AA   length = 20
FEATURE                 Location/Qualifiers
VARIANT                 1
                        note = Non-natural electrophile containing amino acid or
                         not present
VARIANT                 8
                        note = Any non-natural amino acid
VARIANT                 12
                        note = Any non-natural amino acid
source                  1..20
                        mol_type = protein
                        organism = synthetic construct
SEQUENCE: 145
XIAQELRXIG DXFNAYYARR                                        20
```

-continued

```
SEQ ID NO: 146          moltype = AA  length = 16
FEATURE                 Location/Qualifiers
VARIANT                 1
                        note = Non-natural electrophile containing amino acid or
                         not present
VARIANT                 4
                        note = Any non-natural amino acid
VARIANT                 8
                        note = Any non-natural amino acid
source                  1..16
                        mol_type = protein
                        organism = synthetic construct
SEQUENCE: 146
XVGXQLAXIG DDINRR                                                                16

SEQ ID NO: 147          moltype = AA  length = 15
FEATURE                 Location/Qualifiers
VARIANT                 1
                        note = Non-natural electrophile containing amino acid or
                         not present
VARIANT                 3
                        note = Any non-natural amino acid
VARIANT                 7
                        note = Any non-natural amino acid
source                  1..15
                        mol_type = protein
                        organism = synthetic construct
SEQUENCE: 147
XGXQLAXIGD DINRR                                                                 15

SEQ ID NO: 148          moltype = AA  length = 16
FEATURE                 Location/Qualifiers
VARIANT                 1
                        note = Non-natural electrophile containing amino acid or
                         not present
source                  1..16
                        mol_type = protein
                        organism = synthetic construct
SEQUENCE: 148
XEVSTVLLRL GDELEQ                                                                16

SEQ ID NO: 149          moltype = AA  length = 15
FEATURE                 Location/Qualifiers
VARIANT                 1
                        note = Non-natural electrophile containing amino acid or
                         not present
source                  1..15
                        mol_type = protein
                        organism = synthetic construct
SEQUENCE: 149
XVSTVLLRLG DELEQ                                                                 15

SEQ ID NO: 150          moltype = AA  length = 14
FEATURE                 Location/Qualifiers
VARIANT                 1
                        note = Non-natural electrophile containing amino acid or
                         not present
source                  1..14
                        mol_type = protein
                        organism = synthetic construct
SEQUENCE: 150
XSTVLLRLGD ELEQ                                                                  14

SEQ ID NO: 151          moltype = AA  length = 13
FEATURE                 Location/Qualifiers
VARIANT                 1
                        note = Non-natural electrophile containing amino acid or
                         not present
source                  1..13
                        mol_type = protein
                        organism = synthetic construct
SEQUENCE: 151
XTVLLRLGDE LEQ                                                                   13

SEQ ID NO: 152          moltype = AA  length = 16
FEATURE                 Location/Qualifiers
source                  1..16
                        mol_type = protein
                        organism = synthetic construct
```

```
SEQUENCE: 152
GQVGRQLAII GDDINR                                                      16

SEQ ID NO: 153        moltype = AA  length = 21
FEATURE               Location/Qualifiers
source                1..21
                      mol_type = protein
                      organism = synthetic construct
SEQUENCE: 153
IWIAQELRRI GDEFNAYYAR R                                                21

SEQ ID NO: 154        moltype = AA  length = 16
FEATURE               Location/Qualifiers
source                1..16
                      mol_type = protein
                      organism = synthetic construct
SEQUENCE: 154
KLSECLKRIG DELDSN                                                      16

SEQ ID NO: 155        moltype = AA  length = 16
FEATURE               Location/Qualifiers
source                1..16
                      mol_type = protein
                      organism = synthetic construct
SEQUENCE: 155
LAECTVLLRL GDELEQ                                                      16

SEQ ID NO: 156        moltype = AA  length = 26
FEATURE               Location/Qualifiers
MOD_RES               1
                      note = beta-Ala
VARIANT               14
                      note = Any non-natural amino acid
VARIANT               18
                      note = Any non-natural amino acid
source                1..26
                      mol_type = protein
                      organism = synthetic construct
SEQUENCE: 156
AAELEVECAT QLRXFGDXLN FRQKLL                                           26

SEQ ID NO: 157        moltype = AA  length = 26
FEATURE               Location/Qualifiers
MOD_RES               1
                      note = beta-Ala
VARIANT               14
                      note = Any non-natural amino acid
VARIANT               18
                      note = Any non-natural amino acid
source                1..26
                      mol_type = protein
                      organism = synthetic construct
SEQUENCE: 157
AAELEVECAT QLRXFGDXLN FRQKLL                                           26

SEQ ID NO: 158        moltype = AA  length = 26
FEATURE               Location/Qualifiers
MOD_RES               1
                      note = beta-Ala
VARIANT               14
                      note = Any non-natural amino acid
VARIANT               18
                      note = Any non-natural amino acid
source                1..26
                      mol_type = protein
                      organism = synthetic construct
SEQUENCE: 158
AAELEVESAT QLRXFGDXLN FRQKLL                                           26

SEQ ID NO: 159        moltype = AA  length = 26
FEATURE               Location/Qualifiers
MOD_RES               1
                      note = beta-Ala
VARIANT               14
                      note = Non-natural electrophile containing amino acid or
                       not present
VARIANT               18
                      note = Any non-natural amino acid
source                1..26
```

-continued

```
                          mol_type = protein
                          organism = synthetic construct
SEQUENCE: 159
AAELEVESAT QLRXFGDXLN FRQKLL                                    26

SEQ ID NO: 160          moltype = AA  length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 160
EVESATQLRX FGDXLNFRQK LLK                                       23

SEQ ID NO: 161          moltype = AA  length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 161
EVESATQLRX FGDXLNFRQK LLK                                       23

SEQ ID NO: 162          moltype = AA  length = 22
FEATURE                 Location/Qualifiers
VARIANT                 10
                        note = Any non-natural amino acid
VARIANT                 14
                        note = Any non-natural amino acid
source                  1..22
                        mol_type = protein
                        organism = synthetic construct
SEQUENCE: 162
EVESATQLRX FGDXLNFRQK LL                                        22

SEQ ID NO: 163          moltype = AA  length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 163
EVESATQLRX FGDXLNFRQK LLK                                       23

SEQ ID NO: 164          moltype = AA  length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 164
EVESATQLRX FGDXLNFRQK LLK                                       23

SEQ ID NO: 165          moltype = AA  length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 165
EVESATQLRX FGDXLNFRQK LLK                                       23

SEQ ID NO: 166          moltype = AA  length = 23
FEATURE                 Location/Qualifiers
```

```
VARIANT                 10
                        note = Any non-natural amino acid
VARIANT                 14
                        note = Any non-natural amino acid
source                  1..23
                        mol_type = protein
                        organism = synthetic construct
SEQUENCE: 166
EVESATQLRX FGDXLNFRQK LLK                                              23

SEQ ID NO: 167          moltype = AA   length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 167
EVESATQLRX FGDXLNFRQK LLK                                              23

SEQ ID NO: 168          moltype = AA   length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 168
EVESATQLRX FGDXLNFRQK LLK                                              23

SEQ ID NO: 169          moltype = AA   length = 22
FEATURE                 Location/Qualifiers
VARIANT                 10
                        note = Any non-natural amino acid
VARIANT                 14
                        note = Any non-natural amino acid
source                  1..22
                        mol_type = protein
                        organism = synthetic construct
SEQUENCE: 169
EVESATQLRX FGDXLNFRQK LL                                               22

SEQ ID NO: 170          moltype = AA   length = 23
FEATURE                 Location/Qualifiers
VARIANT                 10
                        note = Any non-natural amino acid
VARIANT                 14
                        note = Any non-natural amino acid
source                  1..23
                        mol_type = protein
                        organism = synthetic construct
SEQUENCE: 170
EVESATQLRX FGDXLNFRQK LLK                                              23

SEQ ID NO: 171          moltype = AA   length = 19
FEATURE                 Location/Qualifiers
VARIANT                 7
                        note = Any non-natural amino acid
VARIANT                 11
                        note = Any non-natural amino acid
source                  1..19
                        mol_type = protein
                        organism = synthetic construct
SEQUENCE: 171
IAQELRXIGD XFNAYYARK                                                   19

SEQ ID NO: 172          moltype = AA   length = 19
FEATURE                 Location/Qualifiers
VARIANT                 7
                        note = Any non-natural amino acid
VARIANT                 11
                        note = Any non-natural amino acid
source                  1..19
                        mol_type = protein
                        organism = synthetic construct
```

-continued

```
SEQUENCE: 172
IAQELRXIGD XFNAYYARK                                                           19

SEQ ID NO: 173           moltype = AA  length = 19
FEATURE                  Location/Qualifiers
VARIANT                  7
                         note = Any non-natural amino acid
VARIANT                  11
                         note = Any non-natural amino acid
source                   1..19
                         mol_type = protein
                         organism = synthetic construct
SEQUENCE: 173
IAQELRXIGD XFNAYYARR                                                           19

SEQ ID NO: 174           moltype = AA  length = 20
FEATURE                  Location/Qualifiers
VARIANT                  7
                         note = Any non-natural amino acid
VARIANT                  11
                         note = Any non-natural amino acid
source                   1..20
                         mol_type = protein
                         organism = synthetic construct
SEQUENCE: 174
IAQELRXIGD XFNAYYARRK                                                          20

SEQ ID NO: 175           moltype = AA  length = 19
FEATURE                  Location/Qualifiers
VARIANT                  7
                         note = Any non-natural amino acid
VARIANT                  11
                         note = Any non-natural amino acid
source                   1..19
                         mol_type = protein
                         organism = synthetic construct
SEQUENCE: 175
IAQELRXIGD XFNAYYARK                                                           19

SEQ ID NO: 176           moltype = AA  length = 19
FEATURE                  Location/Qualifiers
VARIANT                  7
                         note = Any non-natural amino acid
VARIANT                  11
                         note = Any non-natural amino acid
source                   1..19
                         mol_type = protein
                         organism = synthetic construct
SEQUENCE: 176
IAQELRXIGD XFNAYYARK                                                           19

SEQ ID NO: 177           moltype = AA  length = 19
FEATURE                  Location/Qualifiers
VARIANT                  7
                         note = Any non-natural amino acid
VARIANT                  11
                         note = Any non-natural amino acid
source                   1..19
                         mol_type = protein
                         organism = synthetic construct
SEQUENCE: 177
IAQELRXIGD XFNAYYARK                                                           19

SEQ ID NO: 178           moltype = AA  length = 19
FEATURE                  Location/Qualifiers
VARIANT                  7
                         note = Any non-natural amino acid
VARIANT                  11
                         note = Any non-natural amino acid
source                   1..19
                         mol_type = protein
                         organism = synthetic construct
SEQUENCE: 178
IAQELRXIGD XFNAYYARK                                                           19

SEQ ID NO: 179           moltype = AA  length = 19
FEATURE                  Location/Qualifiers
VARIANT                  7
                         note = Any non-natural amino acid
```

```
VARIANT             11
                    note = Any non-natural amino acid
source              1..19
                    mol_type = protein
                    organism = synthetic construct
SEQUENCE: 179
IAQELRXIGD XFANYYARK                                             19

SEQ ID NO: 180      moltype = AA  length = 19
FEATURE             Location/Qualifiers
VARIANT             7
                    note = Any non-natural amino acid
VARIANT             11
                    note = Any non-natural amino acid
source              1..19
                    mol_type = protein
                    organism = synthetic construct
SEQUENCE: 180
IAQELRXIGD XFNAYYARR                                             19

SEQ ID NO: 181      moltype = AA  length = 20
FEATURE             Location/Qualifiers
VARIANT             7
                    note = Any non-natural amino acid
VARIANT             11
                    note = Any non-natural amino acid
source              1..20
                    mol_type = protein
                    organism = synthetic construct
SEQUENCE: 181
IAQELRXIGD XFNAYYARRK                                            20

SEQ ID NO: 182      moltype = AA  length = 22
FEATURE             Location/Qualifiers
MOD_RES             1
                    note = beta-Ala
VARIANT             10
                    note = Any non-natural amino acid
VARIANT             14
                    note = Any non-natural amino acid
source              1..22
                    mol_type = protein
                    organism = synthetic construct
SEQUENCE: 182
AIWIAQELRX IGDXFNAYYA RR                                         22

SEQ ID NO: 183      moltype = AA  length = 19
FEATURE             Location/Qualifiers
VARIANT             7
                    note = Any non-natural amino acid
VARIANT             11
                    note = Any non-natural amino acid
source              1..19
                    mol_type = protein
                    organism = synthetic construct
SEQUENCE: 183
IAQELRXIGD XFNAYYARR                                             19

SEQ ID NO: 184      moltype = AA  length = 21
FEATURE             Location/Qualifiers
VARIANT             9
                    note = Any non-natural amino acid
VARIANT             13
                    note = Any non-natural amino acid
source              1..21
                    mol_type = protein
                    organism = synthetic construct
SEQUENCE: 184
IWIAQELRXI GDXFNAYYAR R                                          21

SEQ ID NO: 185      moltype = AA  length = 40
FEATURE             Location/Qualifiers
source              1..40
                    mol_type = protein
                    organism = synthetic construct
SEQUENCE: 185
GSHMINVNKK ALGQDTEKME EQLDLLSAIL DPSKSKGAGS                      40

SEQ ID NO: 186      moltype = AA  length = 25
```

-continued

```
FEATURE              Location/Qualifiers
source               1..25
                     mol_type = protein
                     organism = synthetic construct
SEQUENCE: 186
AELEVECATQ LRRFGDKLNF RQKLL                                          25

SEQ ID NO: 187       moltype = AA   length = 9
FEATURE              Location/Qualifiers
source               1..9
                     mol_type = protein
                     organism = synthetic construct
SEQUENCE: 187
HHHHHHHHH                                                            9
```

The invention claimed is:

1. A stapled peptide comprising:

(i) LKXJLRXHRFLWQR (SEQ ID NO: 13), wherein the first X is cross-linked to the second X;

(ii) LKXALRXJRFLWQR (SEQ ID NO:14), wherein the first X is cross-linked to the second X;

(iii) LKXALRXHRFLJQR (SEQ ID NO:15), wherein the first X is cross-linked to the second X;

(iv) LKKJLRRHXFLWXR (SEQ ID NO:16), wherein the first X is cross-linked to the second X;

(v) LKKALRRJXFLWXR (SEQ ID NO:17), wherein the first X is cross-linked to the second X;

(vi) LKKALRRHXFLJXR (SEQ ID NO:18), wherein the first X is cross-linked to the second X;

(vii) L8KJLRRHXFLWQR (SEQ ID NO:19), wherein 8 is cross-linked to X;

(viii) L8KALRRJXFLWQR (SEQ ID NO:20), wherein 8 is cross-linked to X; or (ix) L8KALRRHXFLJQR (SEQ ID NO:21), wherein 8 is cross-linked to X; and wherein X is S-pentenyl alanine, 8 is R-octenyl alanine, and J is a non-natural electrophile containing amino acid.

2. The stapled peptide of claim 1, wherein the non-natural electrophile containing amino acid comprises acrylamide.

3. The stapled peptide of claim 1, which is no more than 30 amino acids in length.

4. A pharmaceutical composition comprising the stapled peptide of claim 1 and a pharmaceutically acceptable carrier.

5. A pharmaceutical composition comprising the stapled peptide of claim 3 and a pharmaceutically acceptable carrier.

* * * * *